(12) United States Patent
Witelson et al.

(10) Patent No.: US 9,903,130 B2
(45) Date of Patent: *Feb. 27, 2018

(54) AUTONOMOUS POOL CLEANING ROBOT WITH AN EXTERNAL DOCKING STATION

(71) Applicant: MAYTRONICS LTD., Kibutz Yizrael (IL)

(72) Inventors: Shay Witelson, Yizrael (IL); Oded Golan, Kefar Tavor (IL); Boaz Ben Dov, Ram On (IL); Amir Gilead, Haifa (IL)

(73) Assignee: MAYTRONICS LTD., Kibbuts Yizrael (IL)

( * ) Notice: Subject to any disclaimer, the term of this patent is extended or adjusted under 35 U.S.C. 154(b) by 363 days.

This patent is subject to a terminal disclaimer.

(21) Appl. No.: 14/710,615

(22) Filed: May 13, 2015

(65) Prior Publication Data

US 2015/0314453 A1 Nov. 5, 2015

Related U.S. Application Data

(63) Continuation-in-part of application No. 14/433,859, filed as application No. PCT/IL2013/051055 on Dec. 22, 2013.

(Continued)

(51) Int. Cl.
*B01D 35/00* (2006.01)
*E04H 4/16* (2006.01)
(Continued)

(52) U.S. Cl.
CPC ............ *E04H 4/1654* (2013.01); *A61L 2/10* (2013.01); *B25J 11/00* (2013.01); *H02J 7/025* (2013.01); *H02J 17/00* (2013.01)

(58) Field of Classification Search
CPC ... E04H 4/1654; E04H 4/1209; B01D 29/114; B01D 29/668; B01D 29/52; B01D 46/0057; B01D 46/0058
(Continued)

(56) References Cited

U.S. PATENT DOCUMENTS

| 6,842,931 B2* | 1/2005 | Porat ................... E04H 4/1654 15/1.7 |
| 2008/0078039 A1* | 4/2008 | Katz ................... E04H 4/1654 15/1.7 |
| 2009/0049640 A1* | 2/2009 | Lee ........................ A47L 9/20 15/319 |

FOREIGN PATENT DOCUMENTS

| EP | 314259 A2 * | 5/1989 |
| FR | 2742351 A1 * | 9/1997 |

OTHER PUBLICATIONS

Pappalardo, FR 2742351 English machine Translation, Jun. 20, 1997, pp. 1-6.*

(Continued)

*Primary Examiner* — Claire A Norris
(74) *Attorney, Agent, or Firm* — Reches Patents

(57) ABSTRACT

An external docking station may be provided and may include a filter manipulator that is arranged to (i) input a filter into a pool cleaning robot that exited a pool and is located in a filter replacement position and to (ii) assist in positioning the filter at a filtering position in which the filter is at least partially disposed within a fluid path formed between a first fluid opening and a second fluid opening of the housing thereby allowing the filter to apply a filtering operation on fluid that passes through the fluid path.

39 Claims, 56 Drawing Sheets

Related U.S. Application Data

(60) Provisional application No. 61/992,247, filed on May 13, 2014, provisional application No. 61/745,556, filed on Dec. 22, 2012.

(51) Int. Cl.
*B25J 11/00* (2006.01)
*H02J 7/02* (2016.01)
*A61L 2/10* (2006.01)
*H02J 17/00* (2006.01)

(58) Field of Classification Search
USPC .................................. 210/107, 167.1; 15/1.7
See application file for complete search history.

(56) References Cited

OTHER PUBLICATIONS

Puech, EP314259, English Machine Translation, May 3, 1989, pp. 1-9.*

* cited by examiner

Performing, by at least one of a pool cleaning robot and an underwater station, in an autonomous manner at least one out of pool cleaning robot filter replacement and pool cleaning robot charging. 410

Filtering fluid by a pool cleaning robot by using a filter that fulfils at least one of the following: (i) it has a filter core that is rotated by a filter core rotator when the filter applied a filtering operation, (ii) is positioned in a filtering position while at least one other filter of the pool cleaning robot is positioned within the pool cleaning robot in a non-filtering position, (iii) is positioned in a filtering position when the pool cleaning robot and by a filter manipulator. 510

Performing, by at least one of a pool cleaning robot and an external docking station, in an autonomous manner at least one out of pool cleaning robot filter replacement and pool cleaning robot charging. 810

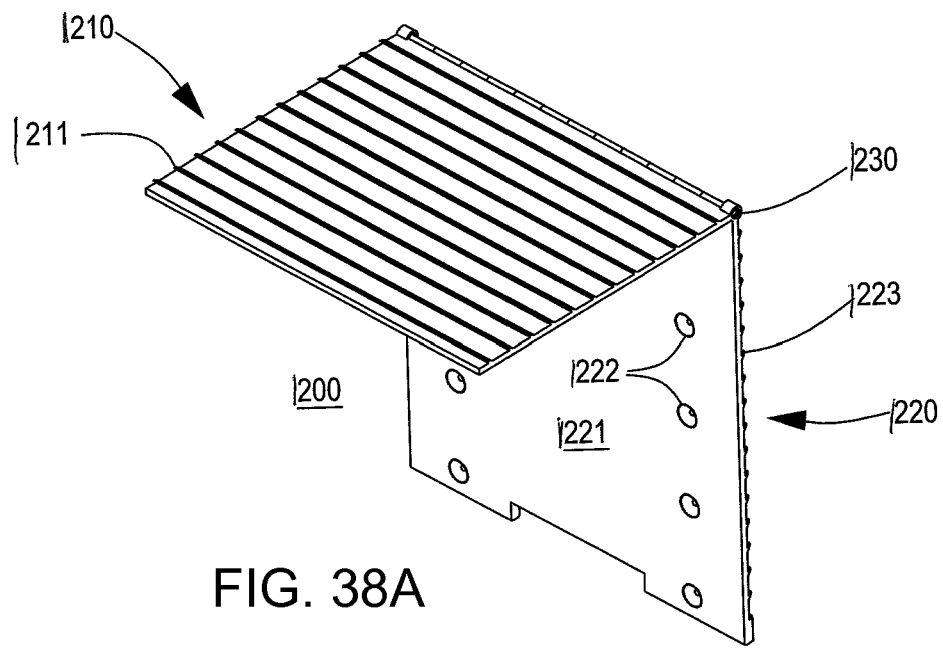
FIG. 38A
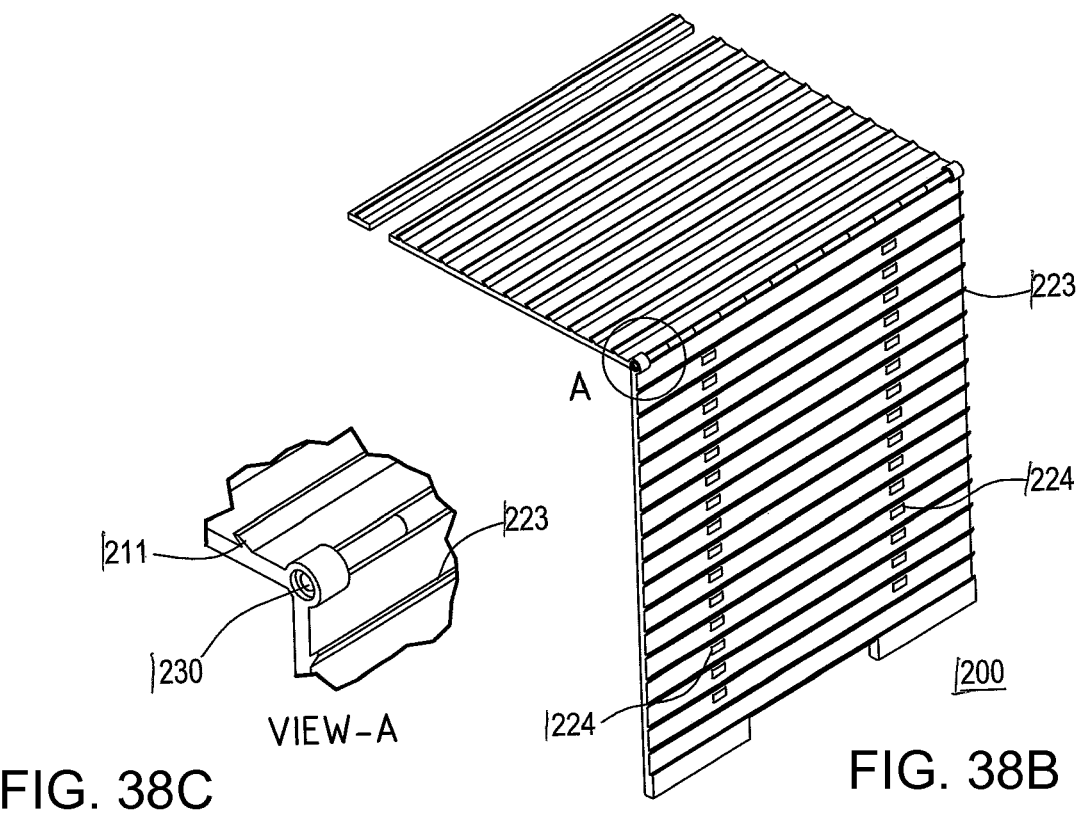
FIG. 38C
FIG. 38B

AUTONOMOUS POOL CLEANING ROBOT WITH AN EXTERNAL DOCKING STATION

RELATED APPLICATIONS

This application claims priority from U.S. provisional patent 61/992,247 filing date May 13, 2014 which is incorporated herein by reference in its entirety.

This application is a continuation in part of U.S. patent application Ser. No. 14/433,859 filing date Apr. 7, 2015 which is a national phase application of PCT patent application serial number PCT/IL2013/051055 international filing date 22 Dec. 2013 which claims priority from U.S. provisional patent Ser. No. 61/745,556 filing date 22 Dec. 2012—both PCT patent application and the U.S. provisional patent are incorporated herein by reference in their entirety.

FIELD OF THE INVENTION

This invention relates to pool cleaning robots, and particularly to autonomous pool cleaning robots.

BACKGROUND OF THE INVENTION

Pool cleaning robots are adapted for use for cleaning a pool while being connected to electrical power cables or to a hose of a suction system. The hose and/or power cable can get tangled and may temporarily limit the usage of the pool.

Once a filter of a pool cleaning robot is clogged the pool cleaning robot is manually taken out of the pool and its filter can be washed by a user of the pool cleaning robot.

Taking a pool cleaning robot out of the pool is a time and effort consuming operation that is not very fond by the users. In many cases the users delay these manual operations or even skip them causing the pool cleaning robot to operate in a sub-optimal manner.

There is a growing need to provide autonomous robots that require a lesser amount of human intervention in their maintenance.

SUMMARY OF THE INVENTION

According to an embodiment of the invention there may be provided an external docking station. The docking station is external because it is external to a pool—it is not fully underwater.

According to an embodiment of the invention there may be provided an external docking station that may include a filter manipulator that may be arranged to (i) input a filter into a pool cleaning robot that exited a pool and is located in a filter replacement position and to (ii) assist in positioning the filter at a filtering position in which the filter is at least partially disposed within a fluid path formed between a first fluid opening and a second fluid opening of the housing thereby allowing the filter to apply a filtering operation on fluid that passes through the fluid path.

The filter storage module may include a first portion that may be arranged to store at least one filter before the at least one filter is inputted to the pool cleaning robot and a second portion that may be arranged to store at least one used filter after the at least one used filter was outputted from the pool cleaning robot; wherein the first portion and the second portions are positioned at two sides of the pool cleaning robot when the pool cleaning robot is positioned at the filter replacement position.

The external docking station may include a winding and unwinding mechanism that may be arranged to wind and unwind an interfacing device that may be interfaced by the pool cleaning robot during at least one process out of a pool exit process and a propagation process towards the external docking station.

The filter storage module may include a first portion that may be arranged to store at least one filter before the at least one filter is inputted to the pool cleaning robot and a second portion that may be arranged to store at least one used filter after the at least one used filter was outputted from the pool cleaning robot; wherein the first portion and the second portions are positioned at two sides of the pool cleaning robot when the pool cleaning robot is positioned at the filter replacement position; wherein the winding and unwinding mechanism may be configured to unwind the interface device thereby causing the interface device to propagate through a gap between the first portion of the filter storage module and the second portion of the filter storage module.

The first portion may be positioned within a first enclosure; wherein the second portion may be positioned with a second enclosure.

The external docking station may include an electric cable winding and unwinding mechanism that may be arranged to wind and unwind an electric cable that may be configured to supply power to the pool cleaning robot.

The electric cable winding and unwinding mechanism may be positioned within the first enclosure or the second enclosure.

The first enclosure may include a first opening for outputting the at least one filter into the pool cleaning robot; wherein the second enclosure may include a second opening for receiving the at least one used filter from the pool cleaning robot.

The first opening faces the second opening.

The external docking station may include at least one power supply element for contacting at least one element of the pool cleaning robot and providing power to the at least one element of the pool cleaning robot.

the at least one power supply element may be positioned in a second housing; wherein the filter storage module may include a first portion that may be arranged to store at least one filter before the at least one filter is inputted to the pool cleaning robot and a second portion that may be arranged to store at least one used filter after the at least one used filter was outputted from the pool cleaning robot.

The first portion, the second portion and the third housing are positioned at three sides of the pool cleaning robot when the pool cleaning robot is positioned at the filter replacement position.

The external docking station may include at least one rotating element for interfacing between the external docking station and a surface on which the external surface propagates.

The external docking station may include a first contactless charging element that may be arranged to (a) be fed by the electrical supply module and (b) generate an electromagnetic field during at least one period during which a second contactless charging element of a pool cleaning robot is within a charging range from the first contactless charging element, and wherein the electromagnetic field charges the second contactless charging element.

The external docking station may include at least one radiation source for emitting electromagnetic radiation.

The external docking station may include multiple spaced apart radiation sources for emitting electromagnetic radiation that assist in a navigation of the pool cleaning robot towards the external docking station.

The external docking station may include a washing module for washing the pool cleaning robot internal cavity.

The external docking station may include a fluid conduit that faces an opening of the pool cleaning robot and may be configured to washing an interior of the pool cleaning robot.

The filter manipulator may be arranged to position the filter at the filtering position.

The filter manipulator may be arranged to receive multiple filters and to feed at least two filters in the robot.

The filter manipulator may include a filter storage module that may be arranged to store multiple used filters after the used filters were outputted from the pool cleaning robot.

The filter manipulator may include a filter storage module that may be arranged to store multiple filters before the multiple filters are inputted to the pool cleaning robot.

The filter manipulator may include a filter storage module that may be arranged to store multiple used filters after the used filters were outputted from the pool cleaning robot and may be arranged to store multiple filters before the multiple filters are inputted to the pool cleaning robot.

the filter manipulator may include a first portion for storing at least one filter and for feeding the at least one filter to the pool cleaning robot and a second portion for receiving one or more used filters from the robot.

The first portion may be configured to push a filter onto the pool cleaning robot thereby causing a used filter to exit the robot and be provided to the second portion.

The filter manipulator may include a filter storage module that may be arranged to store multiple filters and a movement mechanism.

The movement mechanism may be arranged to move at least one of the filter storage module and the filter in order to input the filter into the pool cleaning robot.

The movement mechanism may be arranged to assist in moving the filter within the housing thereby placing another filter of the multiple filters at the filtering position.

The filter storage module has a radial symmetry.

The movement mechanism may include (a) a rotation unit that may be arranged to rotate the filter storage module thereby positioning the filter in front of a filter opening formed in the pool cleaning robot, and (b) an insertion and ejection module that may be arranged to cause the filter to pass through the filter opening.

The filter opening may be formed at the bottom of the pool cleaning robot and wherein the insertion and ejection module may be arranged to lift the filter through the filter opening.

The movement mechanism may be arranged to input the filter in the pool cleaning robot by moving the filter without moving the storage module.

The filter manipulator may be arranged to assist in an outputting of the filter from the robot.

The external docking station may include a processing module for processing used filters that were outputted from the pool cleaning robot.

The processing module may be arranged to compress the used filters.

The processing module may be arranged to shred the used filters.

The processing module may be arranged to sanitize the used filters.

The external docking station may include a sanitizer for sanitizing used filters.

According to an embodiment of the invention there may be provided a docking station that is not positioned underwater and may include a filter or a debris collecting container manipulator that may be arranged to (i) input a filter or a debris collecting container into a cleaning robot that exited a work area and may be located in a filter or a debris collecting container replacement position and to (ii) assist in positioning the filter or a debris collecting container at a filtering or debris collecting position in which the filter or debris collecting container may be at least partially disposed within a fluid or a debris collecting path formed between a first fluid or debris ingress opening and a second egress opening in the housing thereby allowing the filter or debris collecting container to apply a filtering or debris ingress operation on fluid or debris that passes through the fluid or debris collecting path.

BRIEF DESCRIPTION OF THE DRAWINGS

In order to understand the invention and to see how it may be carried out in practice, an embodiment will now be described, by way of a non-limiting example only, with reference to the accompanying drawings, in which:

FIG. 21 illustrates a method according to an embodiment of the invention;

FIG. 22 illustrates a method according to an embodiment of the invention;

FIG. 27 illustrates a method according to an embodiment of the invention;

FIGS. 38A-38C illustrate an interfacing device according to an embodiment of the invention.

DETAILED DESCRIPTION OF EMBODIMENTS

According to various embodiments of the invention there is provided an external docking system that can perform various maintenance operations on a pool cleaning robot. An external docking system may be highly efficient and relatively compact. It is easier to maintain than an underwater docking station and may be suited for all types of pools—including pools that are already build when purchasing the external docking station. External docking station may fit to pools of any shape and size, does not reduce the usable volume of the pool and does not form an underwater hazard.

The pool cleaning robot can be being charged while being underwater.

Contactless Underwater Charging of a Pool Cleaning Robot

Figure 1:
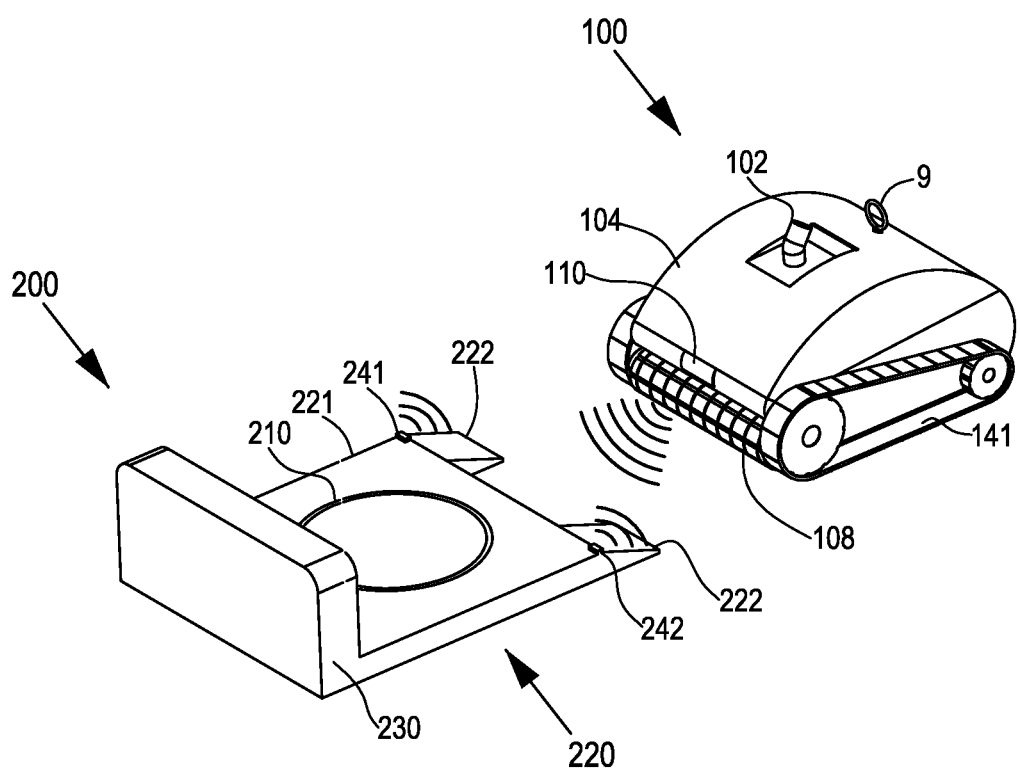
FIG. 1 illustrates a pool cleaning robot and an underwater station according to an embodiment of the invention.
Figure 3A:
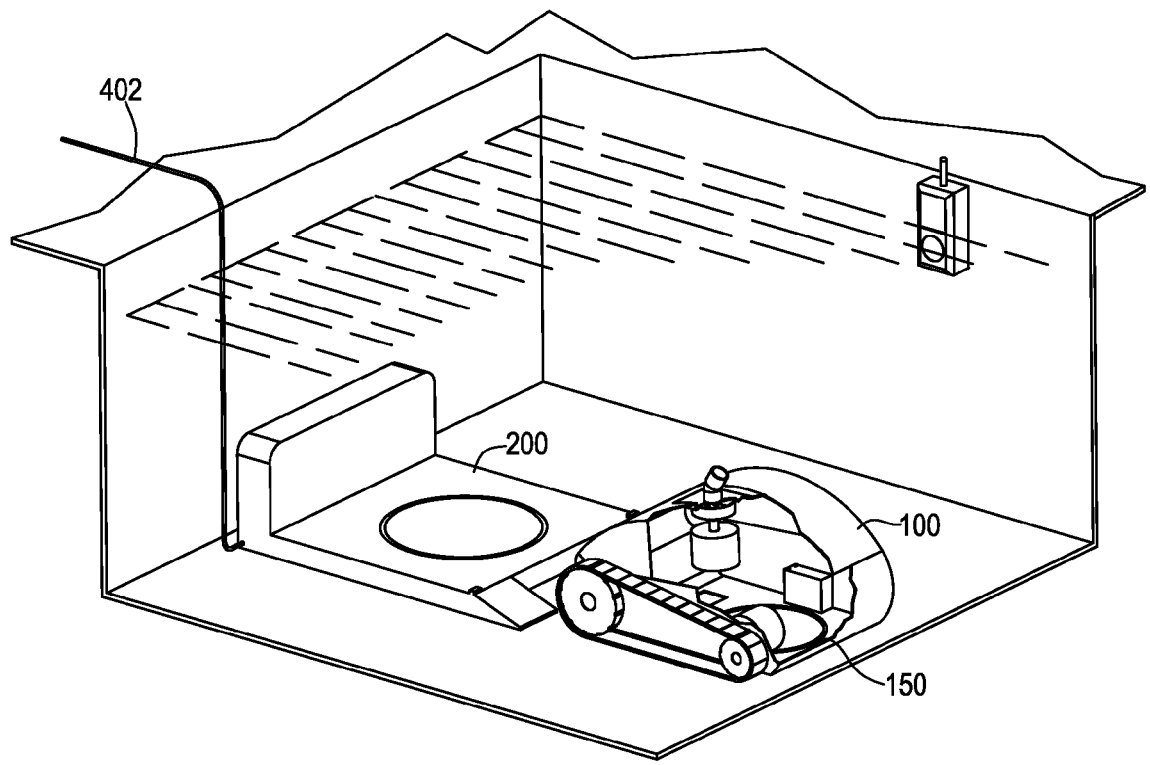
FIG. 3A illustrates a portion of a pool, a pool cleaning robot and an underwater station according to an embodiment of the invention.
Figure 3B:
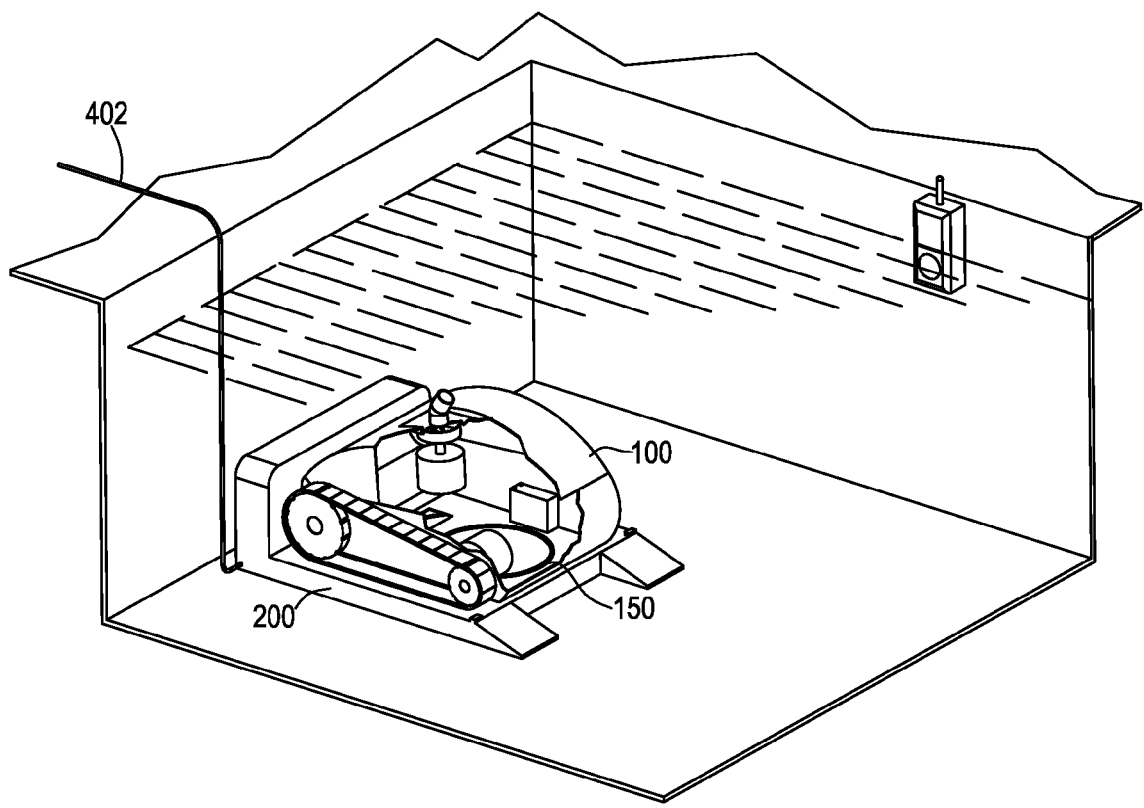
FIG. 3B illustrates a portion of a pool and pool cleaning robot that is wirelessly charged by an underwater station while being positioned on a platform of the underwater station according to an embodiment of the invention.

FIGS. 1 and 3A illustrate a pool cleaning robot 100 that approaches an underwater station 200 according to an embodiment of the invention. FIG. 3B illustrates a pool cleaning robot 100 that is mounted on an underwater station 200 according to an embodiment of the invention.

The underwater station of FIG. 1 is illustrated as including an erect portion 230, a platform 230 on which the pool cleaning robot can mount, a first contactless charging element 210, and radiation sources 241 and 242. Radiation sources 241 and 242 may be spaced apart from each other and are arranged to emit radiation (such as ultrasonic radiation) that can be detected by sensor 110 of pool cleaning robot 100 and allow the pool cleaning robot 100 to navigate towards the underwater station 200. The pool cleaning robot 100 may compare between the radiation received from the different radiation sources (241 and 242) and direct itself toward the underwater station 200. The radiation sources 241 and 242 may emit radiation of different frequencies, in different points of time and the like.

The platform 230 is illustrated as including flat surface 221 and rails 222 that ease the mounting of the pool cleaning robot on the flat surface 221. A first contactless charging element 210 may be connected to the platform 220, embedded in the platform 220 or otherwise included in the underwater station 200 and may be used to charge the pool cleaning robot 100 that in turn has a second contactless charging element (denoted 150 in FIGS. 3A and 3B) to facilitate the contactless charging of the pool cleaning robot 100. FIGS. 3A and 3B also illustrate a cable 402 that feeds the underwater station with electrical power. This electrical power can be supplied to the first contactless charging element 210.

FIG. 1 also illustrates a holding element such as ring 9 that can be contacted when the pool cleaning robot 100 is taken out of the pool.

Figure 4A:
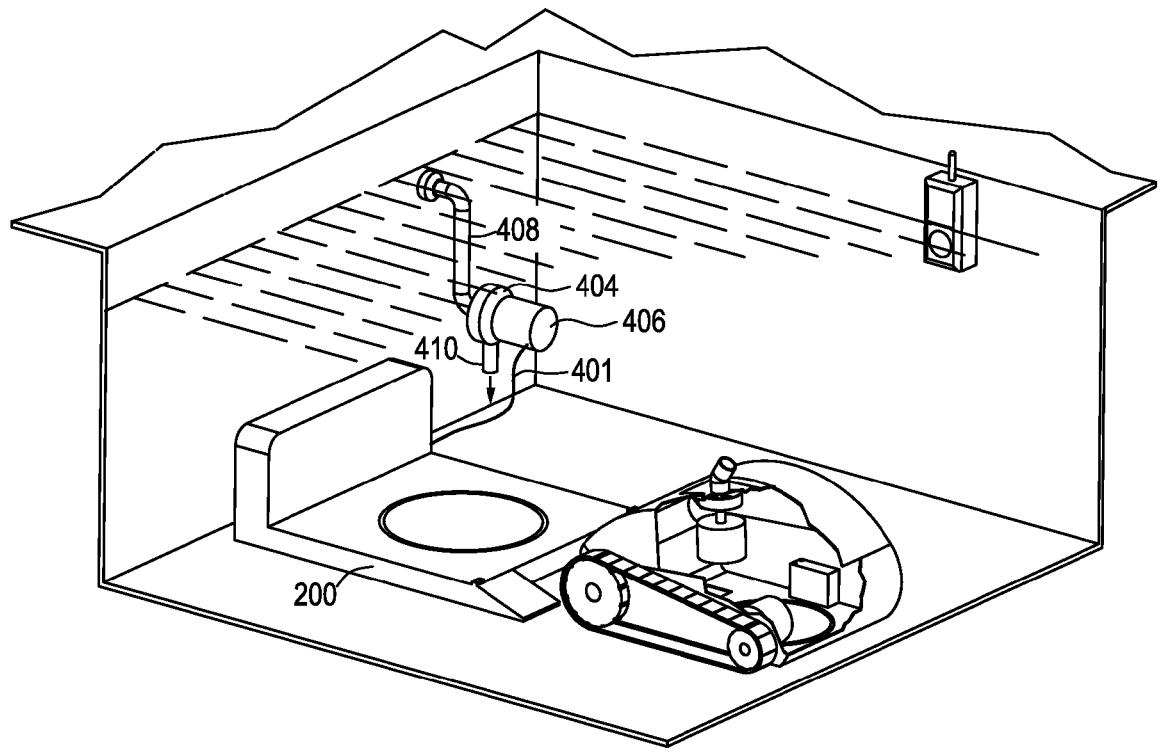
FIG. 4A illustrates a portion of a pool, a pool cleaning robot, an underwater station, a turbine, an electrical generator that feeds the underwater station and a tube of a pool fluid circulation system according to an embodiment of the invention.
Figure 4B:
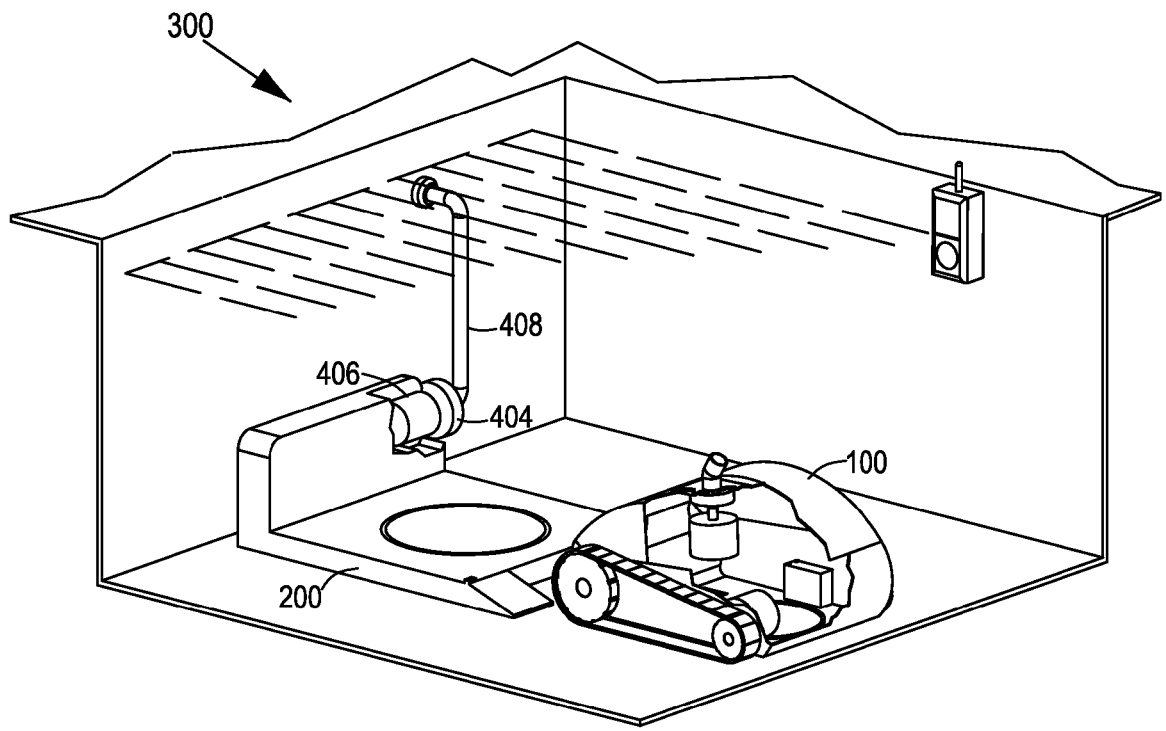
FIG. 4B illustrates a portion of a pool, a pool cleaning robot, an underwater station, a turbine, an electrical generator that form a part of the underwater station and a tube of a pool fluid circulation system according to an embodiment of the invention.

Charging a Pool Cleaning Robot Using a Flow of Fluid that Induced by a Pool Fluid Circulation System A pool cleaning robot may be charged using a flow of fluid that is induced by a pool fluid circulation system. A turbine that is rotated by the flow of fluid can be included in the pool cleaning robot (as shown in FIGS. 2A, 2B, 2C and 4C), can be included in an underwater station (as shown in FIG. 4B) or can be coupled to the underwater pool cleaning robot (as shown in FIG. 4A).

Figure 2A:
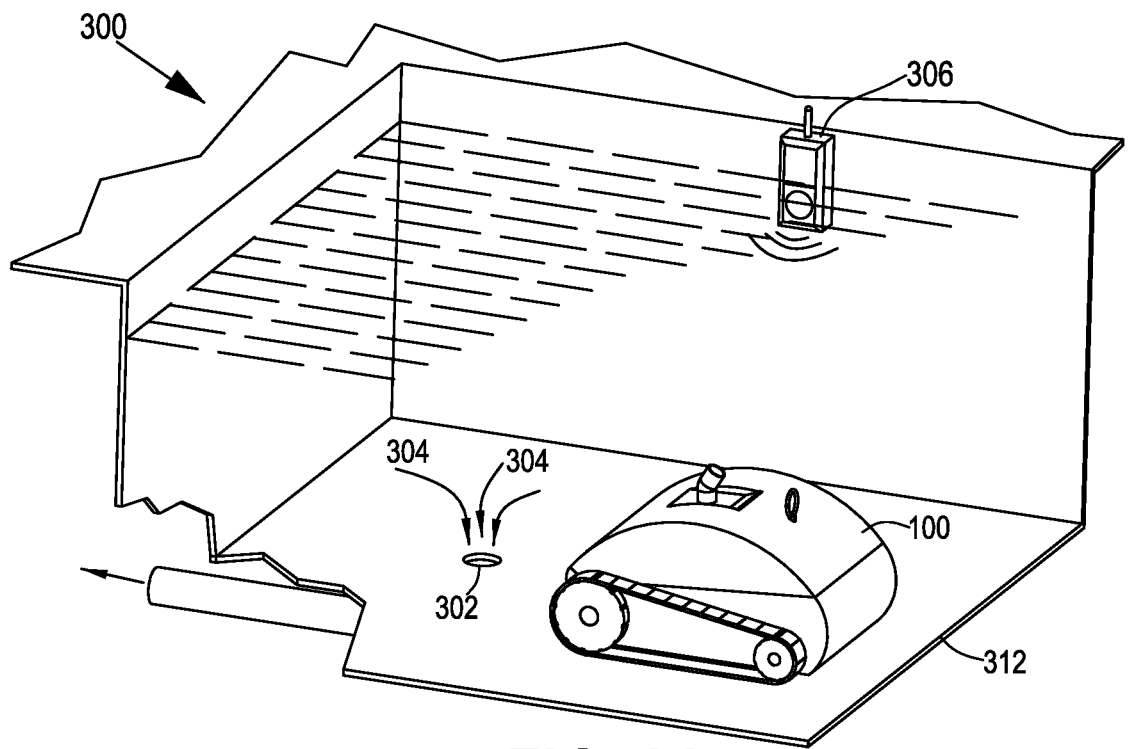
FIG. 2A illustrates a portion of a pool, a pool cleaning robot and a drain of the pool according to an embodiment of the invention.
Figure 2B:
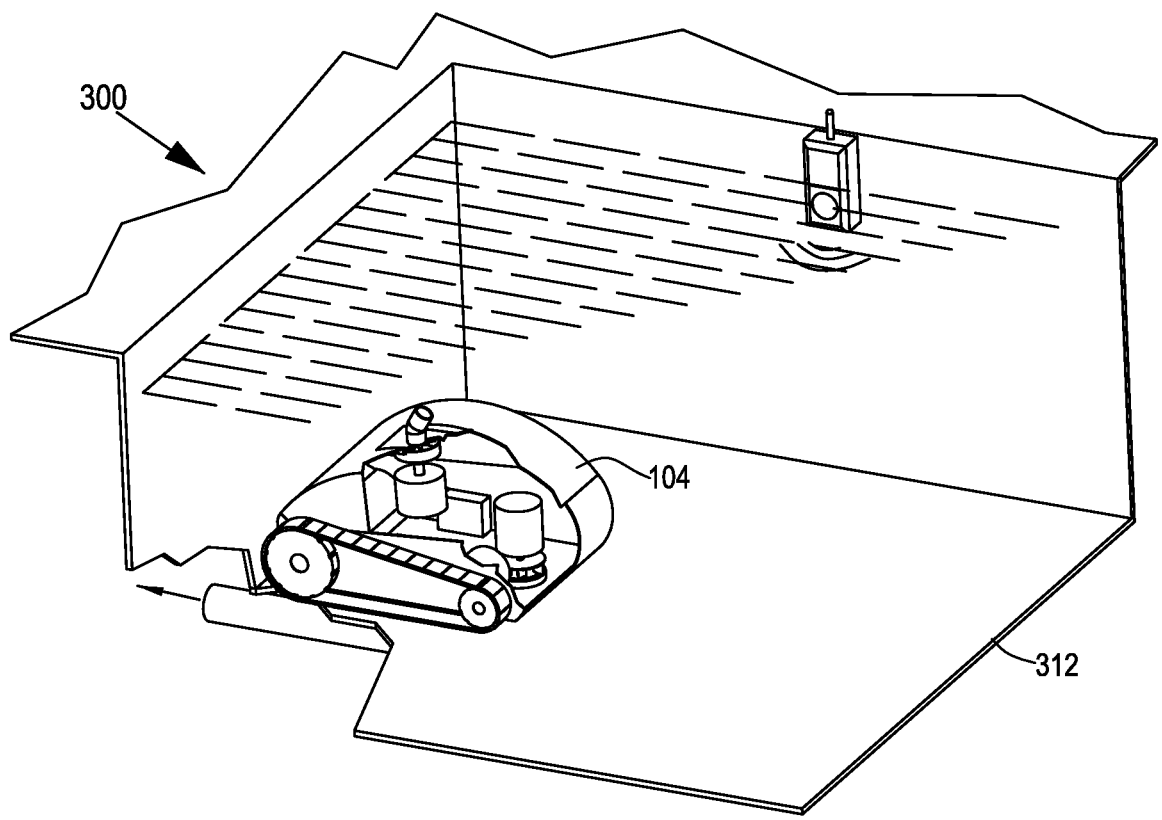
FIG. 2B illustrates a portion of a pool and a pool cleaning robot that is positioned on top of a drain of the pool according to an embodiment of the invention.
Figure 2C:
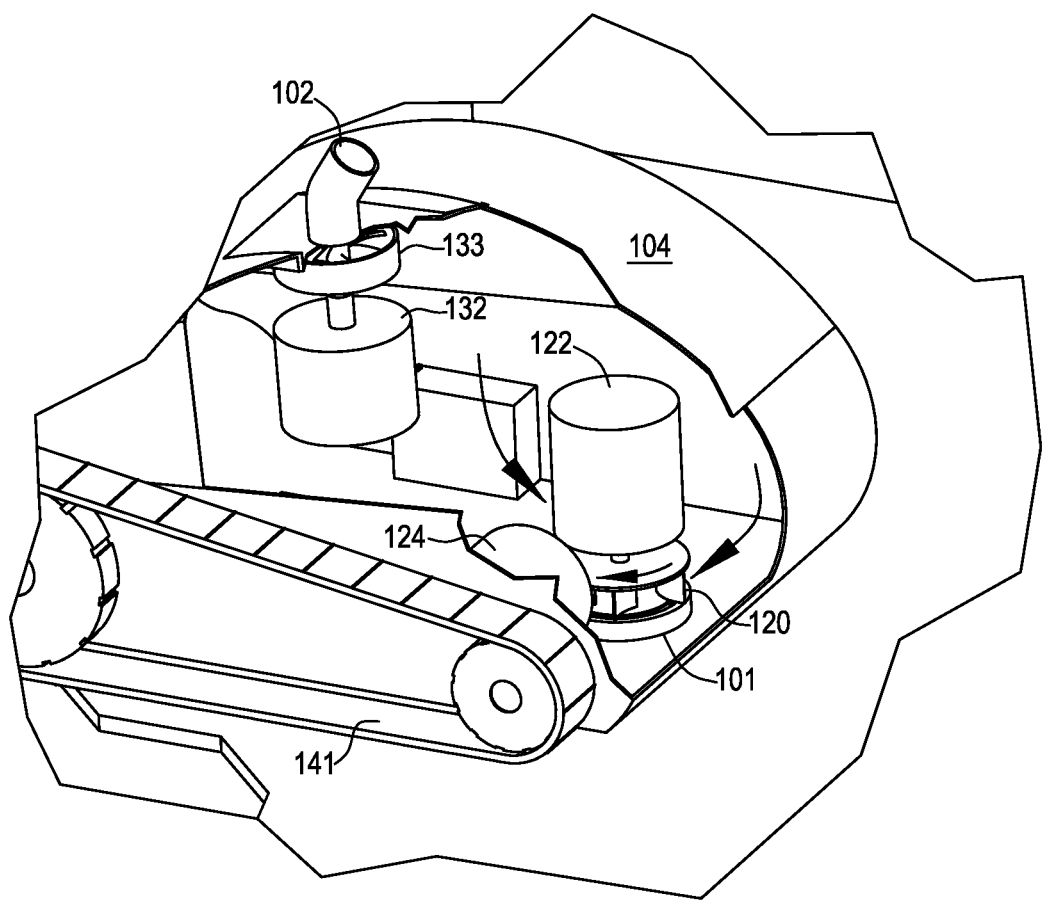
FIG. 2C illustrates a portion of a pool cleaning robot that is positioned on top of a drain of the pool according to an embodiment of the invention.

FIG. 2C illustrates a pool cleaning robot 100 while FIGS. 2A and 2B illustrate the pool cleaning robot 100 as well as a portion of a pool 300 and a drain 302 of the pool according to an embodiment of the invention. In FIG. 2A the pool cleaning robot 100 is near the drain 302 while in FIG. 2B the pool cleaning robot is on top of the drain (not shown). FIG. 2A also illustrates a communication module 306 for communication with the pool cleaning robot 100.

Referring to FIG. 2C—pool cleaning robot 100 includes turbine 120, housing 104, first fluid opening 101' and second fluid opening 102 formed in the housing 104, electrical generator 122, pump motor 132, impeller 133, rechargeable power source such as battery 135, drive motor 124 and first track 141. Non-limiting examples of additional and/or alternative components and modules of the pool cleaning robot 100 are illustrated in FIGS. 18A-18H.

The turbine 120 is positioned above a first fluid opening 101' formed at the bottom of the pool cleaning robot 100 and below second fluid opening 102.

The turbine 120 is at least partially disposed within a fluid path formed between the first fluid opening 101' so as to extract energy from flow of fluid through the fluid path.

Electrical generator 122 is arranged to provide electrical power thereto and adapted to be driven by the turbine 120.

The rechargeable power source 135 is arranged to be charged by the electrical generator 122 and to supply electrical power during at least one period of time during which the turbine 120 does not extract energy from the flow of fluid.

When positioned in proximity of the drain 302, fluid is sucked from second fluid outlet 102, through the fluid path and exits the pool cleaning robot via the first fluid opening 101' thereby rotating the turbine 120.

Figure 20:
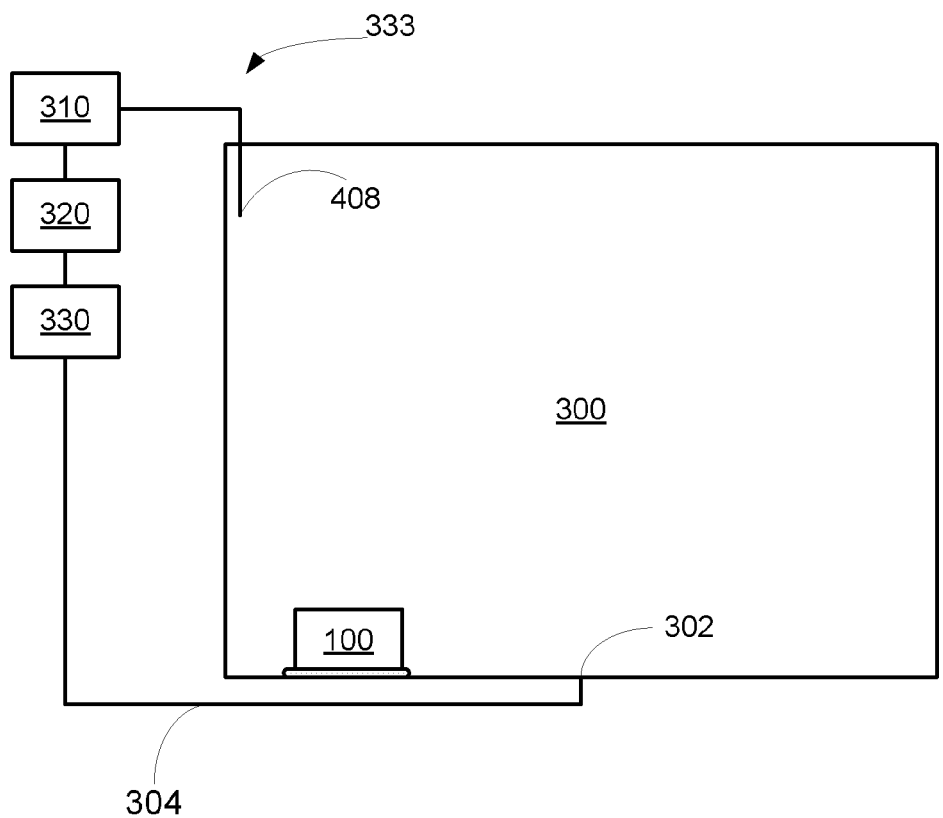
FIG. 20 illustrates a pool, a poll pool cleaning robot and a pool fluid circulation system according to an embodiment of the invention.

It is noted that charging the pool cleaning robot 100 by the drain 302 is an example of charging the pool cleaning robot by a flow of fluid that is induced by a pool fluid circulation system (denoted 333 in FIG. 20A).

Yet for another example—pool cleaning robot may be located in proximity (or in contact with) an output of a tube (denoted 408 in FIG. 4C) of the pool fluid circulation system.

It is expected that the pool cleaning robot 100 needs to be relatively proximate (few centimeters till few tenths of centimeters) from an inlet or outlet of the pool fluid circulation system in order that a sufficient amount of flow of fluid is induced to flow through the fluid path and thereby rotating turbine 120.

Accordingly—the charging may occur when the pool cleaning robot 100 is positioned in a certain location in which a flow level of fluid that is circulated by a pool fluid circulation system is higher than a flow level of the fluid within a majority of the pool or even be the highest flow level in the pool. When positioned at the certain location the fluid that is circulated by the pool fluid circulation system passes through the fluid path formed in the pool cleaning robot.

FIG. 4A illustrates a portion of a pool 300, a pool cleaning robot 100, an underwater station 200, a turbine 404, an electrical generator 406 that feeds the underwater station 200 with electrical power via cable 401 and a tube 408 of a pool fluid circulation system according to an embodiment of the invention. Turbine 404 and electrical generator 406 are submerged and do not belong to the underwater station 200 or to the pool cleaning robot 100. Tube 408 can direct a jet of fluid towards turbine 404 or may such fluid from the pool. Turbine has an outlet 410 for allowing fluid that is jetted by the tube 408 to enter the pool and/or to allow fluid sucked through tube 408 to enter turbine 404.

FIG. 4B illustrates a portion of a pool 300, a pool cleaning robot 100, an underwater station 200 as well as a turbine 404 and an electrical generator 406 that form a part of the underwater station 200 that feeds the underwater station according to an embodiment of the invention. Turbine 404 is rotated by a flow of fluid induced by tube 408 of the pool fluid circulation system.

Figure 4C:
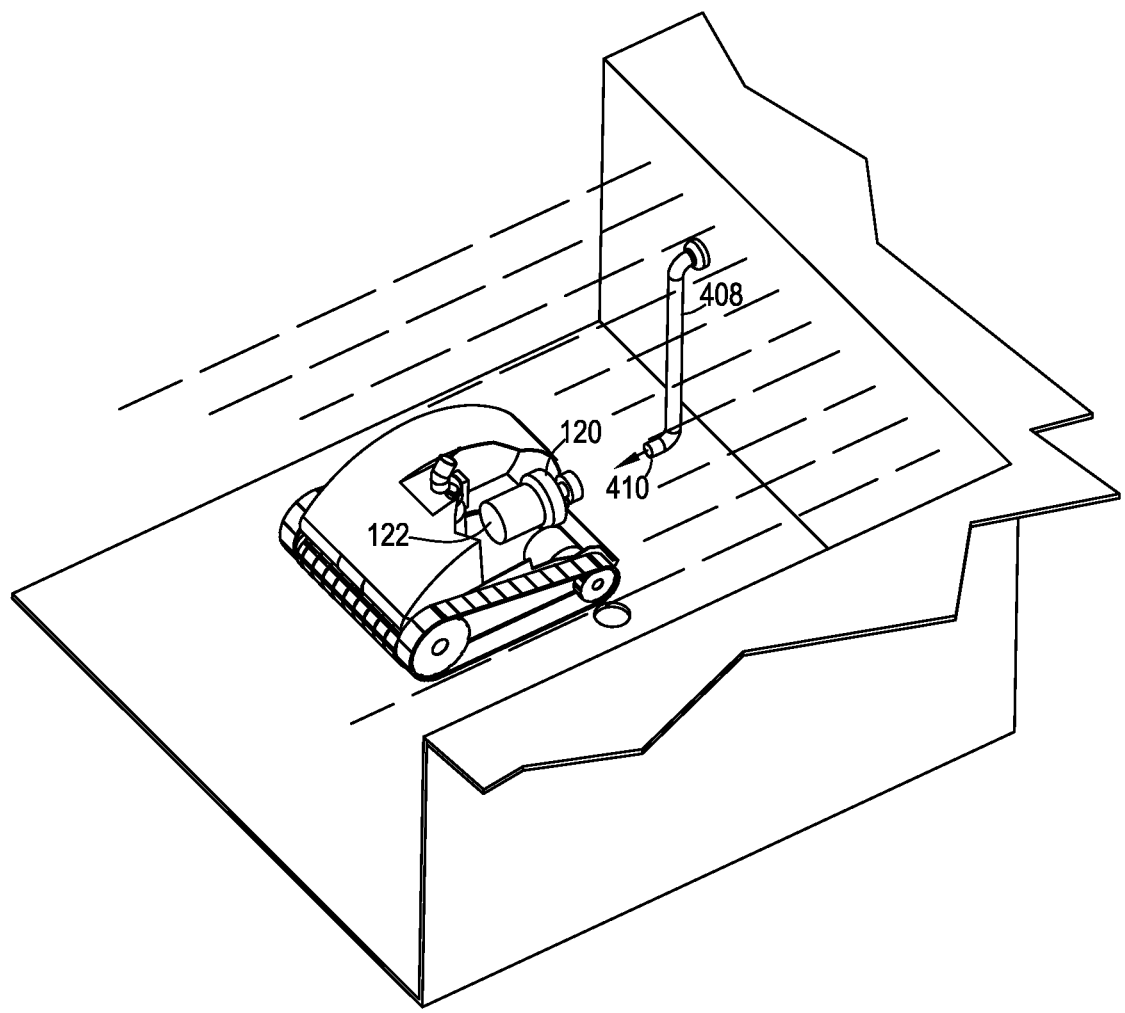
FIG. 4C illustrates a portion of a pool, a pool cleaning robot that includes a turbine and an electrical generator and a tube of a pool fluid circulation system according to an embodiment of the invention.

FIG. 4C illustrates a portion of a pool 300, tube 408 and a pool cleaning robot 100 that includes turbine 404 and electrical generator 406 according to an embodiment of the invention. The turbine 404 is rotated by a flow of fluid induced by tube 408 of the pool fluid circulation system. This may require the pool cleaning robot to direct turbine 404 (facing one of the sides of the pool cleaning robot—but not its bottom) to be positioned near the opening of tube 408.

Underwater Filter Replacement

Additionally or alternatively, filters of the pool cleaning robot can be inserted to the pool cleaning robot underwater, ejected from the pool cleaning robot underwater, replaced underwater and/or processed underwater. The insertion and/or the ejection and/or the replacement of the filters can be executed by the robot, by an underwater station of by a combination of both.

Figure 5A:
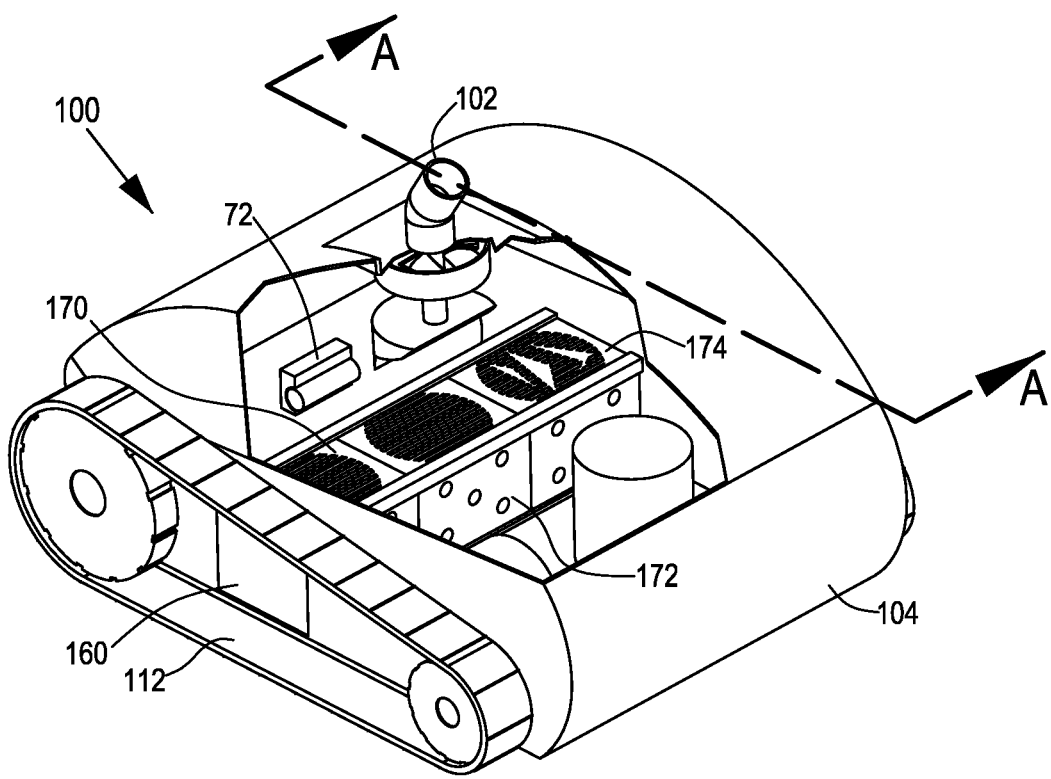
FIG. 5A illustrates a pool cleaning robot that includes multiple filters according to an embodiment of the invention.
Figure 5B:
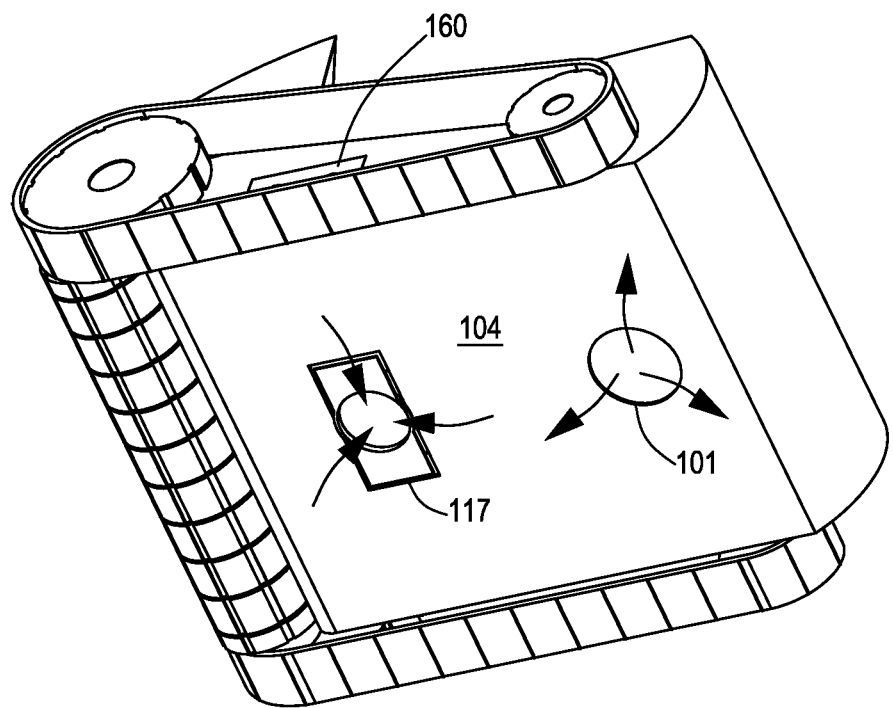
FIG. 5B illustrates a bottom of a housing of a pool cleaning robot that includes multiple filters according to an embodiment of the invention.
Figure 5C:
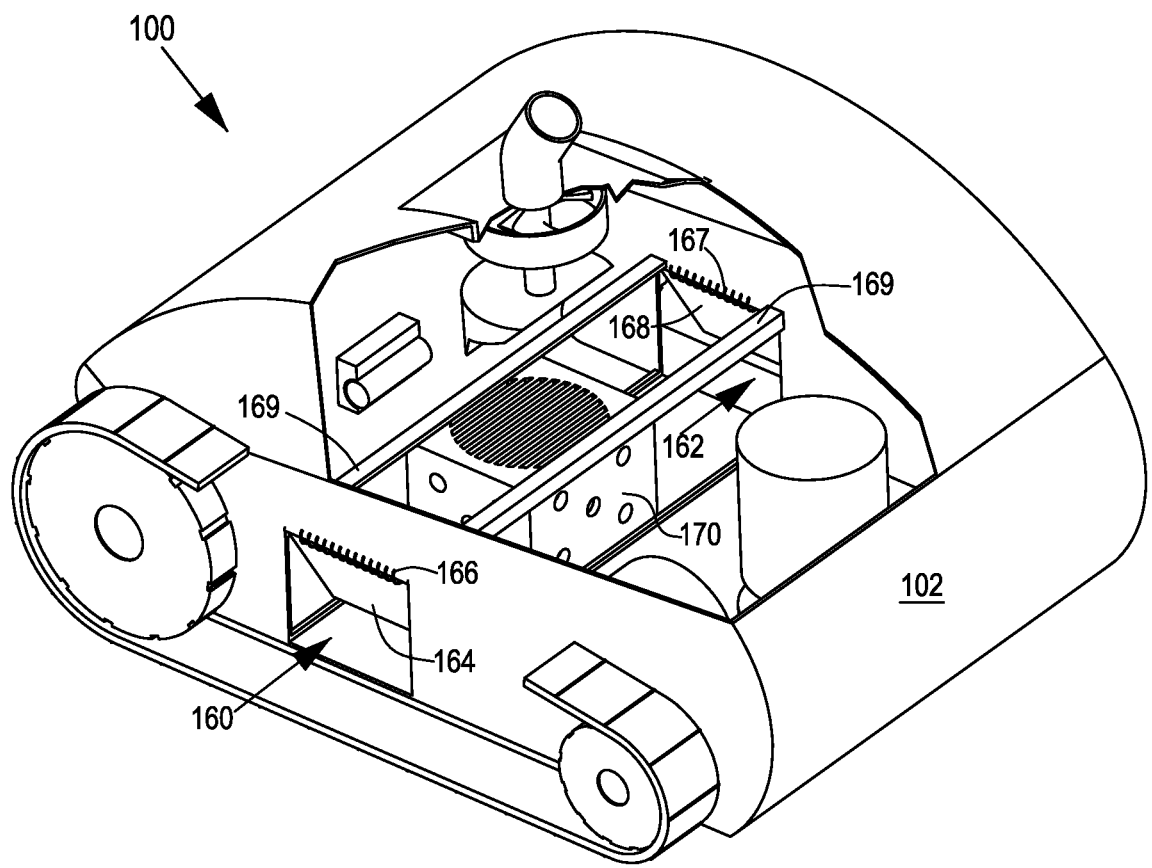
FIG. 5C illustrates a pool cleaning robot that includes a filter according to an embodiment of the invention.

FIG. 5A illustrates a pool cleaning robot 100 that includes multiple filters 170, 172 and 174 according to an embodiment of the invention. FIG. 5B illustrates a bottom of a housing 104 of a pool cleaning robot 100 that includes multiple filters according to an embodiment of the invention. FIG. 5C illustrates a pool cleaning robot 100 that includes a single filter 170 according to an embodiment of the invention.

Filter 172 may be used to filter the fluid that passes through the pool cleaning robot 100—as may be regarded as being in a filtering position. The fluid may enter through fluid opening 117 (see FIG. 5B).

Filters 172 and 174 may be regarded as being in a non-filtering position.

Alternatively—more than one of the filters 170, 172 and 174 can be used for concurrently filtering fluid that passes through the pool cleaning robot 100.

Alternatively—filter 170 or filter 174 can be used for filtering while filter 172 is not be used for filtering—when positioned at the center of the pool cleaning robot 100.

Filters 170, 172 and 174 may be inserted through a first filter opening 160 formed in the housing of the pool cleaning robot 100.

Filters 170, 172 and 174 may be ejected (outputted) from the pool cleaning robot through the first filter opening 160 or (As illustrated in FIGS. 5A and 5C)—through a second filter opening (denoted 162 formed in the housing of the pool cleaning robot 100).

Between insertion and ejection the filters of FIGS. 5A and 5C follow a linear path (delimited by rails 169) that is normal to the longitudinal axis of the pool cleaning robot. It is noted that other paths (non-linear, other linear paths) can be provided.

Filter openings may be positioned in various locations of the housing—including the bottom of the housing, the upper portion of the housing or any side portions (sidewalls) of the housing. FIGS. 5A-5C merely illustrates a non-limiting of the locations of such filter openings.

FIG. 5A also illustrates a sanitizing unit 72 that is arranged to irradiate a filter with ultraviolet radiation or perform any other sanitizing process.

Referring to FIG. 5C—first filter opening 160 is equipped with a first door 164 and a spring mechanism 166 that allows the first door 164 to open when a filter is inserted to the pool cleaning robot 100 and to be closed (thereby closing the first filter opening 160) after the filter is inserted.

Second filter opening 162 is equipped with a second door 168 and a spring mechanism 169 that allows the second door 168 to open when a filter is extracted/ejected/outputted from the pool cleaning robot 100 and to be closed (thereby closing the second filter opening 162) after the filter is extracted/ejected/outputted.

It is noted that a filter opening can be closed by the filter (or by the filter housing)—as illustrated in FIG. 5A.

Figure 6A:
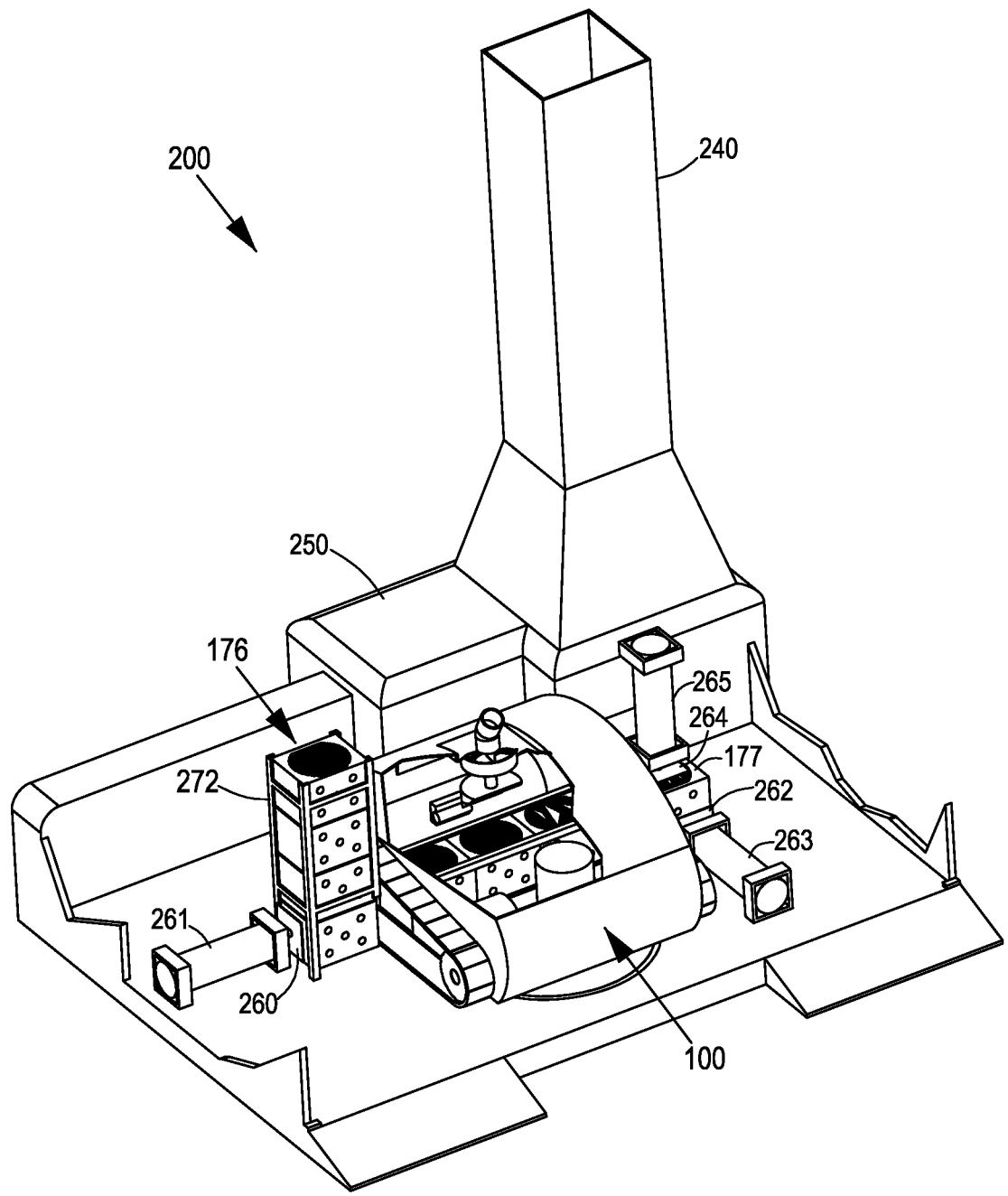
FIG. 6A illustrates a pool cleaning robot, an underwater station and multiple filters according to an embodiment of the invention.
Figure 6B:
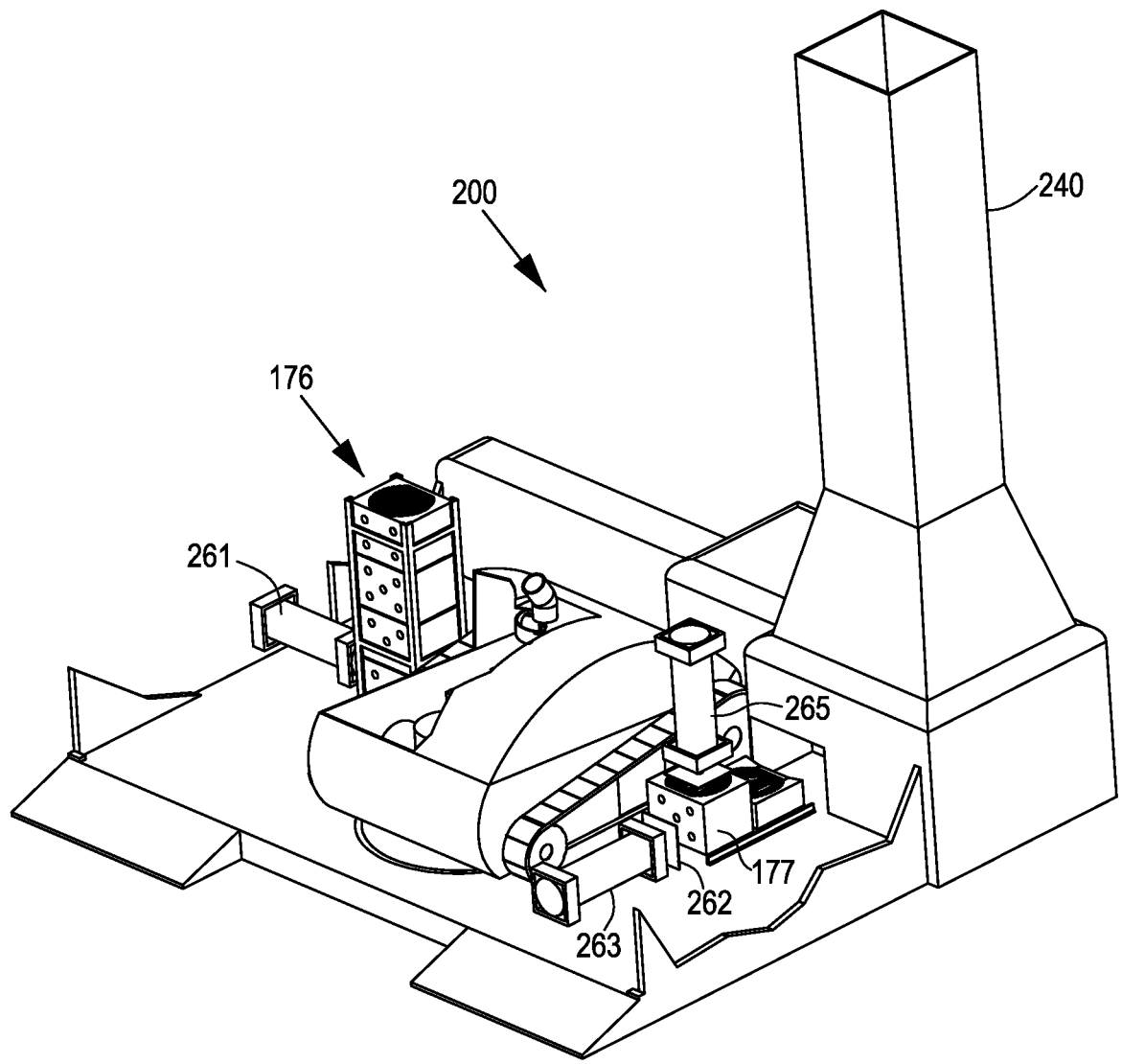
FIG. 6B illustrates a pool cleaning robot, an underwater station and multiple filters according to an embodiment of the invention.

FIGS. 6A and 6B illustrates a pool cleaning robot 100, an underwater station 200 and multiple filters 176 and 177 according to an embodiment of the invention.

The pool cleaning robot 100 is mounted on the underwater station 200. Filters 176 are stored in a first filter storage module 272 and then fed to the pool cleaning robot 100 by a first filter manipulator that is represented by arm 261. Filters are ejected from the pool cleaning robot 100 by the first filter manipulator (if the same movement used for inserting filters can also eject filters) or by a second filter manipulator that is represented by arm 263 that pushes used filters into underwater station housing 250.

FIGS. 6A and 6B also illustrate a compressor (represented by arm 265) that compresses a used filter before the used filter enters underwater station housing 250.

The underwater station 200 is further illustrated as including underwater station housing 250 and filter ejection module 240 from which used filters can be ejected or otherwise taken outside the pool.

The underwater station 200 is illustrated as including a duct 240 through which used filters can float, ejected or taken outside the pool.

The underwater station 200 may include processing elements located within the housing 250 (or outside the housing) for sanitizing, shredding, compressing, and/or attaching floating elements to used filters.

Figure 7A:
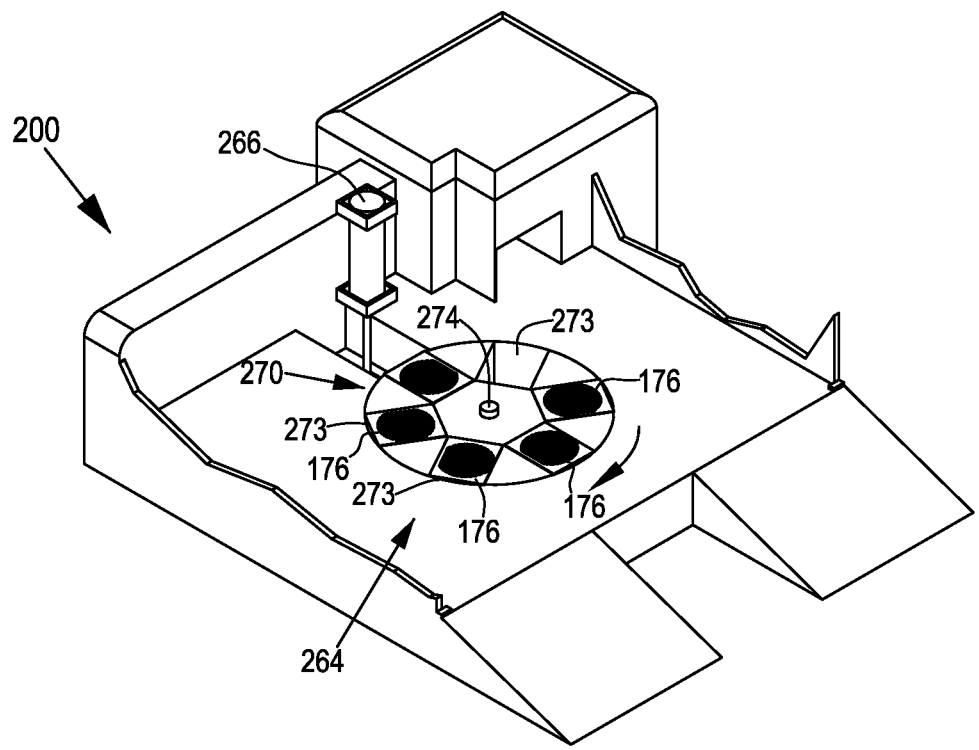
FIG. 7A illustrates an underwater station that comprises a filter manipulator according to an embodiment of the invention.
Figure 7B:
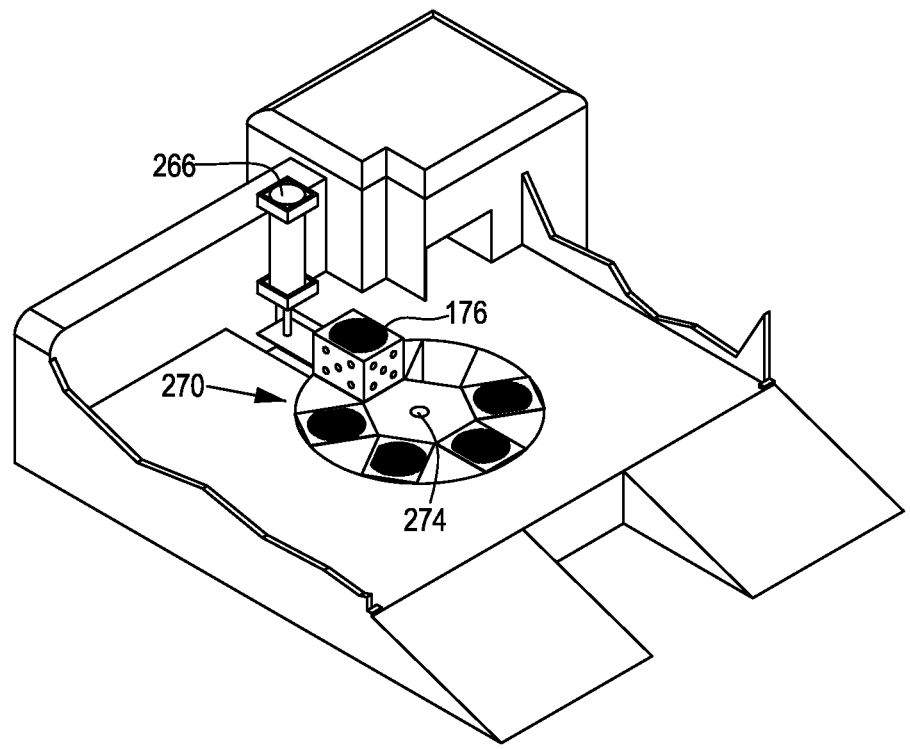
FIG. 7B illustrates an underwater station that comprises a filter manipulator that elevates a filter to be inserted into a pool cleaning robot according to an embodiment of the invention.
Figure 7C:
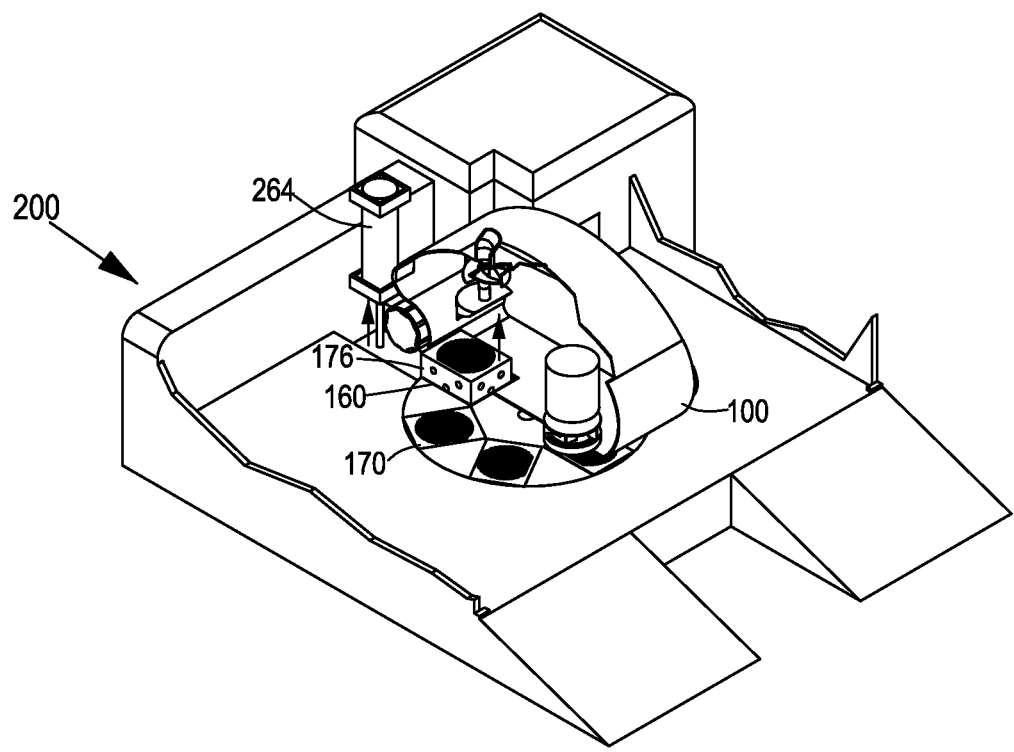
FIG. 7C illustrates an underwater station that comprises a filter manipulator and pool cleaning robot that is positioned on a platform of the underwater station and is fed by a filter according to an embodiment of the invention.
Figure 7D:
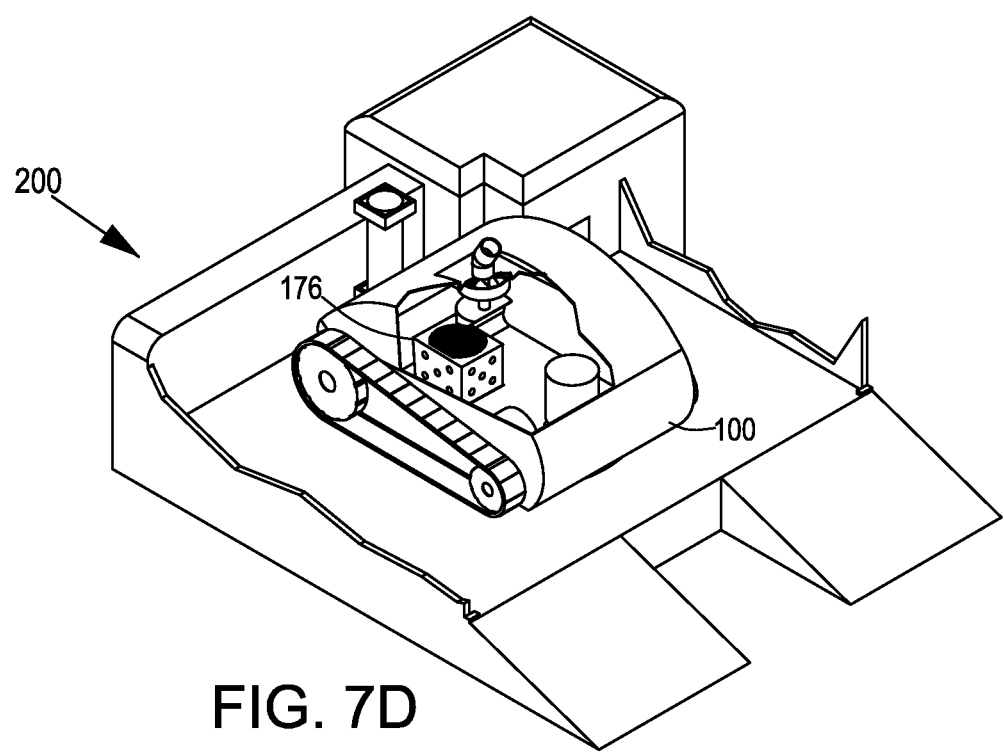
FIG. 7D illustrates an underwater station that comprises a filter manipulator and pool cleaning robot that is positioned on a platform of the underwater station after being fed by a filter according to an embodiment of the invention.

FIG. 7A-7D illustrate an underwater station 200 during various stages of a loading process of a filter into a pool cleaning robot 100 according to an embodiment of the invention. FIGS. 7C and 7D also illustrate the pool cleaning robot 100 that is being loaded with a filter.

The underwater station 200 includes a filter manipulator that includes an arm 266 for elevating a filter from a filter storage module 270 that may have a radially symmetrical shape (annular, cylindrical and the like) that has multiple compartments 273 for storing multiple filters 176. The filter storage module 270 is rotated about its center by a movement module that has an axel denoted 274 for rotating the filter storage module 270 about its axis—thereby selecting a selected filter to be inserted to the pool cleaning robot 100 via an opening formed at the bottom of the housing of the pool cleaning robot. The selected filter is positioned in proximity to arm 266 in order to allow arm 266 to elevate the filter into the pool cleaning robot 100. FIG. 7A illustrates a positioning of a selected filter near arm 266. FIGS. 7B-7C illustrates phases in the lifting process and FIG. 7D shows the end of the lifting process.

An opposite process may be used to extract a used filter from the pool cleaning robot 100—the arm 266 contacts the filter and lowers it to an empty compartment of the filter storage module 270.

Figure 8:
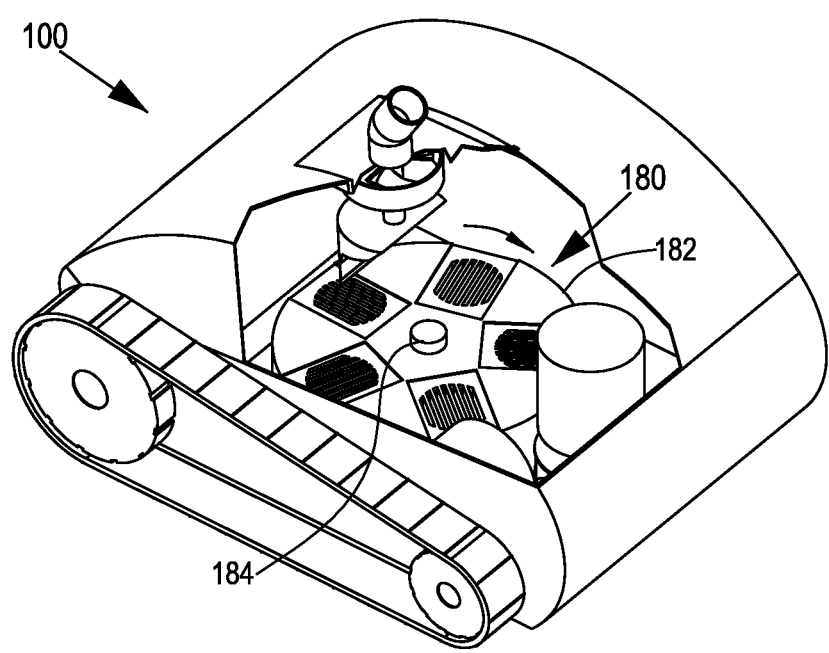
FIG. 8 illustrates a pool cleaning robot that comprises a filter according to an embodiment of the invention.

FIG. 8 illustrates a pool cleaning robot 100 that comprises a filter manipulator 180 and multiple filters according to an embodiment of the invention.

The filter manipulator 180 includes a filter storage module 182 that has multiple compartments for storing multiple filters. The filter storage module 182 may be have a radially symmetrical shape (annular, cylindrical and the like) and is rotated about its center by a movement module that has an axel denoted 184 for rotating the filter storage module 180 about its axis—thereby placing a selected filter in a filtering position.

The entire filter storage module 182 can be manually or automatically replaced. The latter can be executed by an underwater station or by the pool cleaning robot itself.

Filter Having a Rotatable Core

According to various embodiments of the invention there are provided filters that have filter cores that are rotatable. The rotation may introduce a centrifugal force that pushes compresses dirt towards the exterior of the filter and/or towards filtering elements of the filter and improves the filtering process.

Figure 9:
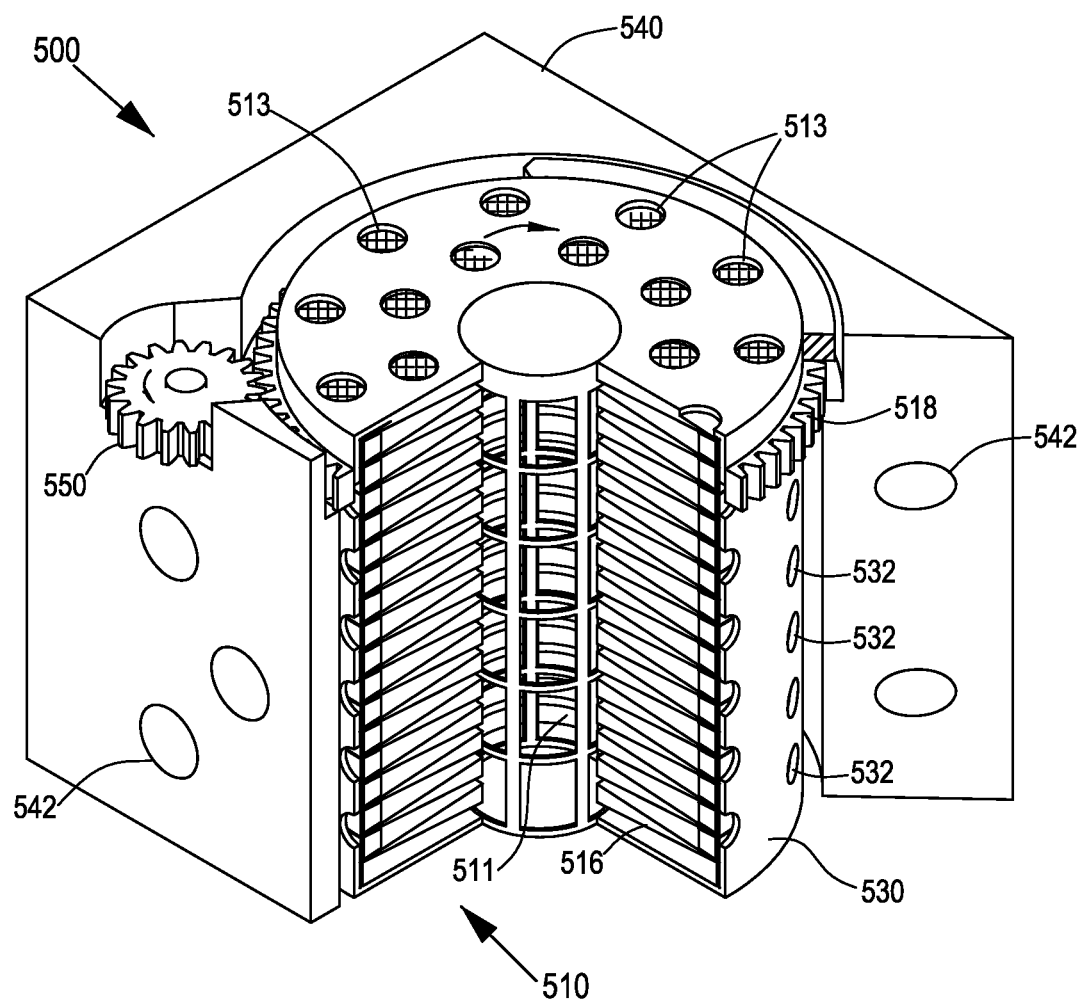
FIG. 9 illustrates a filter having a filter core with a zigzag shaped array of filtering elements, a perforated pole and a gear that assist in rotating a core of the filter according to an embodiment of the invention.

FIG. 9 illustrates a filter 500 that includes a filter core 510, a filter core enclosure 530 and filter housing 540.

It is noted that in various figures (for example FIGS. 9, 10, 12, 13A, 13B, 14, 15, 16A, 16B) there is illustrated a gap between the filter enclosure 530 and the filter housing 540. Such a gap may not exist or otherwise fluid can be prevented from passing through the gap unfiltered and enter various parts of the pool cleaning robot.

The filter core 510 is at least partially located within the filter housing 540 and includes one or more inlets 511, one or more outlets 513 and at least one filtering element (such as the zigzag array of filtering elements 516) that is positioned between the one or more inlets 511 and the an one or more outlets 513. The filter core enclosure 530 includes openings 532 that facilitate a flow of fluid to and from the filter core 510.

The filter core enclosure 530 includes a gear 518 that meshes with another gear 550. The other gear may be rotatably connected to the filter housing 540 and is rotated by a filter core rotator (denoted 552 in FIG. 11B).

The filter housing 540 includes filter housing openings 542 that facilitates a flow of fluid to and from the filter core enclosure 530.

FIG. 9 illustrates a cylindrical shaped filter core enclosure and a filter housing having a cylindrical interior and a rectangular shaped exterior. The filter core 510, the filter enclosure 530 and the filter housing 540 can be of different shapes.

FIG. 9 also illustrated a perforated pole 560 that is located at the center of the filter core 510. The perforated pole 560 can be regarded as belonging to filter 500 or as not belonging to the filter 500. The perforated pole 560 can be attached to the filter 500 in a detachable or non-detachable manner. For example an actuator and a spring may be provided for detaching or locking the filter.

Figure 10:
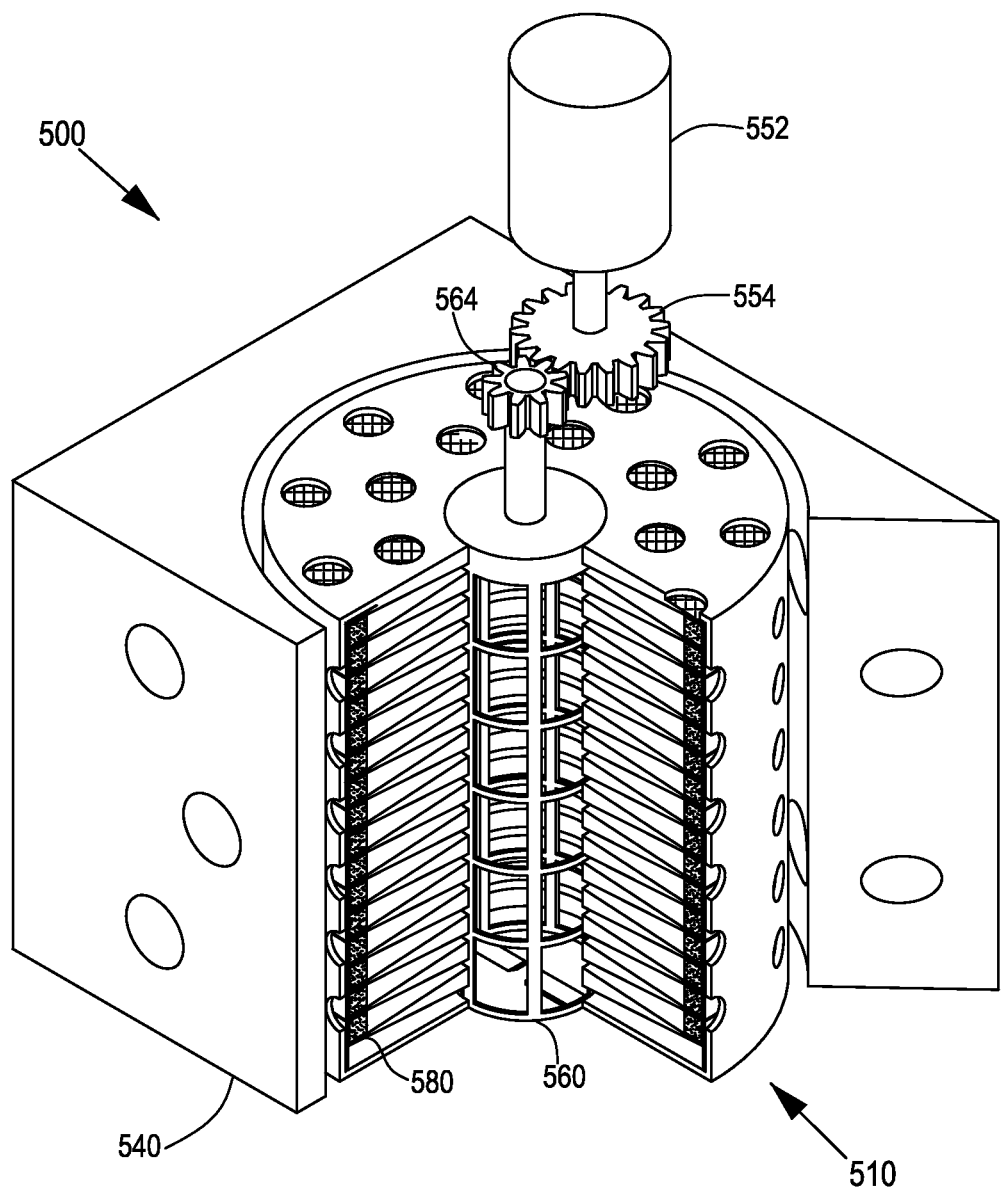
FIG. 10 illustrates a filter a filter core with zigzag shaped array of filtering elements, a gear and a perforated pole that assist in rotating the filter and a filter core rotator according to an embodiment of the invention.

FIG. 10 illustrates filter 500 as having (or being connected to) a perforated pole 560 that is connected to axel 562 that has a gear 564 at its top. Gear 564 is rotated by another gear 554 connected to filter core rotator 552. In FIG. 10 the filter housing 540 is not connected to gear 550 and the filter enclosure 530 does not include a gear.

Figure 11A:
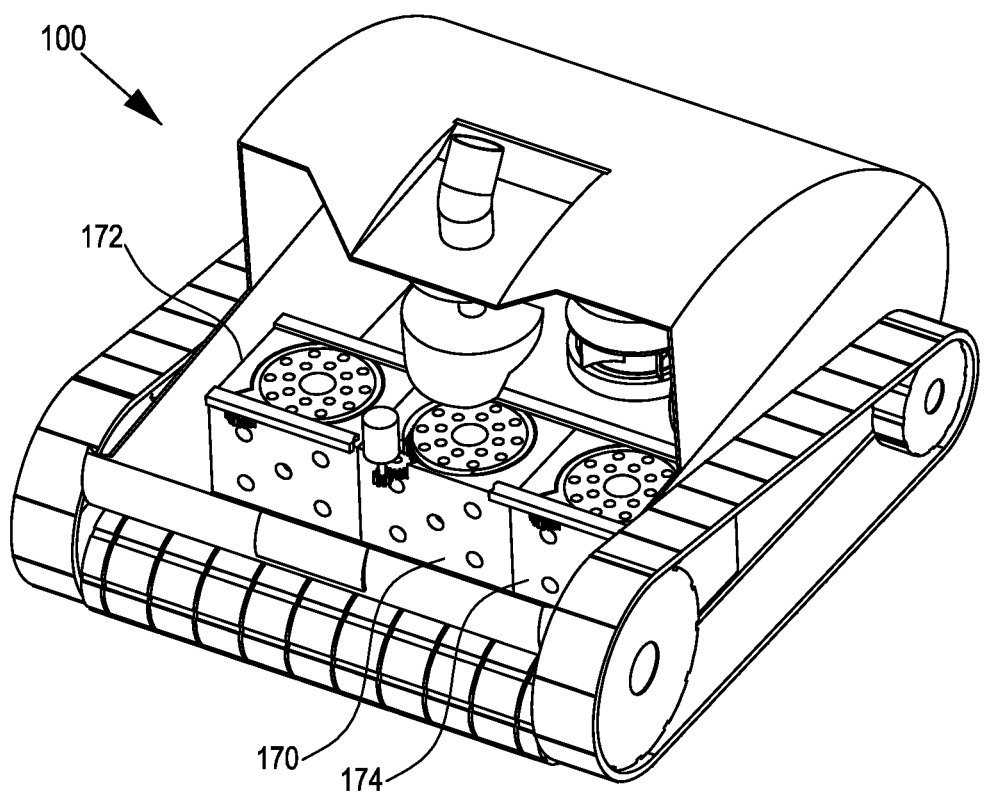
FIG. 11A illustrates a pool cleaning robot that includes multiple filters, a gear and a filter core rotator according to an embodiment of the invention.
Figure 11B:
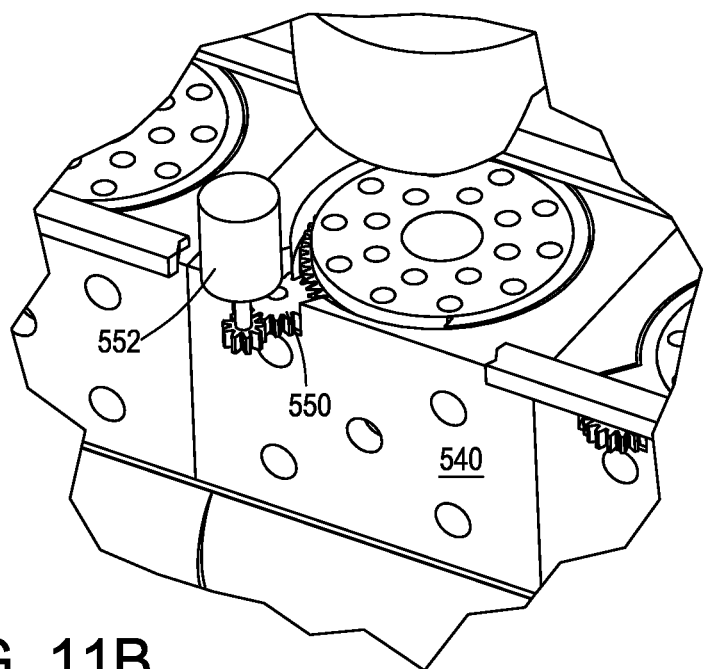
FIG. 11B illustrates multiple filters positioned within a pool cleaning robot, a gear and a filter core rotator according to an embodiment of the invention.

FIGS. 11A and 11B illustrate a pool cleaning robot 100 that includes multiple filters 170, 172 and 174, a gear 550 of filter 172 that is positioned in a filtering position and is rotated by filter core rotator 552 according to an embodiment of the invention.

Figure 12:
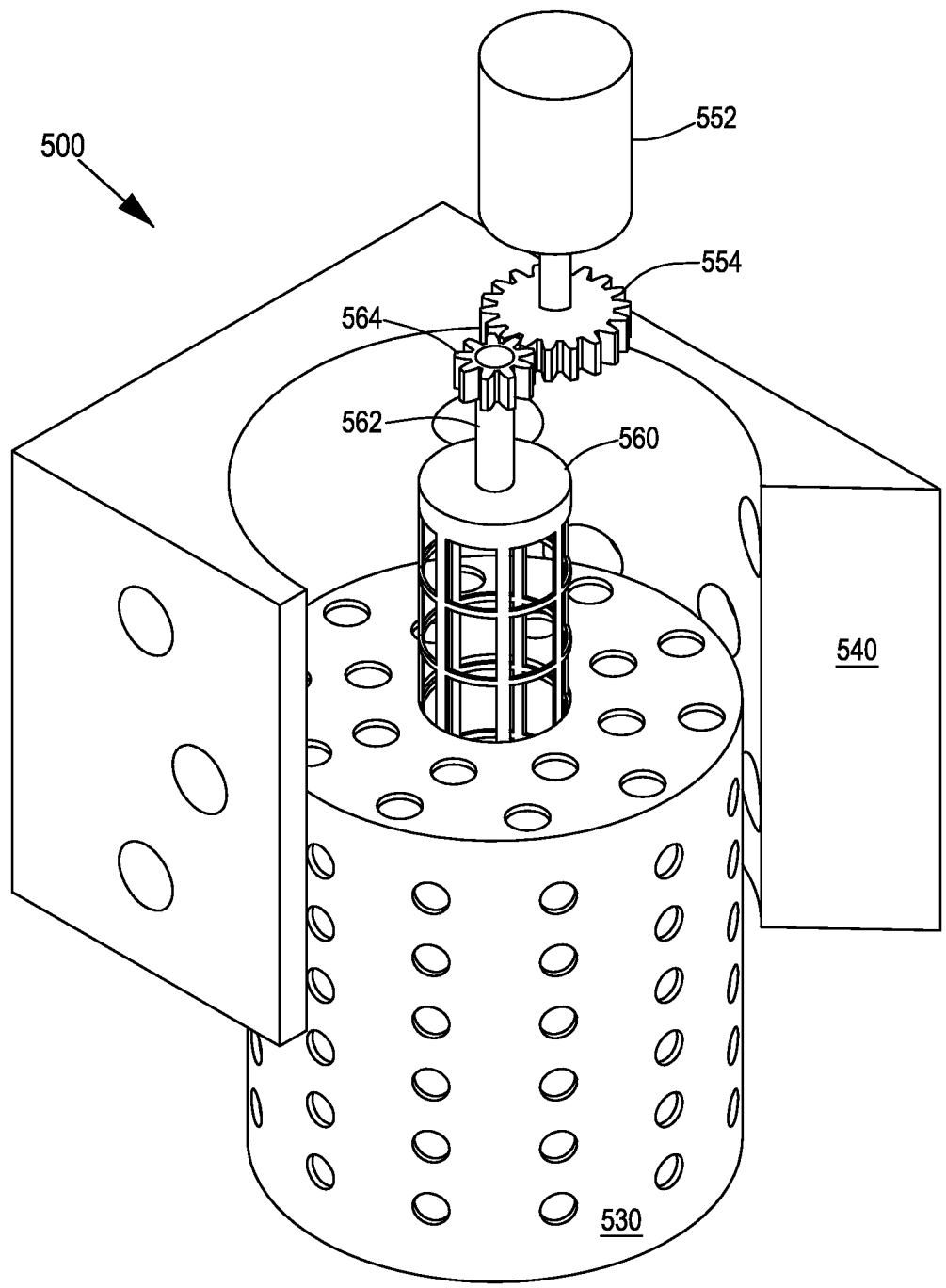
FIG. 12 illustrates a filter, a gear and a perforated pole, a filter core rotator while the filter core is being inserted to (or extracted from) the filter housing according to an embodiment of the invention.

FIG. 12 illustrates filter 500 as having (or being connected to) a perforated pole 560 that is connected to axel 562 that has a gear 564 at its top. Gear 564 is rotated by another gear 554 connected to filter core rotator 552. The filter core rotator 552 may be a pump motor, a drive motor or be mechanically coupled to one of these motors.

Figure 13A:
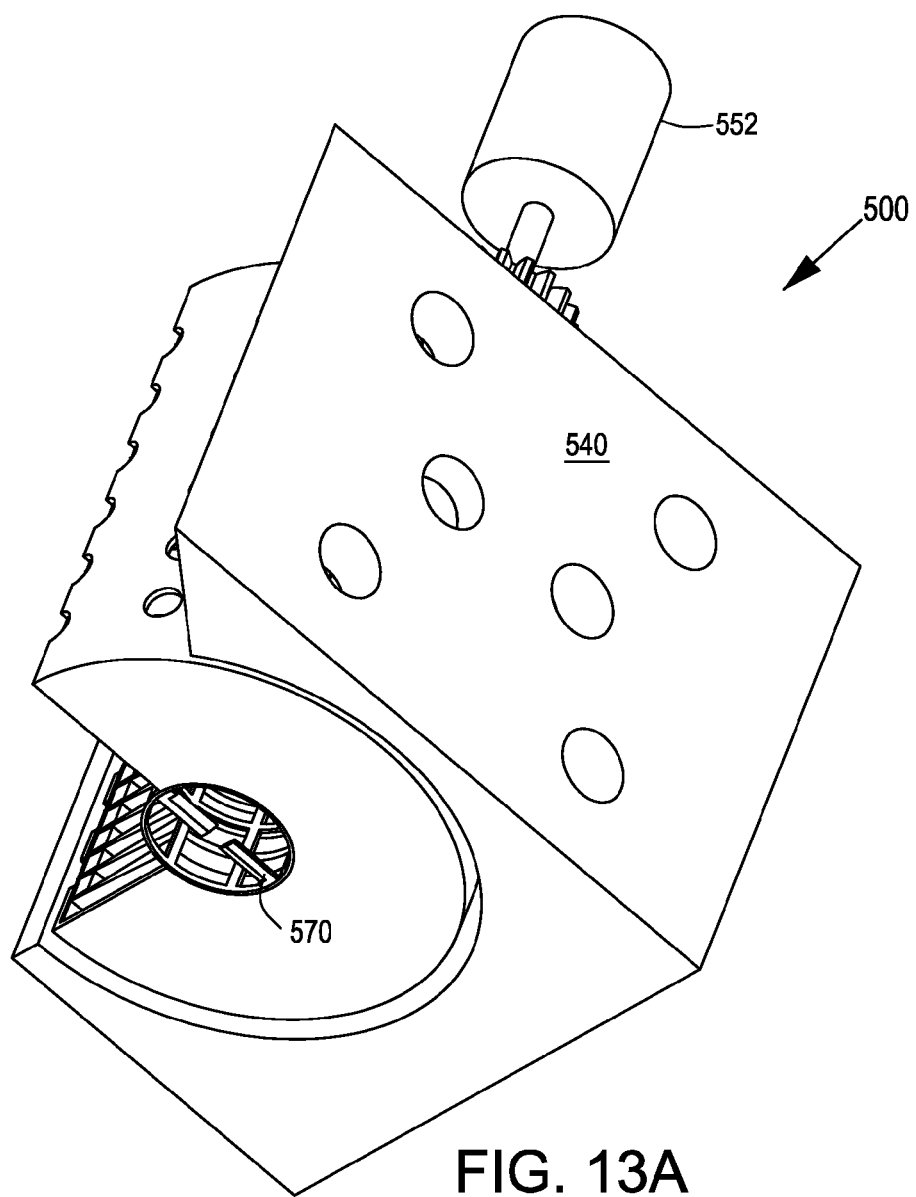
FIG. 13A illustrates a filter, a gear, a perforated pole, choppers, and a filter core rotator according to an embodiment of the invention.
Figure 13B:
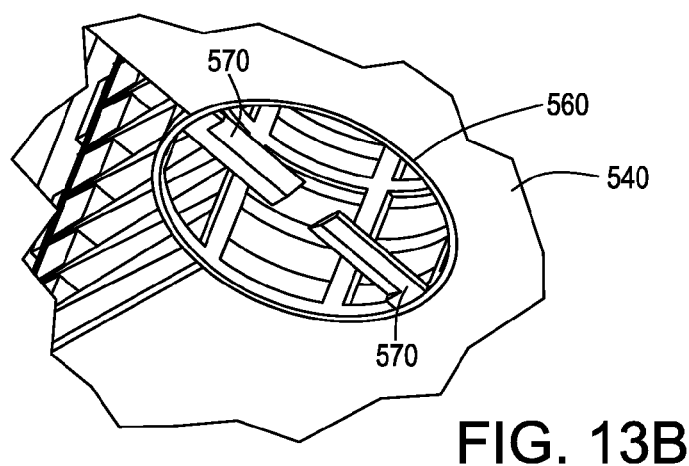
FIG. 13B illustrates a bottom of the perforated pole and choppers according to an embodiment of the invention.

The filter core 510 can be inserted to (or extracted from) the filter housing 540. The filter housing 540 can be part of the filter and/or can be a part of the pool cleaning robot FIG. 13A illustrates a filter 500, a gear 550, a perforated pole 560, choppers 570, and a filter core rotator 552 according to an embodiment of the invention. FIG. 13B illustrates an area of filter 510 that includes choppers 570. The choppers 570 are connected to an input of the perforated pole 570 so then when the perforated core is rotated the choppers chop debris that enters the filter 500 via the perforated pole 560. The input of the perforated pole 560 can be positioned directly above an opening such as fluid opening 117 of FIG. 5B

Choppers 570 are shown as having fin like shape and are facing each other. There may be one or more choppers. Different choppers 570 can have different shapes and/or sizes.

The choppers can be connected to the filter core or other parts of the filter. Choppers can be positioned at different heights of the perforated pole or filter.

The choppers may be attached as propellers to axle 558.

Figure 14:
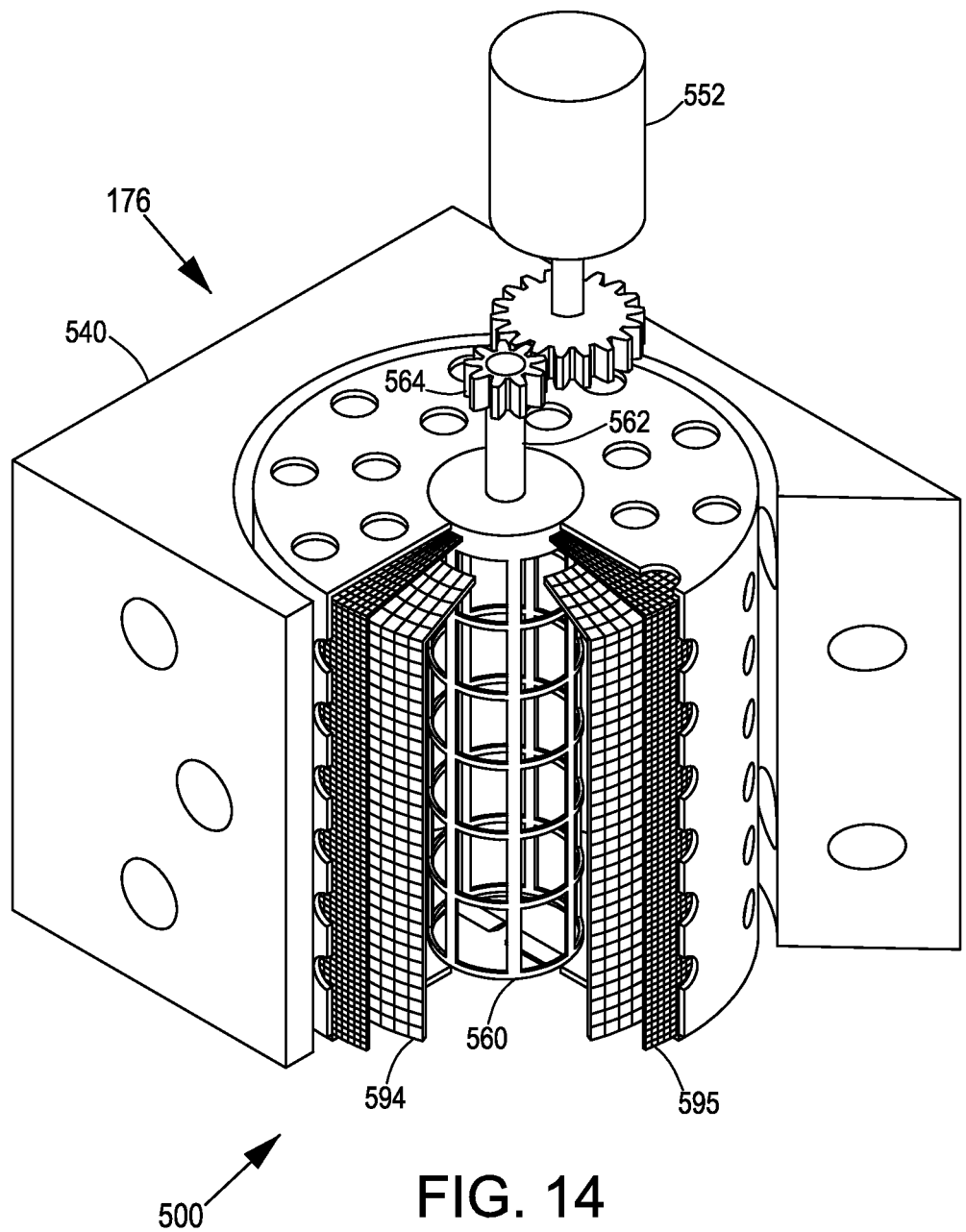
FIG. 14 illustrates a filter having a filter core that includes a fine filtering element and a coarse filtering element, a gear, a perforated pole, and a filter core rotator according to an embodiment of the invention.

FIG. 14 illustrates filter 500 as having (or being connected to) a perforated pole 560 that is connected to axel 562 that has a gear 564 at its top. Gear 564 is rotated by another gear 554 connected to filter core rotator 552. The filter core 510 includes filtering elements that are a fine filter element 595 and a coarse (or gross) filtering element 594 both are illustrated as being a cylindrical shaped meshes. Fluid from the one or more inlets of the filter are filtered by the gross filtering element 594 before being filtered by the fine filtering element 595. The gross and fine filtering elements by differ from each other by the size of particles they block. The gross filtering mesh may be constructed of 200 microns pore size and the fine mesh may be of 50 microns pore size. Other pore sizes can be provided.

Figure 15:
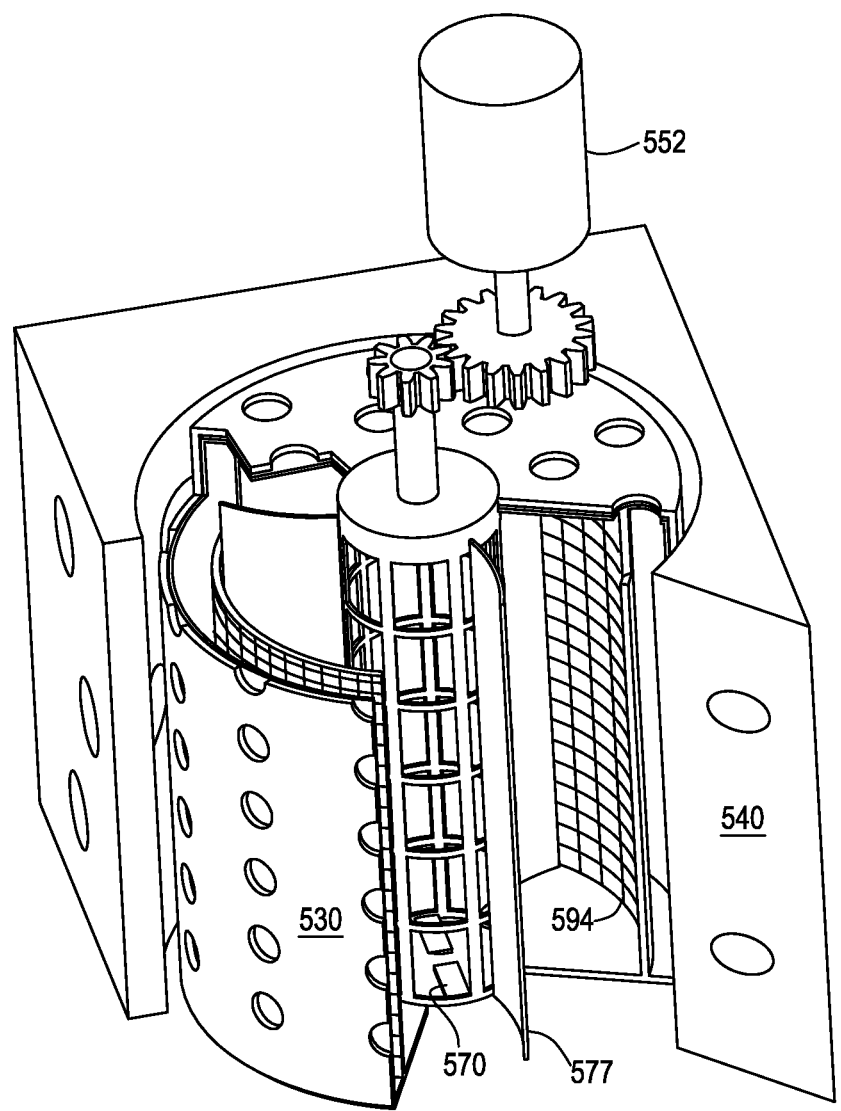
FIG. 15 illustrates a filter having a filter core that includes a filtering element and blades , a gear, a perforated pole, choppers and a filter core rotator according to an embodiment of the invention.

FIG. 15 illustrates filter 500 as having (or being connected to) a perforated pole 560 that is connected to axel 562 that has a gear 564 at its top. Gear 564 is rotated by another gear 554 connected to filter core rotator 552. The filter 500 includes blades 577 that may be connected to various other parts of the filter 510. Additionally or alternatively the blades 577 are connected to an inner cylindrical frame (not shown) that may be parallel to the perforated pole 560, may contact the perforated pole 560, may be spaced apart from the perforated pole 560, may be connected to and/or held by the filter core enclosure 530 (for example—held by the floor, bottom and/or sidewall of the filter core enclosure). When the perforated pole 560 is not connected to the blades and the filter core 510 the perforated pole 560 may remain in the pool cleaning robot after ejection of the filter core 510 and accumulated dirt can be serviced efficiently and washed off the blades. The blades 557 may extend along the entire filter enclosure 530 and are positioned between the perforated pole 560 and the filtering element 594. The blades 577 form a rotor. When the filter core 510 is rotated by filter core rotator 552 these blades may cause the filter core 510 to act as a turbine and assist the flow of water into the filter core.

Dual Mode Motor-Generator and Dual-Mode Rotor

Figure 16A:
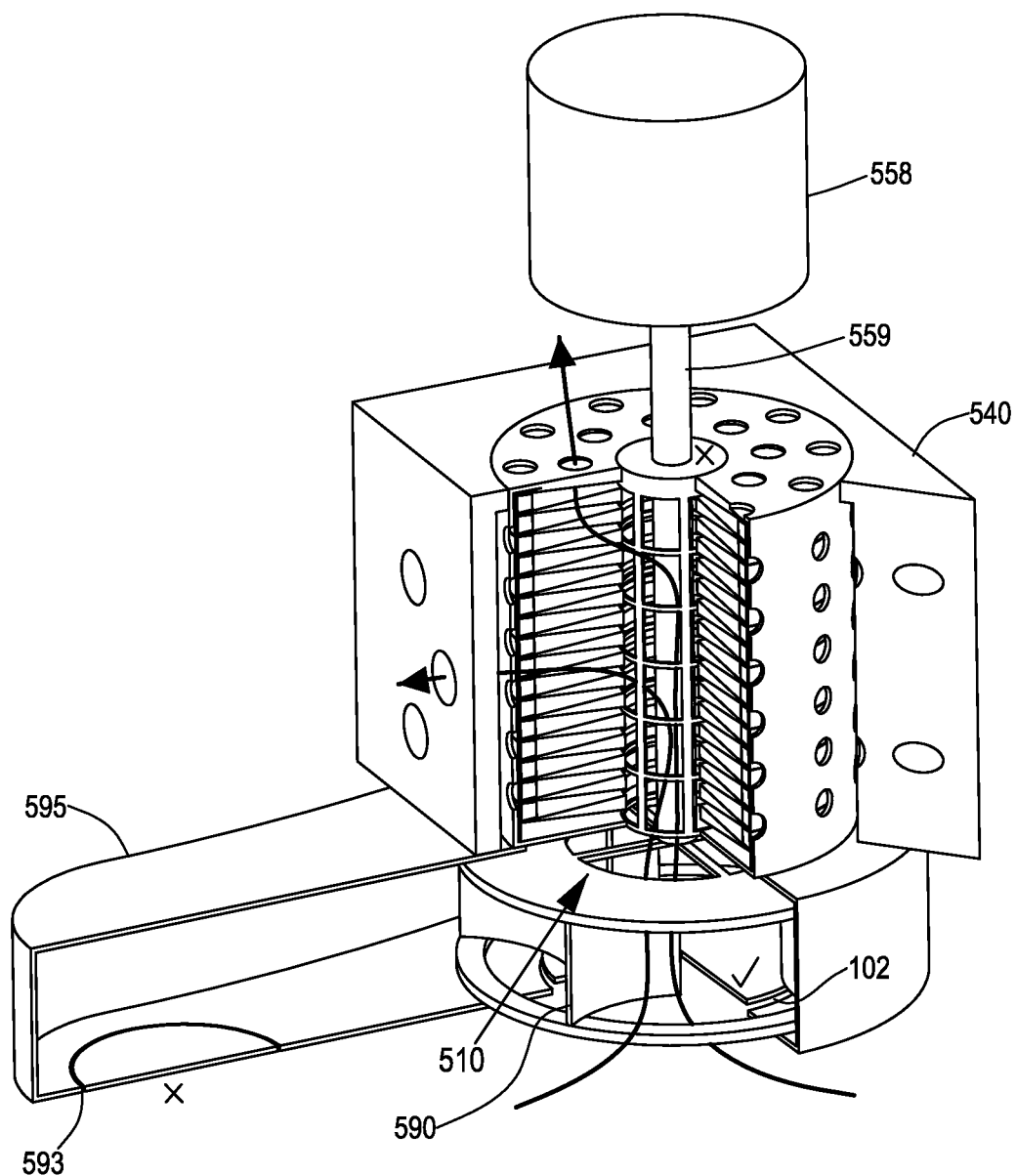
FIG. 16A illustrates a filter having a filter core that includes a zigzag shaped array of filtering elements, a perforated pole, a motor/generator that functions as a motor and acts as a filter core rotator and a turbine rotator, a rotor that acts as a turbine and is positioned below the filter and an enclosure that has a first opening below the turbine and a second opening that is selectively sealed by a uni-directional valve.
Figure 17A:
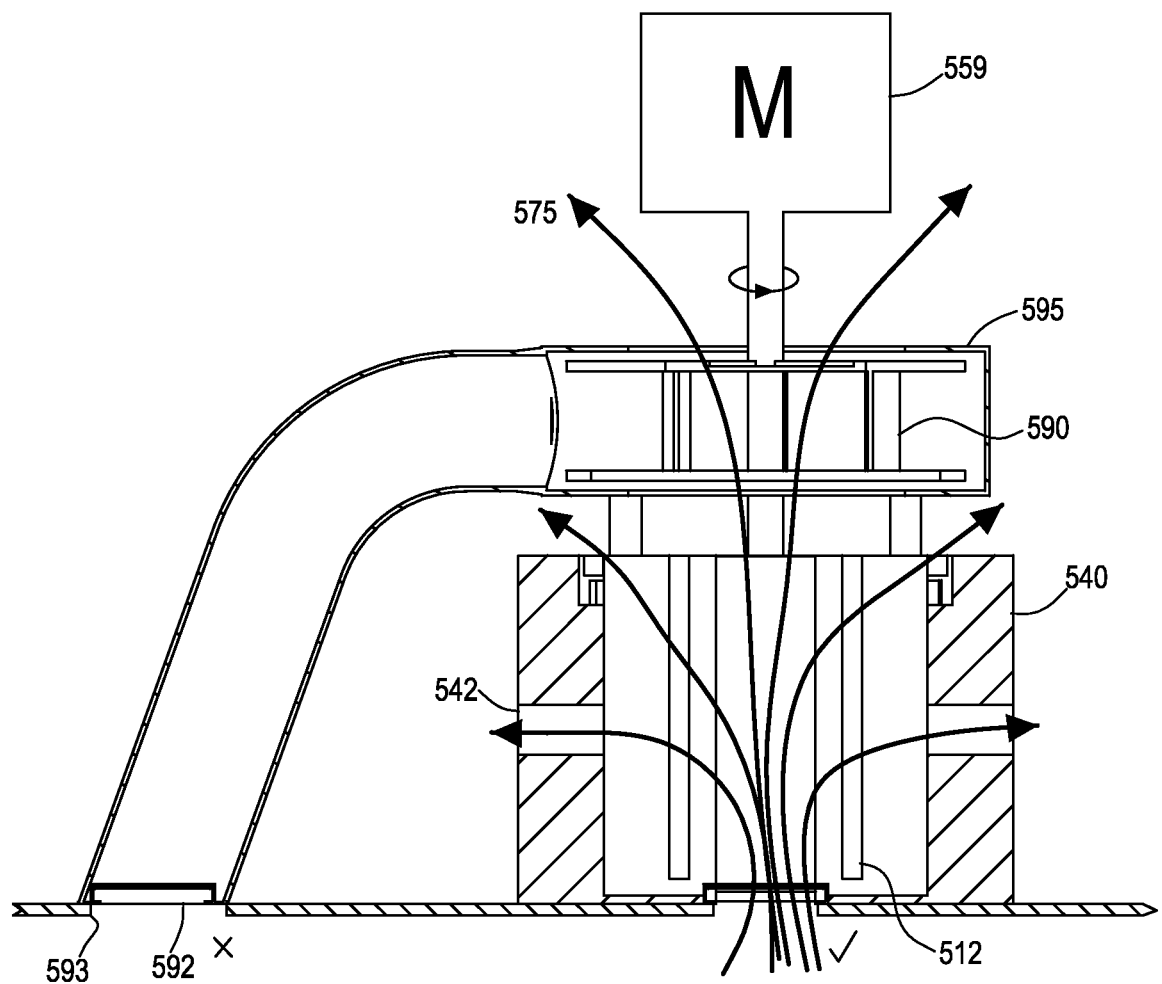
FIG. 17A is a cross sectional view of a filter having a filter core, a perforated pole, a motor/generator that functions as a motor and acts as a filter core rotator and a turbine rotator, a rotor that acts as a turbine and is positioned below the filter and an enclosure that has a first opening below the turbine and a second opening that is selectively sealed by a uni-directional valve.
Figure 17B:
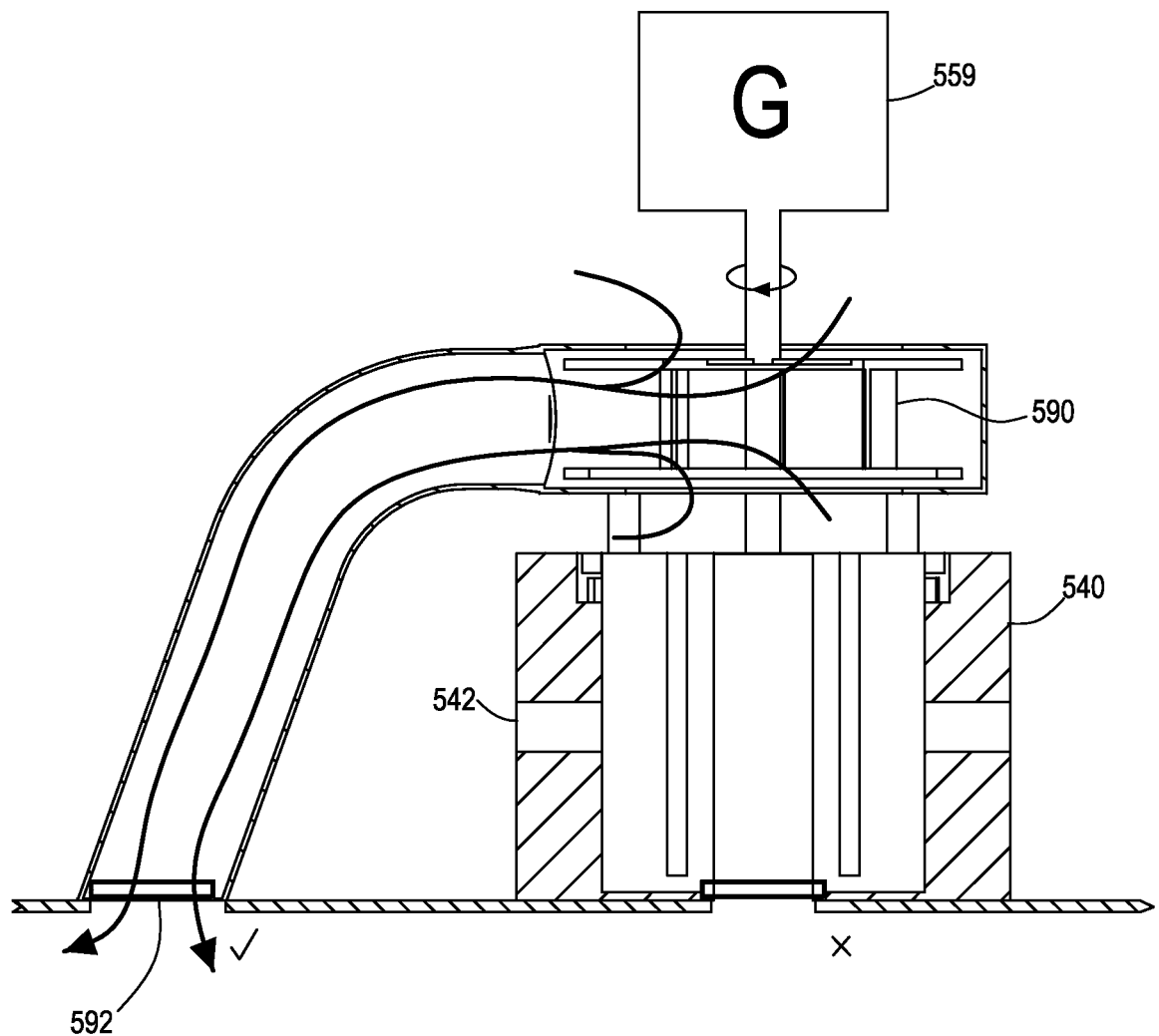
FIG. 17B is a cross sectional view of a filter having a filter core , a perforated pole, a motor/generator that functions as a generator, a rotor that acts as an impeller and is positioned below the filter and an enclosure that has a first opening below the turbine and a second opening that is selectively sealed by a uni-directional valve.
Figure 17C:
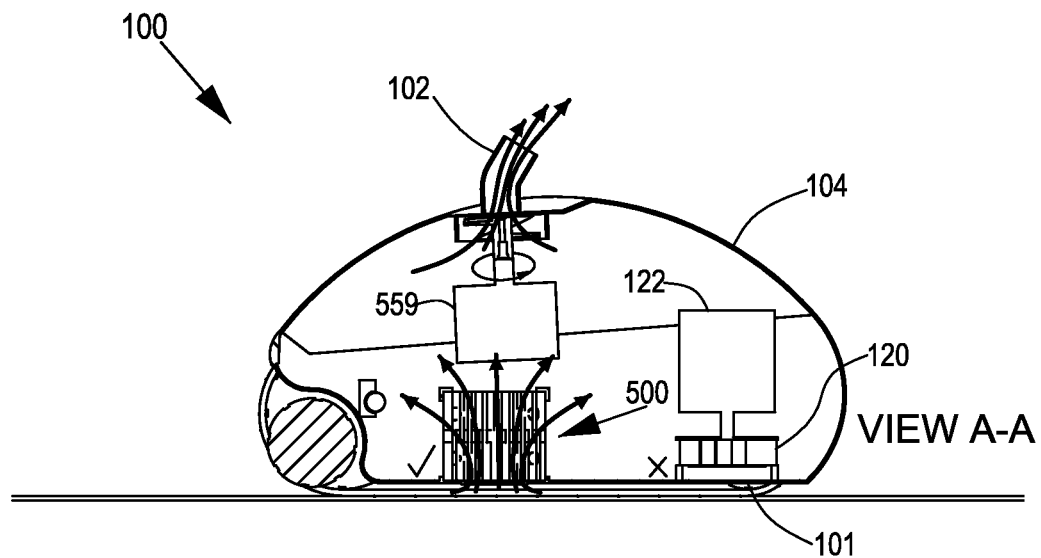
FIG. 17C is a cross sectional view of a pool cleaning robot according to an embodiment of the invention.
Figure 17D:
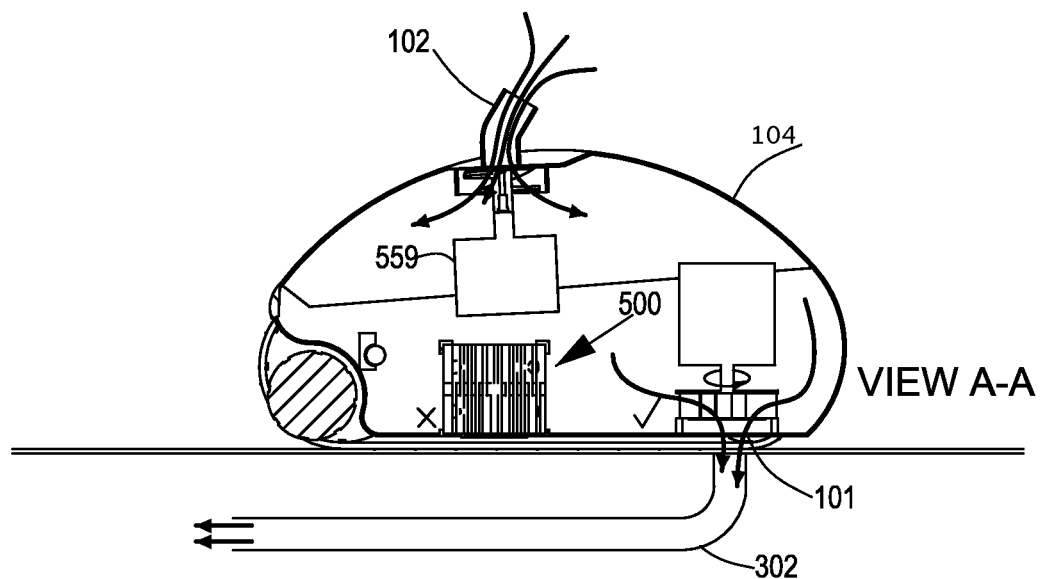
FIG. 17D is a cross sectional view of a pool cleaning robot according to an embodiment of the invention.
Figure 17E:
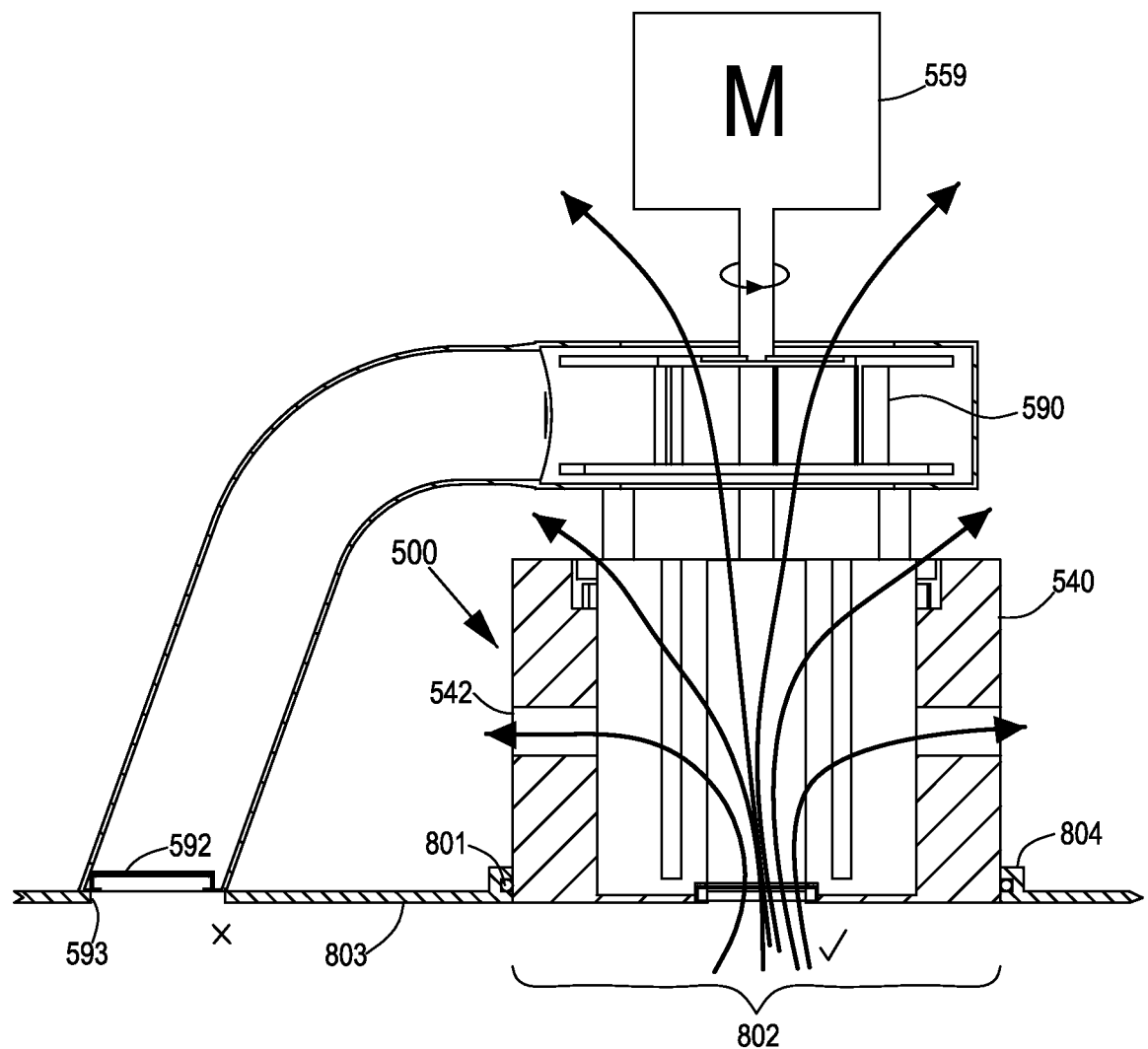
FIG. 17E is a cross sectional view of a filter having a filter core, a perforated pole, a motor/generator that functions as a motor and acts as a filter core rotator and a turbine rotator, a rotor that acts as a turbine and is positioned above the filter and an enclosure that has a first opening below the turbine and a second opening that is selectively sealed by a uni-directional valve.

FIGS. 16A, 17A and 17E illustrate a filter 500, a rotor 590 that functions as an impeller, a motor/generator 559 that functions as a motor for rotating the filter core 510 and the rotor 590, and an enclosure 595 not shown that surrounds the rotor and has (a) a first opening 102 located below the rotor 590 and (b) a second opening 593 that is selectively sealed by a uni-directional valve 592, according to an embodiment of the invention. Alternatively, the first and second openings 102 and 593 may be formed in the bottom of the pool cleaning robot 100 and the enclosure 595 may be located above the bottom in a manner that the bottom and the enclosure may provide a closed environment (except the openings 102 and 593).

In FIG. 16A the filter 500 is positioned between the rotor 590 and the motor/generator 559. In FIG. 17A the rotor 590 is positioned between the filter 500 and the motor/generator 559. An axle/spindle 558 connects the motor/generator 559 to the perforated pole 560.

In this mode of operation fluid is directed by the rotor to enter the filter 500 and to exit filter 500 after being filtered. In this mode of operation the uni-directional valve 592 seals the second opening 593.

In FIG. 17E the filter 500 (or the filter 500 and the rotor 590) can be fed to the pool cleaning robot via opening 802 formed in a bottom 803 of the pool cleaning robot. Once inserted in the pool cleaning robot connecting elements (such as elastic ring 801 placed in a space formed by connecting element 804 may hold the filter 500.

Figure 16B:
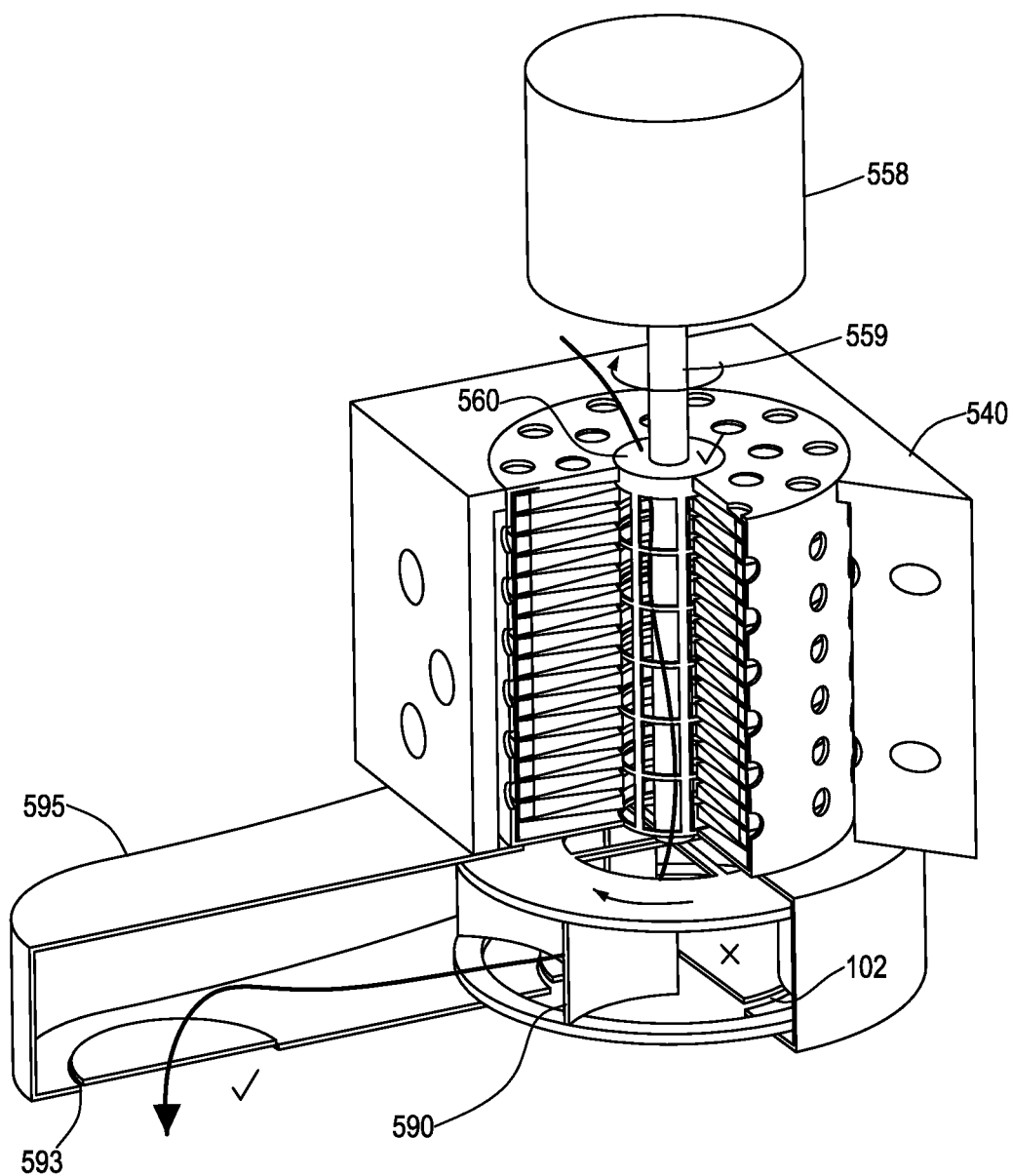
FIG. 16B illustrates a filter having a filter core that includes a zigzag shaped array of filtering elements, a perforated pole, a motor/generator that functions as a generator, a rotor that acts as an impeller and is positioned below the filter and an enclosure that has a first opening below the turbine and a second opening that is selectively sealed by a uni-directional valve.
Figure 17F:
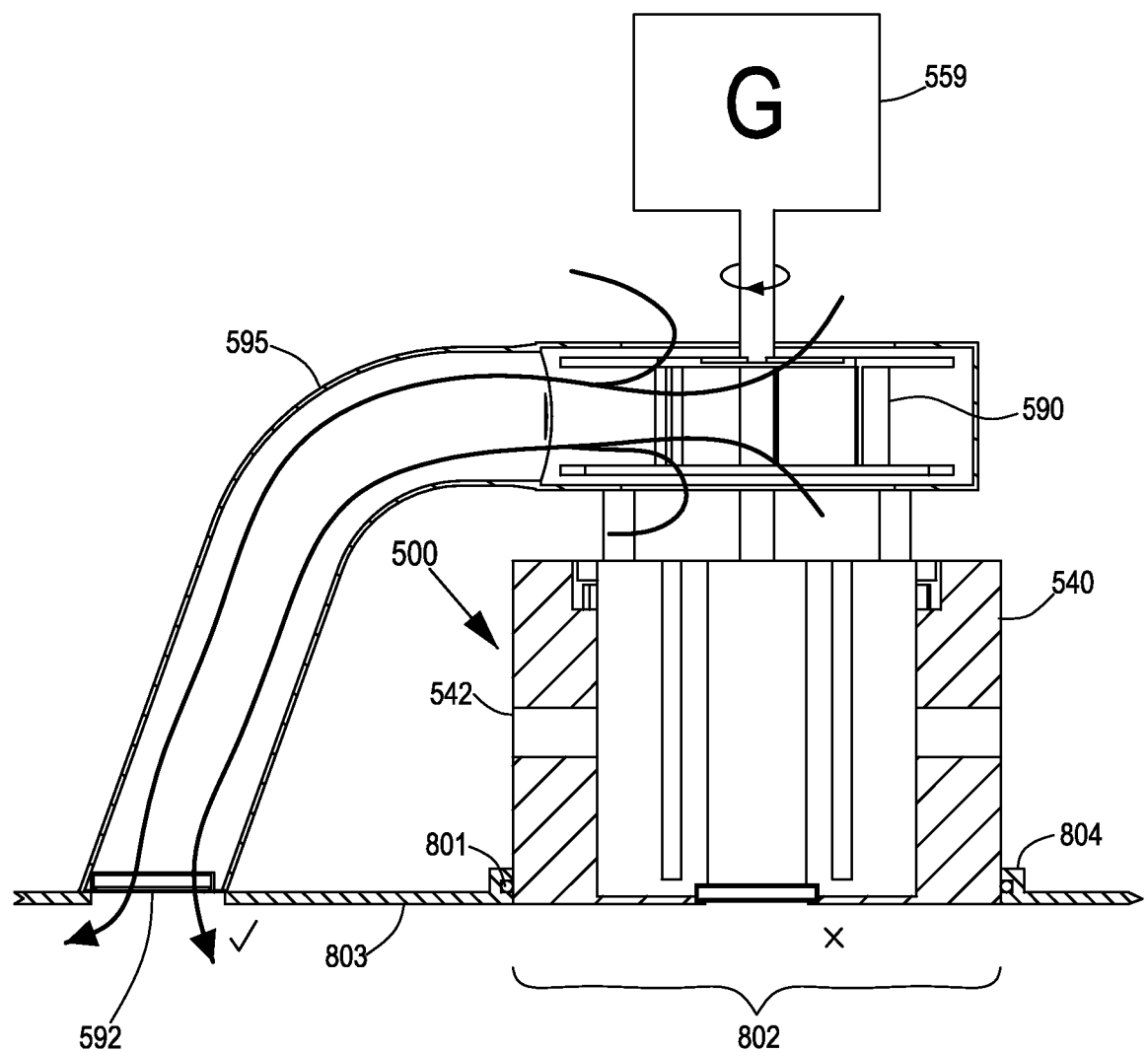
FIG. 17F is a cross sectional view of a filter having a filter core, a perforated pole, a motor/generator that functions as a generator, a rotor that acts as an impeller and is positioned above the filter and an enclosure that has a first opening below the turbine and a second opening that is selectively sealed by a uni-directional valve.

FIGS. 16B, 17B and 17F illustrate a filter 500, a rotor 590 that functions as a turbine, a motor/generator 559 that functions as a generator for generating electrical energy, and an enclosure 595 that surrounds the rotor and has a first opening 102 above the rotor 590 and a second opening 593 that is selectively sealed by a uni-directional valve 592, according to an embodiment of the invention.

Alternatively, the first and second openings 102 and 593 may be formed in the bottom of the pool cleaning robot 100 and the enclosure 595 may be located above the bottom in a manner that the bottom and the enclosure may provide a closed environment (except the openings 102 and 593).

In FIG. 16B the filter 500 is positioned between the rotor 590 and the motor/generator 559. In FIG. 17B the rotor 590 is positioned between the filter 500 and the motor/generator 559.

In this mode fluid is sucked (for example by a drain of a pool) through second opening 593 and rotates the rotor 590 that in turn rotates motor/generator 599. The uni-directional valve 592 is open.

In FIG. 17F the filter 500 (or the filter 500 and the rotor 590) can be fed to the pool cleaning robot via opening 802 formed in a bottom 803 of the pool cleaning robot. Once inserted in the pool cleaning robot connecting elements (such as elastic ring 801 placed in a space formed by connecting element 804 may hold the filter 500.

FIG. 17C is a cross sectional view of pool cleaning robot 100 according to an embodiment of the invention. The pool cleaning robot 100 includes housing 104 filter 500, a rotor 590 that functions as an impeller, a motor/generator 559 that functions as a motor for rotating the filter core (part of filter 500) and the rotor 590, electrical generator 122 and turbine 120 that are spaced apart from filter 500 and are positioned above another opening of the housing. In this mode of operation fluid is directed by the rotor 590 to enter the filter 500 and to exit filter 500 after being filtered. In this mode of operation a uni-directional valve (not shown) seals the opening below turbine 120.

FIG. 17D is a cross sectional view of pool cleaning robot 100 according to an embodiment of the invention. The pool cleaning robot 100 includes housing 104, filter 500, a rotor 590 that functions as a turbine, a motor/generator 559 that functions as an electrical generator and the rotor 590, an electrical generator 122 and turbine 120 that are spaced apart from filter 500 and are positioned above another opening of the housing. The opening below the turbine 120 is opened and fluid is sucked (for example by drain 302 of a pool) through opening 102 into the pool cleaning robot and out of the pool cleaning robot to drain 302 thereby rotating the rotor 590 that in turn rotates motor/generator 599 and rotating turbine 120.

Any one or a combination of the filter 500 and the rotor 590 of FIGS. 16A, 16B, 17A, 17B, 17C, 17D, 17E and 17F can be replaced underwater (or above the water) through openings formed in the pool cleaning robot. This is illustrated by opening 802 formed in the bottom of the housing in FIGS. 17E and 17F. The opening can be formed in sidewall of the pool cleaning robot. When any filter is provided into the pool cleaning robot (for example, any one of the filters illustrated in FIGS. 5A, 5C, 6A, 6B, 7A, 7B, 7C, 7D, 12, 17E and 17F) it can be held to its position by any known fastening or holding element known in the art such as pins, blots, stripes, rails, springs and the like. Additionally or alternatively the opening through which the filter is inserted can close or at least partially close the opening through which the filter entered. For example, after a filter has been inserted from the bottom of the pool cleaning robot, it may be fastened by vertical elements that contact the upper part of the filter, the filter opening may close, the filter can be inserted into vertical or otherwise erect rails and the like.

Figure 18A:
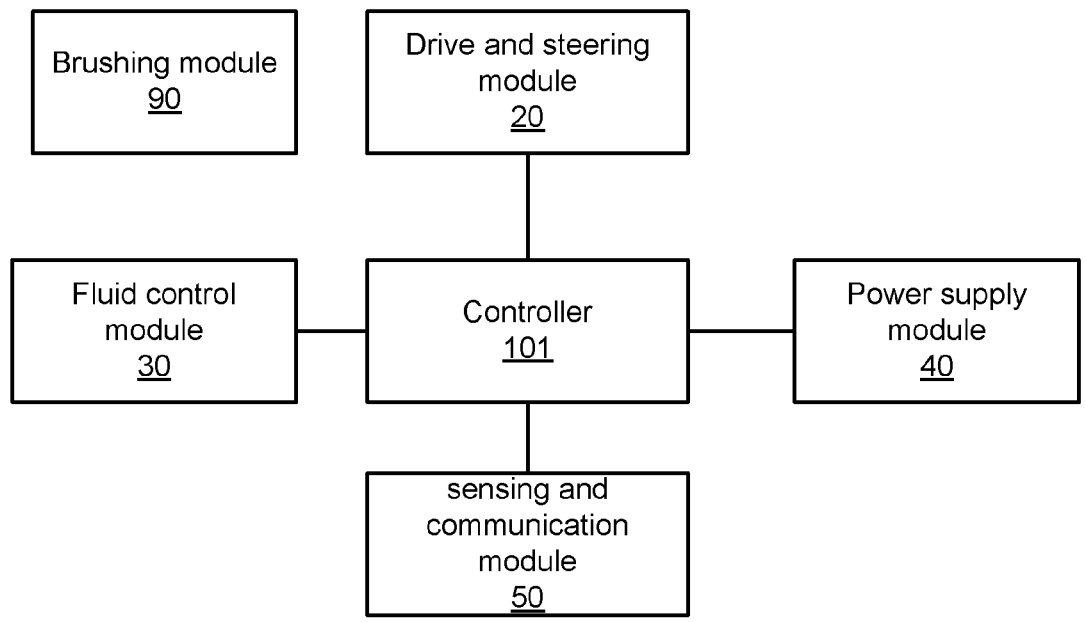
FIG. 18A illustrates various components of a pool cleaning robot according to an embodiment of the invention.

FIG. 18A illustrates various components of a pool cleaning robot 100 according to an embodiment of the invention.

The pool cleaning robot 100 is illustrated as including controller 101, drive and steering module 20, power supply module 40, fluid control module 30, sensing and communication module 50 and brushing module 90.

The controller 101 is arranged to control the operation of the pool cleaning robot 100 and especially control the various modules 20, 30, 40 and 50. For example, the controller 101 may be arranged to navigate the pool cleaning robot 100 to direct the pool cleaning robot to be positioned in a certain location in which a flow level of fluid that is circulated by a pool fluid circulation system is higher than a flow level of the fluid within a majority of the pool (for example—to be in proximity to a drain of the pool), wherein when positioned at the certain location the fluid that is circulated by a pool fluid circulation system passes through a fluid path formed in the pool cleaning robot and thereby rotate a turbine.

Figure 18B:
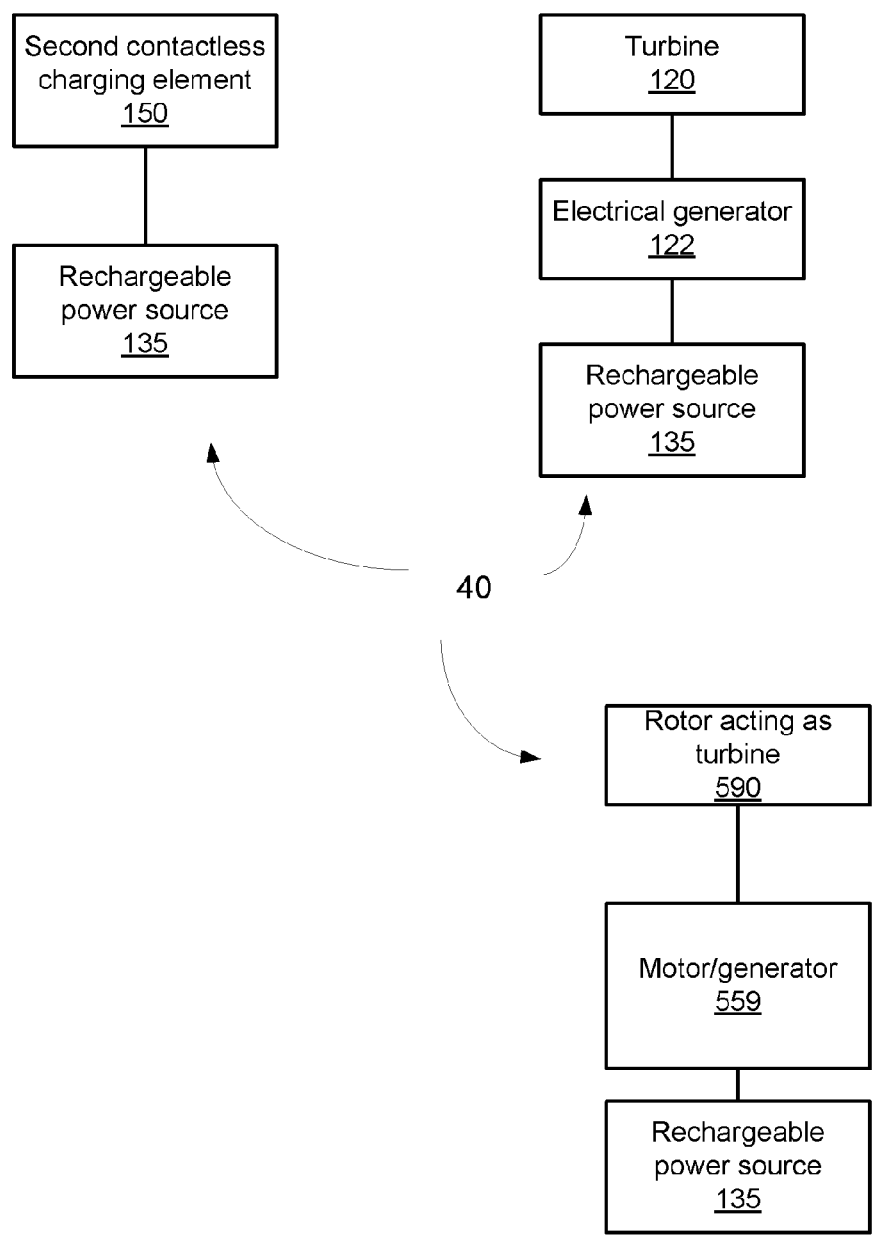
FIG. 18B illustrates power supply modules of a pool cleaning robot according to various embodiments of the invention.

FIG. 18B illustrates power supply modules 40 of a pool cleaning robot 100 according to various embodiments of the invention.

The power supply module 40 is configured to provide electrical power to various power consuming components such as controller 101, motors, sensors, and the like. It may receive the electrical power or generate it.

One power supply module 40 includes a second contactless charging element 150 and a rechargeable power source 135 (see, for example FIGS. 3A-3B and 4A-4C).

Another power supply module 40 includes a turbine 120, electrical generator 122 and a rechargeable power source 135 (see, for example FIGS. 2A-2C).

A further power supply module 40 includes a rotor 590 that acts as a turbine, a motor/generator 559 that acts as a generator and a rechargeable power source 135 (see, for example FIGS. 16A-16B and 17A-17B).

Figure 18C:
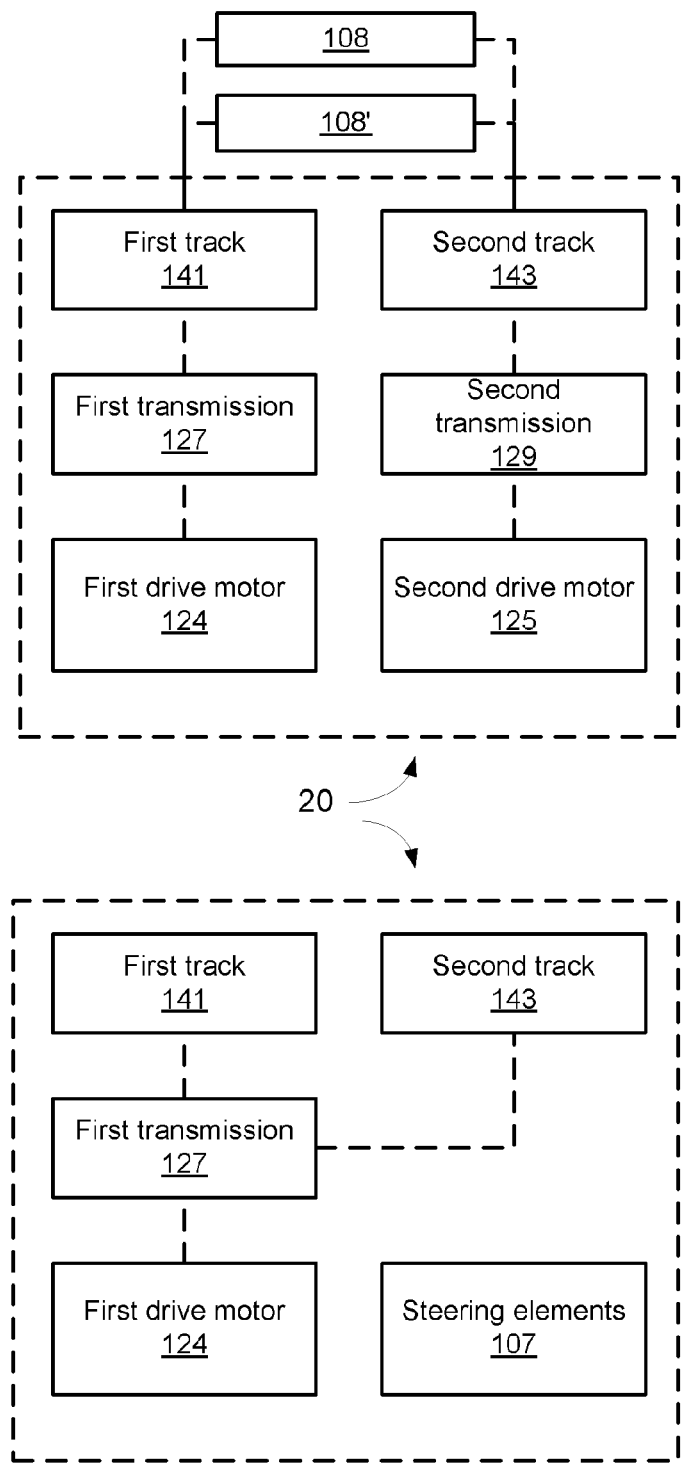
FIG. 18C illustrates drive and steering modules a pool cleaning robot according to various embodiments of the invention.

FIG. 18C illustrates drive and steering modules 20 of a pool cleaning robot according to various embodiments of the invention.

Drive and steering module 20 is arranged to move the pool cleaning robot 100. It may include one or more motors, one or more wheels or tracks and one or more transmissions that convey movements introduced by motors to the one or more wheels and/or one or more tracks.

One drive and steering module 20 includes first drive motor 124, second drive motor 125, first transmission 127, second transmission 129, first track 141 and second track 143. Some of these components are shown in FIGS. 1, 2A-2C, 3A-3C, 4A-4B and the like.

The pool cleaning robot 100 may include a brushing module (denoted 90 in FIG. 18A) that may include one or more brushing wheels such as brushing wheels 108 that are rotated (directly or indirectly) by first and second tracks 141 and 143. The direction of movement of the pool cleaning robot 100 can be controlled by individually controlling the movement of first and second tracks 141 and 143.

Another drive and steering module 20 includes first drive motor 124, first transmission 127, first track 141, second track 143, brushing wheels (not shown) and steering elements 107. Steering elements 107 can include fins, imbalance introduction elements, controllable fluid jet elements and the like. Non-limiting examples of steering elements are provided in U.S. patent application Ser. No. 14/023,544 filed Sep. 11, 2013 which is incorporated herein by reference. Any other steering elements known in the art can be used.

Figure 18D:
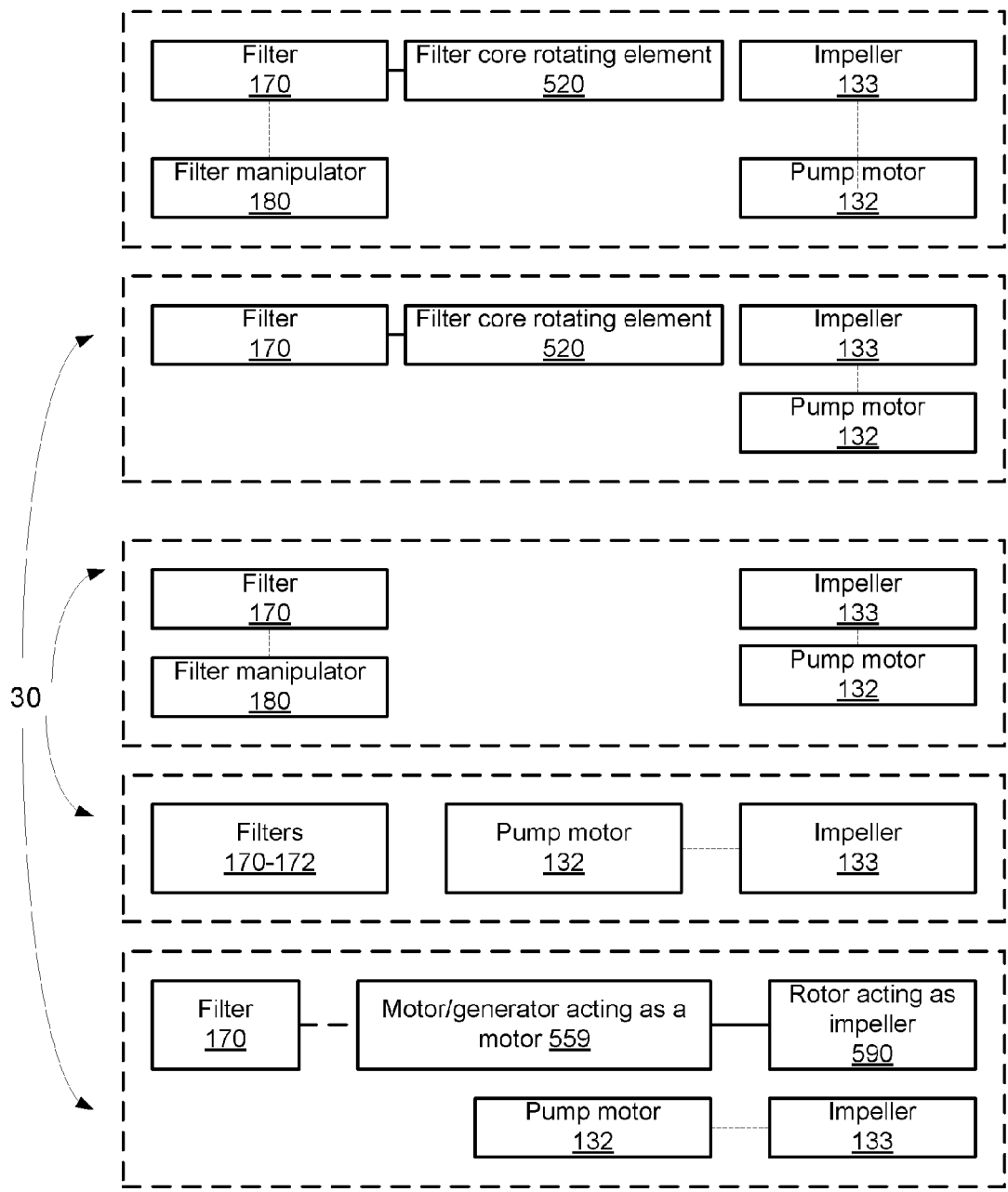
FIG. 18D illustrates fluid control modules of a pool cleaning robot according to various embodiments of the invention.

FIG. 18D illustrates fluid control modules 30 of a pool cleaning robot according to various embodiments of the invention.

A fluid control module 30 is arranged to control a flow of fluid within the pool cleaning robot and to filter said fluid.

It may include, any combination of the following:
a. Impeller 133 and pump motor 132 for inducing fluid to flow through the pool cleaning robot 100 (see, for example FIG. 2C).
b. Rotor 590 that acts as an impeller and a motor/generator 559 that acts as a motor (see, for example, FIGS. 16A, 16B, 17A, 17B, 17C, 17D).
c. Filter 170, 172, 174 or 500. The filter may have, for example, a filter core 510, a filter enclosure 530 and a filter housing 540.
d. A filter core rotating element 552 (see, for example, FIGS. 10, 12 and 14).
e. Filter manipulator 180 (see, for example, FIG. 8).

Figure 18E:
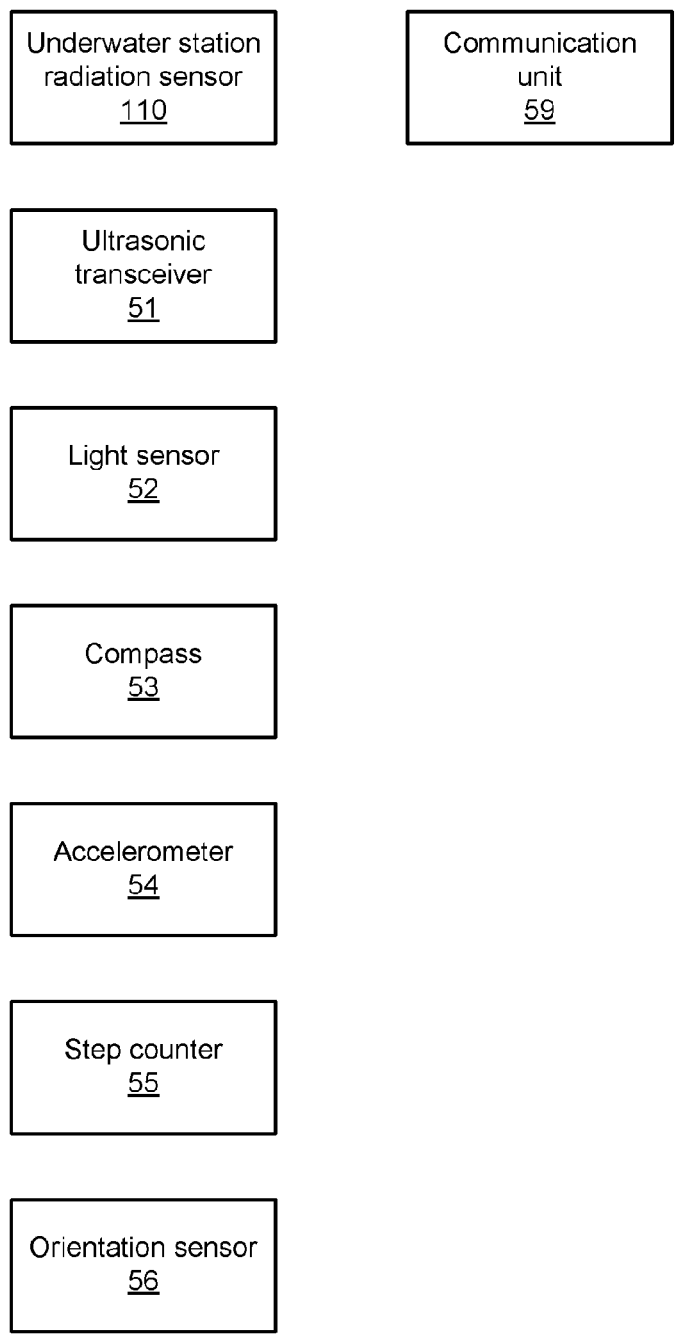
FIG. 18E illustrates sensors of a sensing and communication module of a pool cleaning robot according to various embodiments of the invention.

FIG. 18E illustrates sensors of a sensing and communication module 50 of a pool cleaning robot according to various embodiments of the invention. The sensing and communication module 50 may include one or more of the following sensors:
a. Underwater station radiation sensor 110 for sensing radiation from an underwater station (see, FIG. 1).
b. Ultrasonic transceiver 51 for sensing a flow of fluid in the pool—that is expected to be relatively high near the drain of other flow inducing elements of a pool fluid circulation system.
c. Acoustic sensor 52 that may include an acoustic emitter and an acoustic detector to provide information about the area of the pool the pool cleaning robot 100 is passing on.
d. Gyrocompass 53 or multiple gyrocompasses for providing directional information.
e. Accelerometer 54.
f. Step counter 55 for measuring movement of the pool cleaning robot.
g. Orientation sensor 56 for sensing the orientation of the pool cleaning robot 100.
h. Communication unit 59 for communication with the underwater station 200, or with other elements in the pool (see element 306 of FIG. 2A) or outside the pool.

Figure 18F:
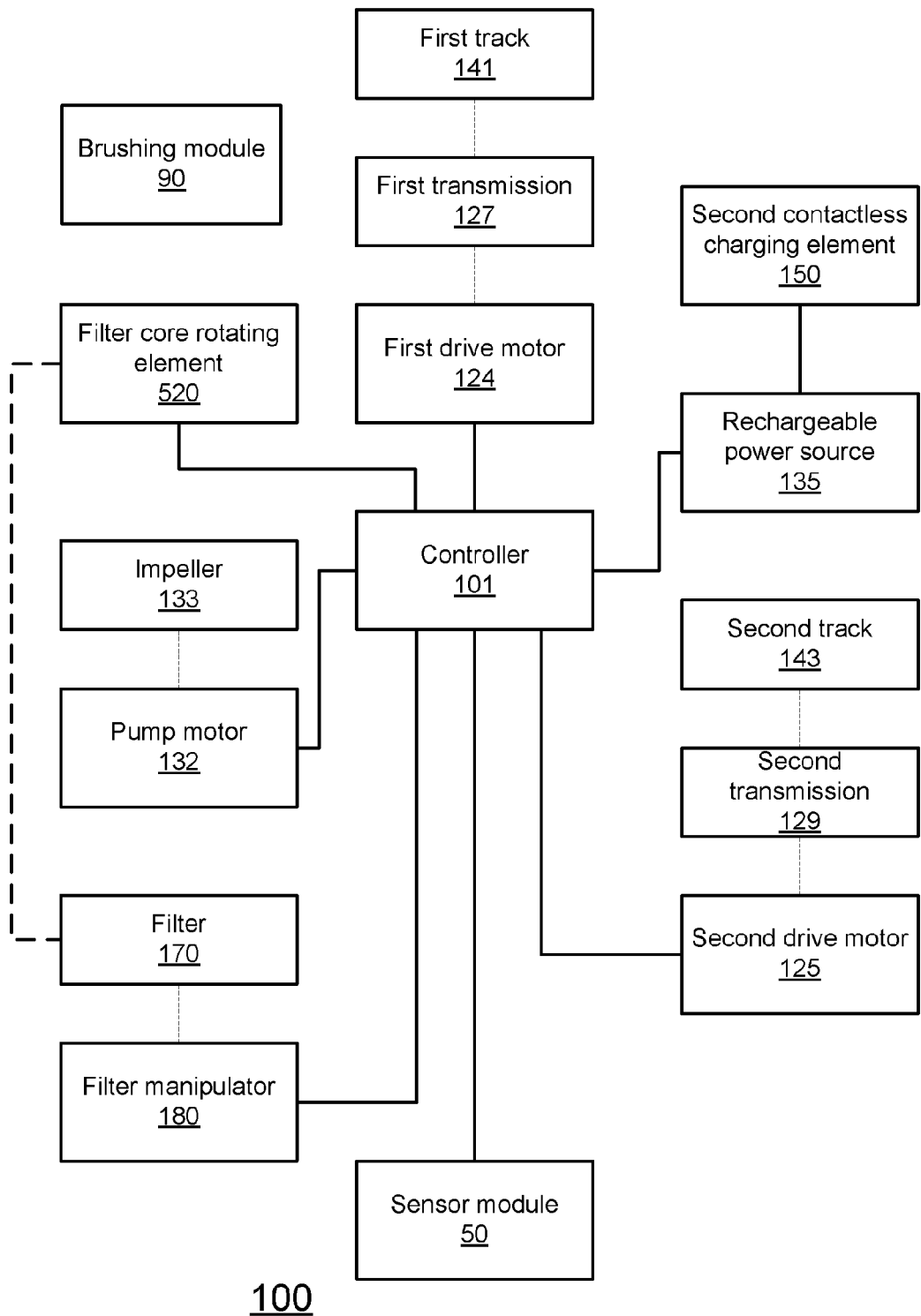
FIG. 18F illustrates various components of a pool cleaning robot according to an embodiment of the invention.

FIG. 18F illustrates various components of a pool cleaning robot 100 according to an embodiment of the invention. This is an example of combination of controller 101 and various components of the drive and steering module 20, power supply module 40, fluid control module 30, sensing and communication module 50 and brushing module 90.

In FIG. 18F the pool cleaning robot 100 includes controller 101, sensing and communication module 50, filter 170, filter manipulator 180, filter core rotating element 520, rechargeable power source 135, second contactless charging element 150, impeller 133, pump motor 132, first and second drive motors 124 and 125, first and second transmissions 127 and 129, first and second tracks 141 and 143.

Figure 18G:
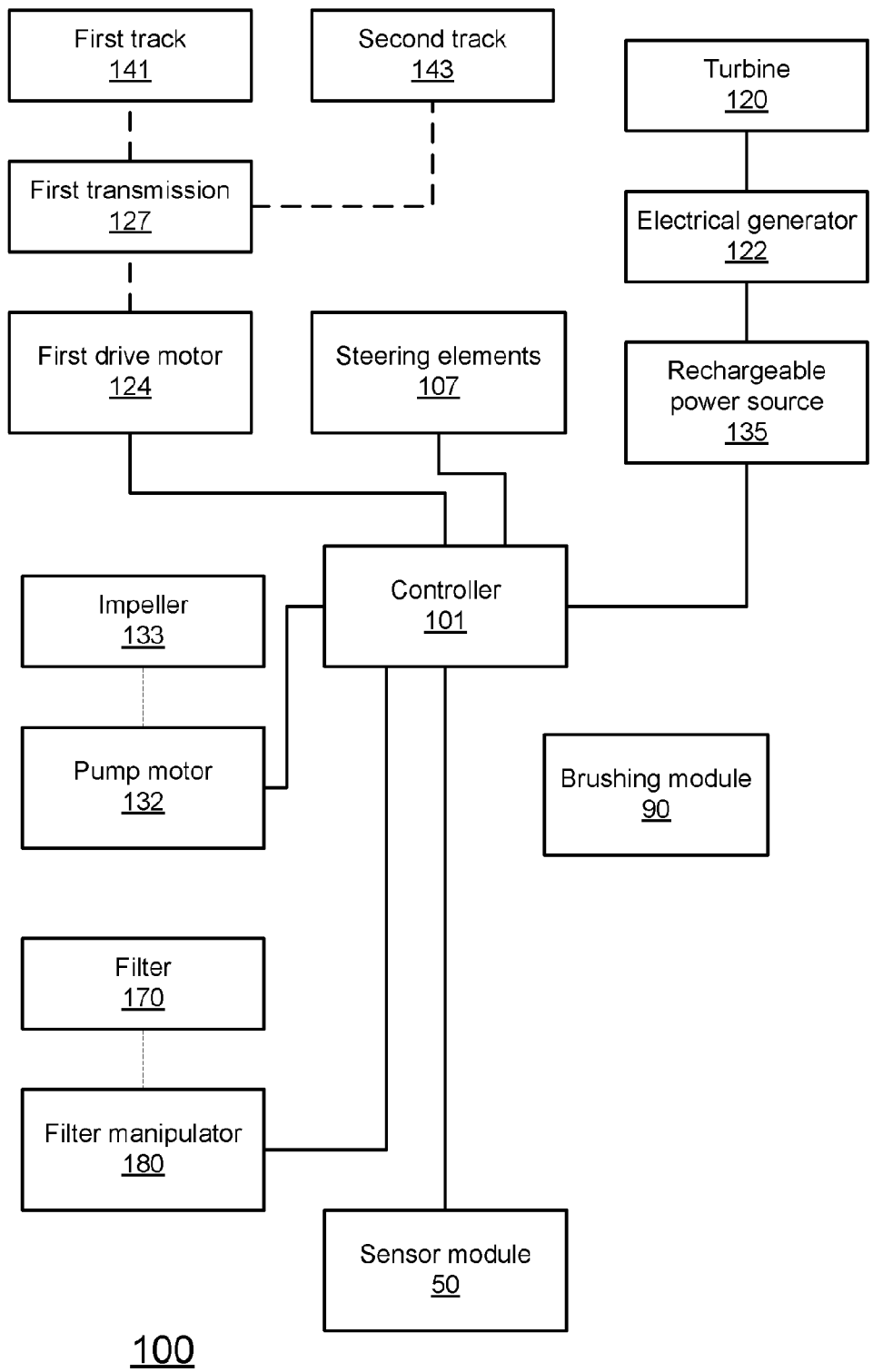
FIG. 18G illustrates various components of a pool cleaning robot according to an embodiment of the invention.

FIG. 18G illustrates various components of a pool cleaning robot 100 according to an embodiment of the invention.

In FIG. 18G the pool cleaning robot 100 includes controller 101, sensing and communication module 50, filter 170, filter manipulator 180, rechargeable power source 135, electrical generator 122, turbine 120, impeller 133, pump motor 132, first drive motor 124, steering elements 107, first transmission 127, first and second tracks 141 and 143 and brushing module 90.

Figure 18H:
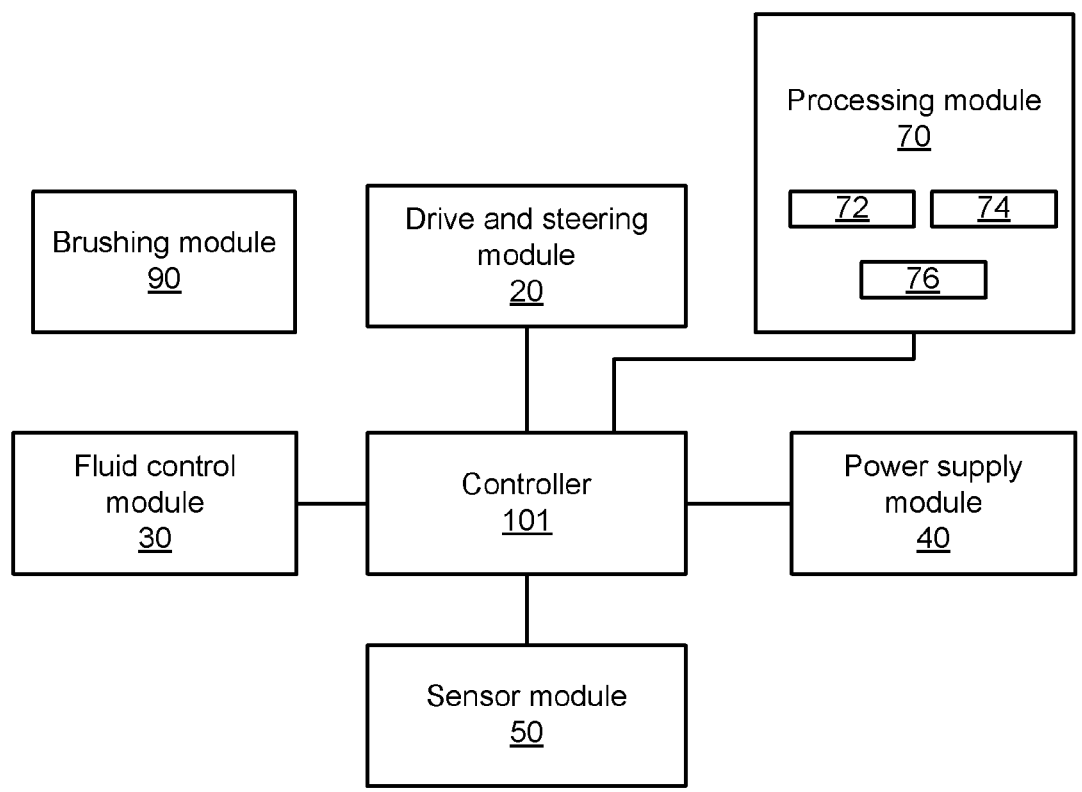
FIG. 18H illustrates various components of a pool cleaning robot according to an embodiment of the invention.

FIG. 18H illustrates various components of a pool cleaning robot 100 according to an embodiment of the invention.

This is an example of combination of controller 101, drive and steering module 20, power supply module 40, fluid control module 30, sensing and communication module 50, brushing module 90 and a processing module 70. The processing module 70 is arranged to process filters (not shown). The processing module 70 may include at least one out of: sanitizing unit 72 that is arranged to irradiate a filter with ultraviolet radiation or perform any other sanitizing process, compressor 74 for compressing a used filter (for example—filter 174 of FIG. 5A), a shredder 76 for shredding a user filter a portion of the filter (its core), and a float inducing module 78 for attaching a floating material (foam, balloon that is inflated) to a user filter and the like.

The processing module 70 can be part of any of the pool cleaning robots illustrated in any previous figures or in any other text of the specification.

Figure 19A:
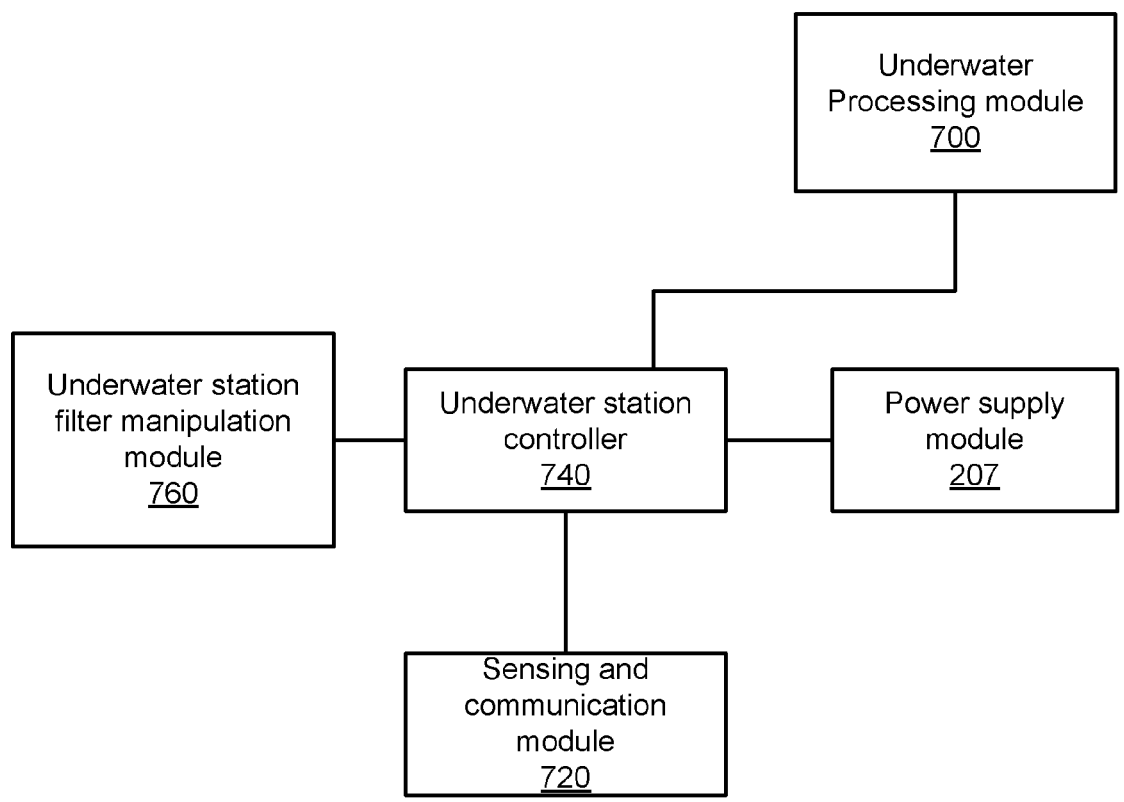
FIG. 19A illustrates various components of an underwater station according to an embodiment of the invention.

FIG. 19A illustrates various components of an underwater station 200 according to an embodiment of the invention.

The underwater station 200 includes an underwater station controller 740, an underwater station filter manipulation module 760, a sensing and communication module 720, a power supply module 207, and an underwater processing module 700.

The underwater station controller 740 controls the various modules of the underwater station 200. It can, for example, use information from sensing and communication module 720 for sensing when a pool cleaning robot is positioned within a charging range from a first contactless charging element and control a provision of power to said first contactless charging element. It may initiate, control and stop a filter insertion process to a pool cleaning robot and/or a filter ejection process from a pool cleaning robot and the like.

The sensing and communication module 720 may include one or more sensors for sensing the location of the pool cleaning robot 100, the status of various operations (processing filters, feeding or extracting filters) and the like. This information may be fed to the underwater station controller 740. This module communicates with the pool cleaning robot or other devices in or outside the pool.

The power supply module 207 supplies power to the various modules of the underwater station 200 and may also feed (in a contactless or a contact based manner) a pool cleaning robot.

The underwater processing module 700 may perform at least one out of: sanitizing of pre-used or used filters, compressing used filters, shredding user filters attaching a floating material (foam, balloon that is inflated) to a user filters and the like.

Figure 19B:
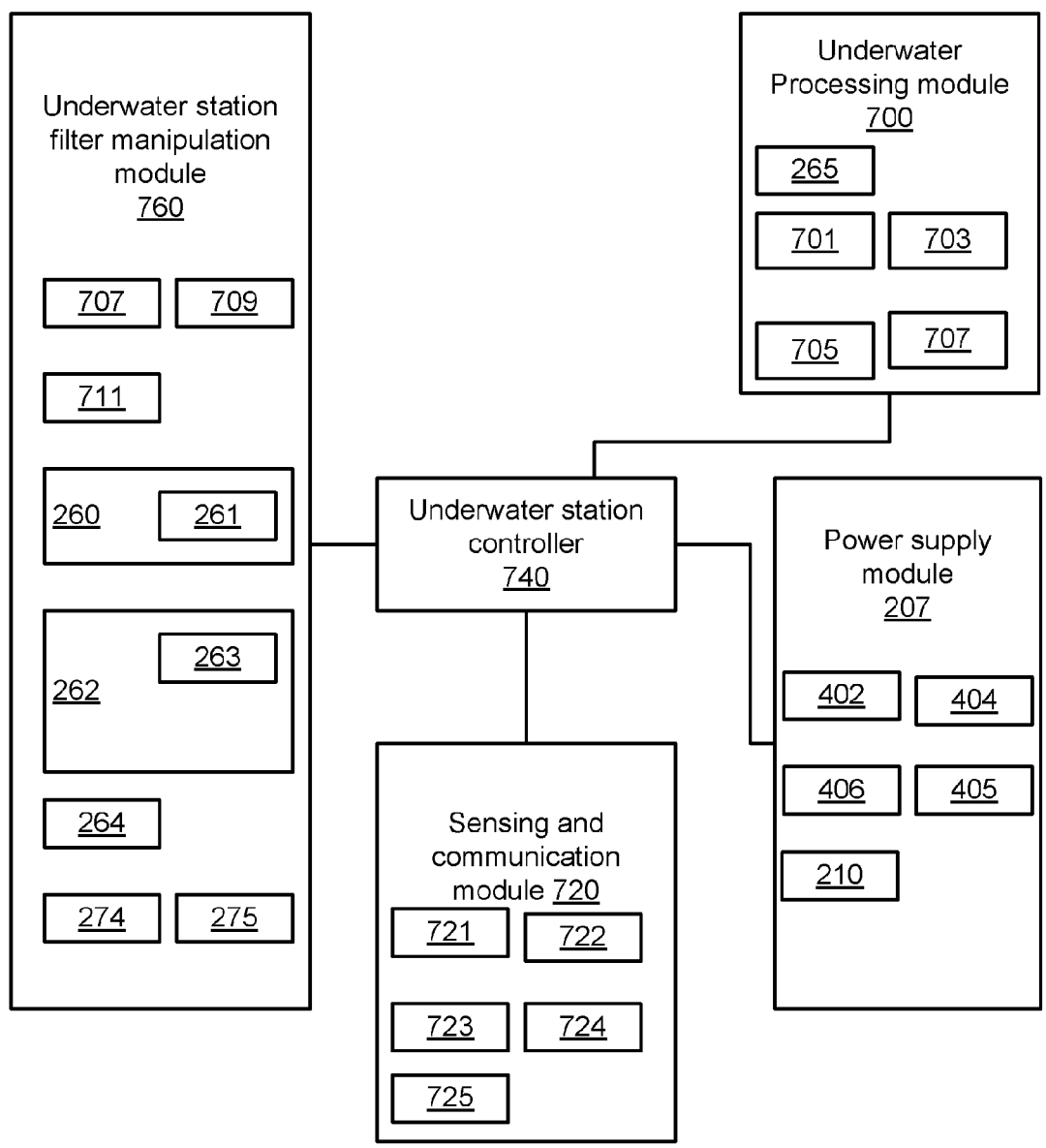
FIG. 19B illustrates various components of an underwater station according to an embodiment of the invention.

FIG. 19B illustrates various components of an underwater station 200 according to an embodiment of the invention. This figure illustrates multiple components per each module of the underwater station 200. Any combination of any components can be provided.

The underwater station filter manipulation module 760 may include at least one out of a. In-housing manipulator 711 for manipulating filters within housing 250.
b. Filter manipulators such as 260, 262 and 264. Each may include movement modules (261, 263, 265 and 275) and storage modules (272 and 270).
  i. Filter manipulator 260 is arranged to store and manipulate pre-used filters (including inserting the pre-used filters to a pool cleaning robot 100, providing and/or arranging filters to/within filter storage module 272, ejecting filters from a pool cleaning robot (see, arm 261 of FIGS. 6A and 6B).
  ii. Filter manipulator 262 is arranged to store and manipulate used-filters (extract from pool cleaning robot, direct used filter towards housing and/or compressor or other processing element). See, for example, FIGS. 6A-6B.
  iii. Filter manipulator 264 is arranged to store and manipulate filters. See, for example, FIGS. 7A-7D.

The sensing and communication module 720 may include at least one out of weight sensor 721, ultrasonic transceiver 722, proximity sensor 723, cleanliness sensor 724 and communication unit 725. The sensors 721, 722, 723 are arranged to sense the location of a pool cleaning robot 100 and/or evaluate wherein the pool cleaning robot is positioned in a docking position in which it can be charged and/or receive or extract filters. Cleanliness filter 724 may sense the cleanliness of pre-used filters and/or used filters. It may indicate that an extracted filter is clean enough to be used and cause the controller 740 to control a process of returning the used filter to the pool cleaning robot 100 via one of the filter manipulators. The communication unit 725 may be arranged to communicate with the pool cleaning robot or other devices in or outside the pool. It may include, for example radiation sources 241 and 242 of FIG. 1.

The power supply module 207 may include at least one of the following:

a. Electrical cable 402 (FIG. 3A).
b. Turbine 404 (FIG. 4B).
c. Electrical generator 406 (FIG. 2B).
d. Rechargeable power source 405.
e. First contactless charging element (such as a coil) 210 (see FIG. 1).

The underwater processing module 700 may include at least one of the following:

a. Ejector 707 for ejecting used filters from the underwater station 200.
b. Floater 709 for attaching or otherwise associating a used filter with floating materials (foam, inflated balloon).
c. Compressor 701 and/or 265 (see FIGS. 6A-6B).
d. Shredder 703.
e. Sanitizer 705.

FIG. 20A illustrates a pool 300, a pool cleaning robot 100 and a pool fluid circulation system that includes drain 302, fluid pipes 304, filter 330, temperature control unit 320 and circulating pump 310 and tube 408. Any type of pool fluid circulation system can be utilized for the purposes of this invention. A pool can be regarded as a swimming pool, any type of pool or any type of vessel, container, enclosure that may contain fluid.

Any combination of any components of any pool cleaning robot illustrated in any of the figures may be provided.

Any reference to any pool cleaning robot is applied mutatis mutandis to a method for operating the pool cleaning robot.

Any combination of any components of any underwater systems can be provided.

Any reference to any underwater system is applied mutatis mutandis to a method for operating the pool cleaning robot.

FIG. 21 illustrates method 400 according to an embodiment of the invention.

Method 400 is autonomous operation. Method 400 includes step 410 of performing, by at least one of a pool cleaning robot and an underwater station, in an autonomous manner at least one out of pool cleaning robot filter replacement and pool cleaning robot charging.

The term autonomous may mean without human intervention. The pool cleaning robot charging is applied on a pool cleaning robot that is not constantly connected to a cord that extends outside the pool and constantly supplies to the pool cleaning robot electrical energy or supplied to the pool cleaning robot a constant a flow of fluid.

For example, executing the process at least partially illustrated in any one of FIGS. 1, 2A, 2B, 2C, 3A, 3B, 4A, 4B may amount to performing in an autonomous manner a pool cleaning robot charging.

Yet for another example, executing the process at least partially illustrated in any one of FIGS. 6A, 6B, 7A, 7B, 7C, 7D, 8 and 12 may amount to performing in an autonomous manner a pool cleaning robot filter replacement.

FIG. 22 illustrates method 500 according to an embodiment of the invention.

Method 500 includes stage 510 of filtering fluid by a pool cleaning robot by using a filter that fulfils at least one of the following: (i) it has a filter core that is rotated by a filter core rotator when the filter applied a filtering operation, (ii) is positioned in a filtering position while at least one other filter of the pool cleaning robot is positioned within the pool cleaning robot in a non-filtering position, (iii) is positioned in a filtering position when the pool cleaning robot and by a filter manipulator.

For example, the filtering can be executed by any one of the filters illustrated in FIGS. 5A, 5C, 6A, 6B, 7A, 7B, 7C, 7D, 8, 9, 10, 11A, 11B, 12, 13A, 13B, 16A, 16B, 17A-17F.

Above Water Charging and Filter Changing

According to embodiments of the invention there may be provided an external docking station that is positioned above the water. This external docking station may be provided instead of the underwater docking station or in addition to the underwater docking station.

Figure 26:
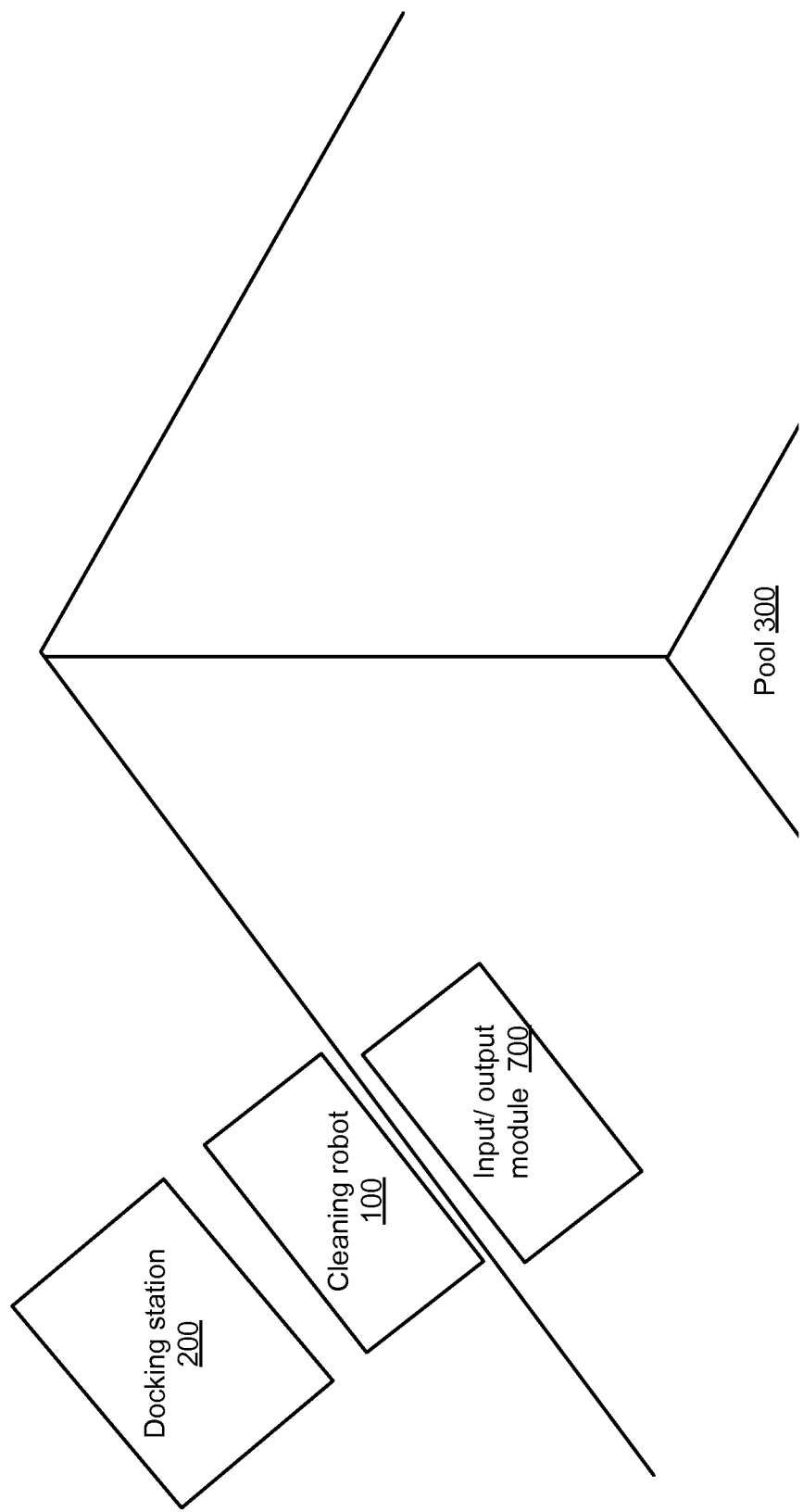
FIG. 26 illustrates an input/output module, an external docking station and a pool cleaning robot according to an embodiment of the invention.

The external docking station may be positioned at the edge of the pool, in proximity (1-50 centimeters) from the edge of the pool or further away from the pool. The pool cleaning robot can autonomously climb outside the pool, can autonomously re-enter the pool, can be assisted (when entering the pool and/or exiting the pool) by a mechanical module (such as an input/output module 700 of FIG. 26), can be taken out of the pool by a human, and the like.

Various systems for inputting and outputting a pool cleaning robot are illustrated in U.S. provisional patent Ser. No. 61/890,260 filing date 13 Oct. 2013 which is incorporated herein by reference.

The external docking station may resemble, be different or be the same as any underwater docking station 200 illustrated in the previous FIGS. 3A-3C, 4A-4B, 6A-6B and 7A-7D). It may be modified to be charged by electrical charge or by a jet of water provided outside the pool, by solar powered panels, may exclude filter ejection module 240 of FIGS. 6A and 6B, and the like. The docking station 200 may be used to replace filters of the cleaning robot and/or to charge the cleaning robot.

Figure 23:
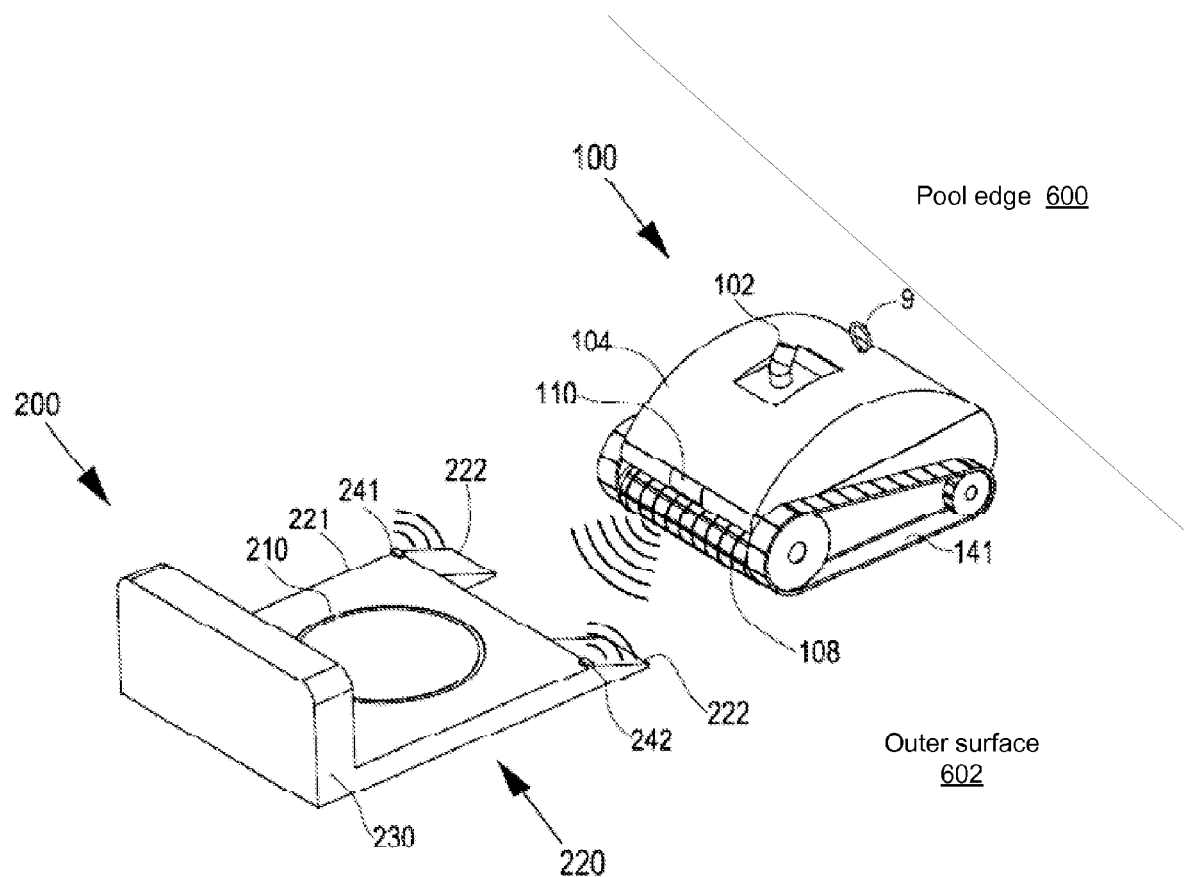
FIG. 23 illustrates an external docking station and a pool cleaning robot according to an embodiment of the invention.

FIG. 23 illustrates an external docking station 1200 that resembles the underwater docking station 200 of FIG. 1 but is located on an outer surface 602 outside the pool and proximate to the pool edge 600. External docking station 1200 may include first contactless charging element 210 that is arranged to (a) be fed by the electrical supply module and (b) generate an electromagnetic field during at least one period during which a second contactless charging element of a pool cleaning robot is within a charging range from the first contactless charging element, and wherein the electromagnetic field charges the second contactless charging element. The coupling between the first and second contactless charging elements can be done by induction and/or by magnets.

Figure 24:
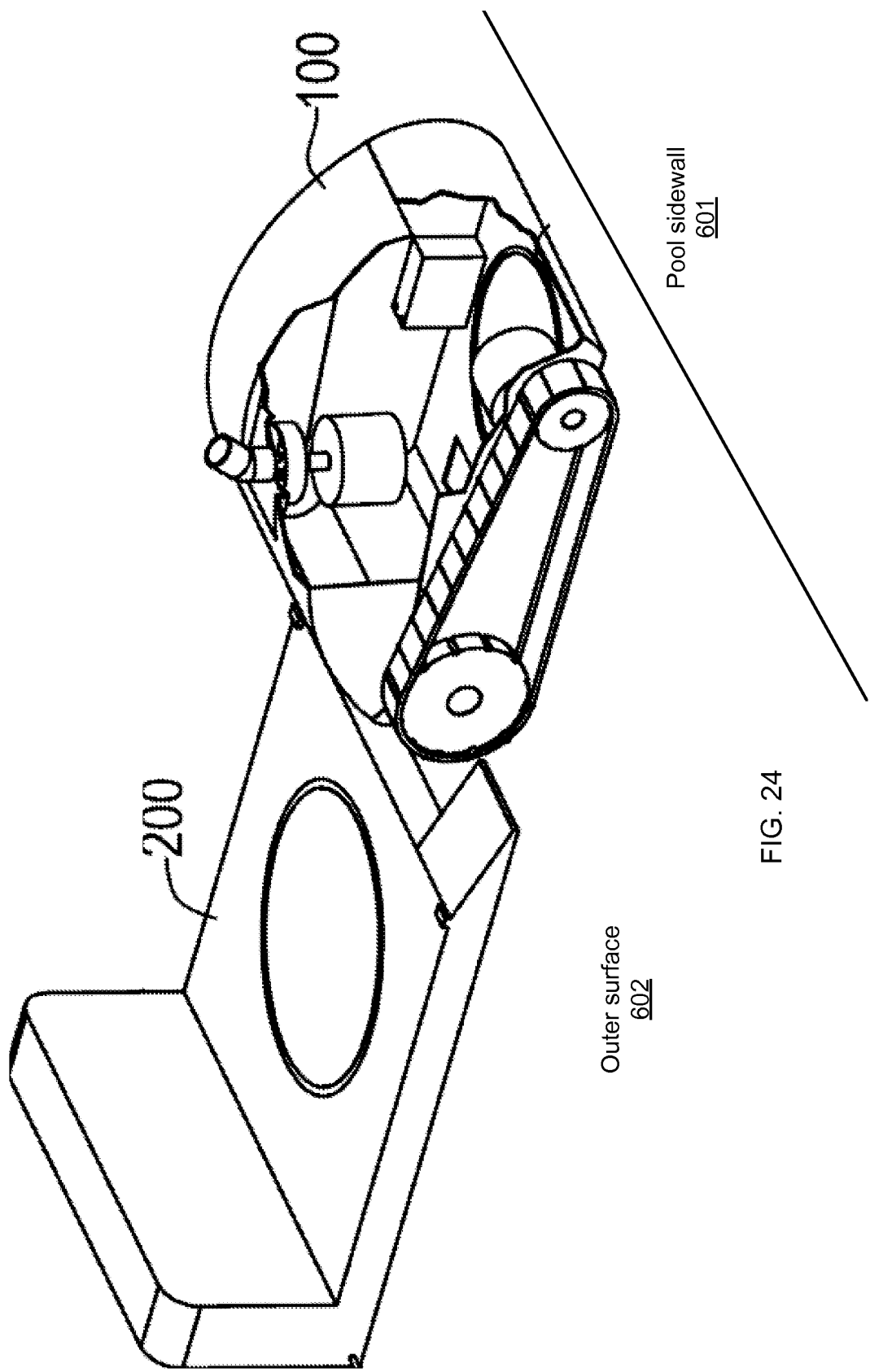
FIG. 24 illustrates an external docking station and a pool cleaning robot according to an embodiment of the invention.

FIG. 24 illustrates an external docking station 1200 that resembles the underwater docking station 200 of FIG. 3A but is located on an outer surface 602 outside the pool (having pool sidewall 601).

Figure 25:
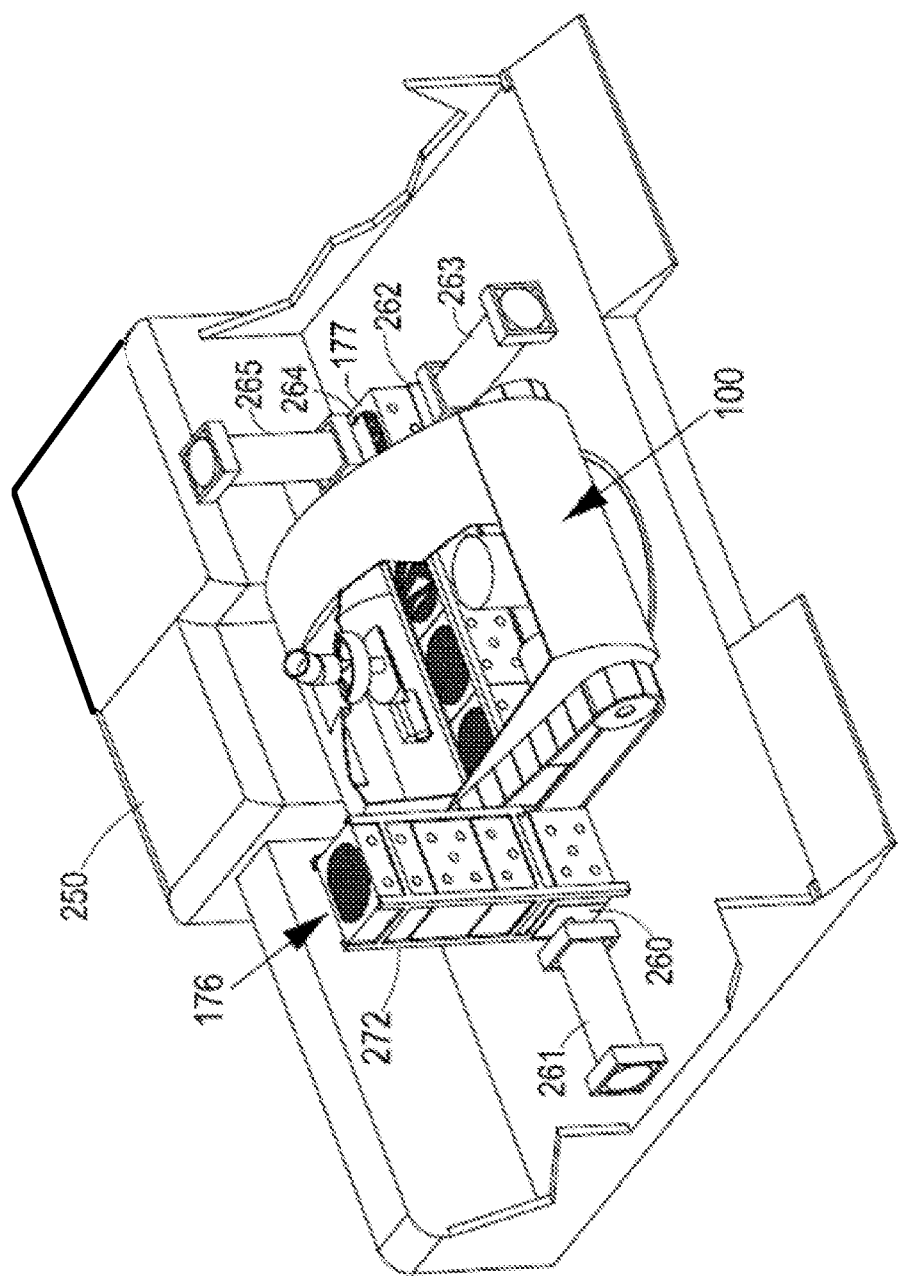
FIG. 25 illustrates an external docking station and a pool cleaning robot according to an embodiment of the invention.

FIG. 25 illustrates an external docking station 1200 that resembles the underwater docking station 200 of FIG. 6A but does not include the chimney shaped filter ejection module 240—it may have other means for ejecting these filters. FIG. 25 also shows multiple filters 176 and 177 according to an embodiment of the invention.

Filters 176 are stored in a first filter storage module (such as filter storage module 272 of FIG. 6A) 272 and then fed to the pool cleaning robot 100 by a first filter manipulator that is represented by arm 261.

Used filters (such as used filter 177) are ejected from the pool cleaning robot 100 by the first filter manipulator (when the same movement used for inserting filters can also eject filters) or by a second filter manipulator that is represented by arm 263 that pushes used filters into underwater station housing 250.

Arm 263 and arm 261 are illustrated as being oriented to each other but they may be parallel to each other and, additionally or alternatively, be oriented to each other by an angle that differs from ninety degrees.

In FIG. 25 the pool cleaning robot 100 stores multiple filters that are arranged in a line to form a sequence of filters. An insertion of a new filter by arm 261 pushes the sequence of filters such as to eject a used filter from pool cleaning robot 100.

Arm 263 of FIG. 25 does not assist in the ejection of used filters but may direct a used filter 177 that was ejected from the pool cleaning robot towards compressor that is (represented by arm 265) that compresses a used filter to provide a compressed used filter. The compressed used filter may be ejected from external docking station, may be temporarily stored by external docking station, may trigger the external docking station to send an alert indicating a user that a compressed used filter is ready to be unloaded from the external docking station, and the like.

It is noted that the filter manipulator that is represented by arm 263 may have other shapes and configurations. It may remove one or more used filters from the pool cleaning robot without the assistance of manipulator 261. For example, arm 261 may be replaced by an extracting element that may extract one or more used filters from pool cleaning robot. An extraction element may be or may include a hook, a suction element, a magnet or any other shape and size that allows it to contact a used filter that is located within pool cleaning robot and to extract it.

The external docking station is further illustrated as including a housing 250 and may also include (not shown) a filter ejection module from which used filters can be ejected or otherwise taken outside the external docking station.

The external docking station 1200 may have a handle to grip the docking station for shunting around. Mobility of the external docking station is achieved by means of at least two wheels attached to the bottom of the external docking station base.

Any pool cleaning robot of any of the previous figures may be charged by electrically conducting charging pins or a charging strip (not shown) situated in the front of the pool cleaner or anywhere else suitable in the pool cleaner's periphery that will be coupled to a similar electrical charging system on the docking station for direct contact charging, and/or have his filters replaced by the external docking station.

An automatic jet water stream may be provided in the docking station directed at spraying water from underneath or the sides of the docking station onto the pool cleaner (whilst positioned on the docking station) and into the first or second filter opening areas.

FIG. 27 illustrates a method 800 according to an embodiment of the invention.

Method 800 illustrates an autonomous operation of a pool cleaning robot. Method 800 includes step 810 of performing, by at least one of a pool cleaning robot and an external docking station, in an autonomous manner at least one out of pool cleaning robot filter replacement and pool cleaning robot charging.

Figure 28:
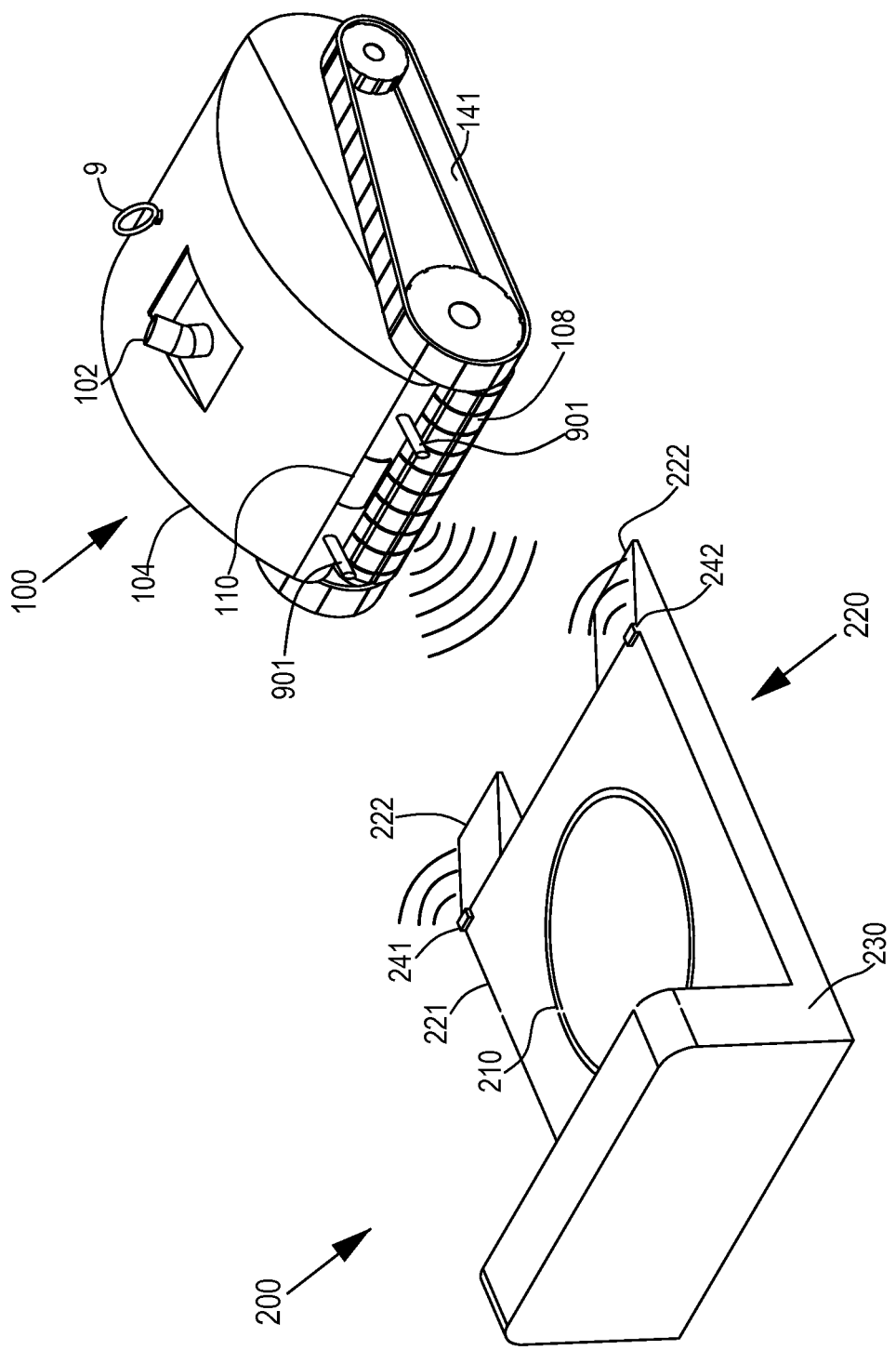
FIGS. 28-29 illustrate pool cleaning robots and docking stations according to various embodiments of the invention.
Figure 29:
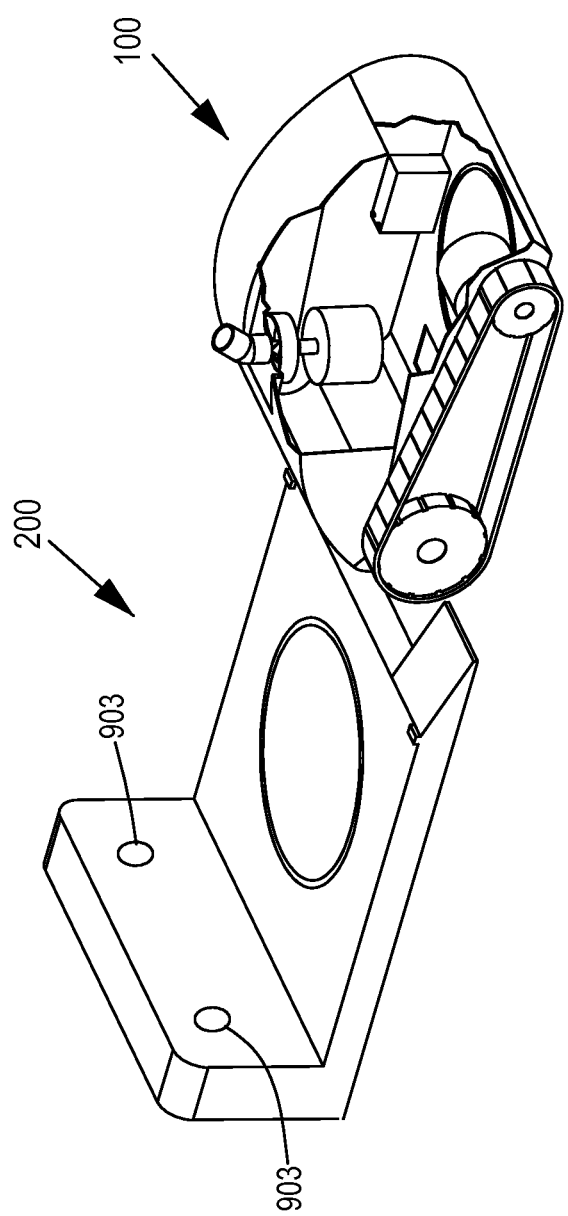

FIGS. 28-29 illustrate pool cleaning robots 100 and external docking stations 200 according to various embodiments of the invention.

FIG. 28 illustrates a pool cleaning robot 100 that has interfacing elements such as pins 901 that extend from the pool cleaning robot and are arranged to contact sockets 903 (of FIG. 29) formed in the external docking station—thus allowing provision of power supply to the pool cleaning robot—when the pins enter the sockets. FIG. 28 also shows a power cord 902 for feeding the external docking station. There may be one or more interfacing elements (and/or one or more sockets) and their shape and size may differ from those illustrated in FIGS. 28-29.

Figure 30:
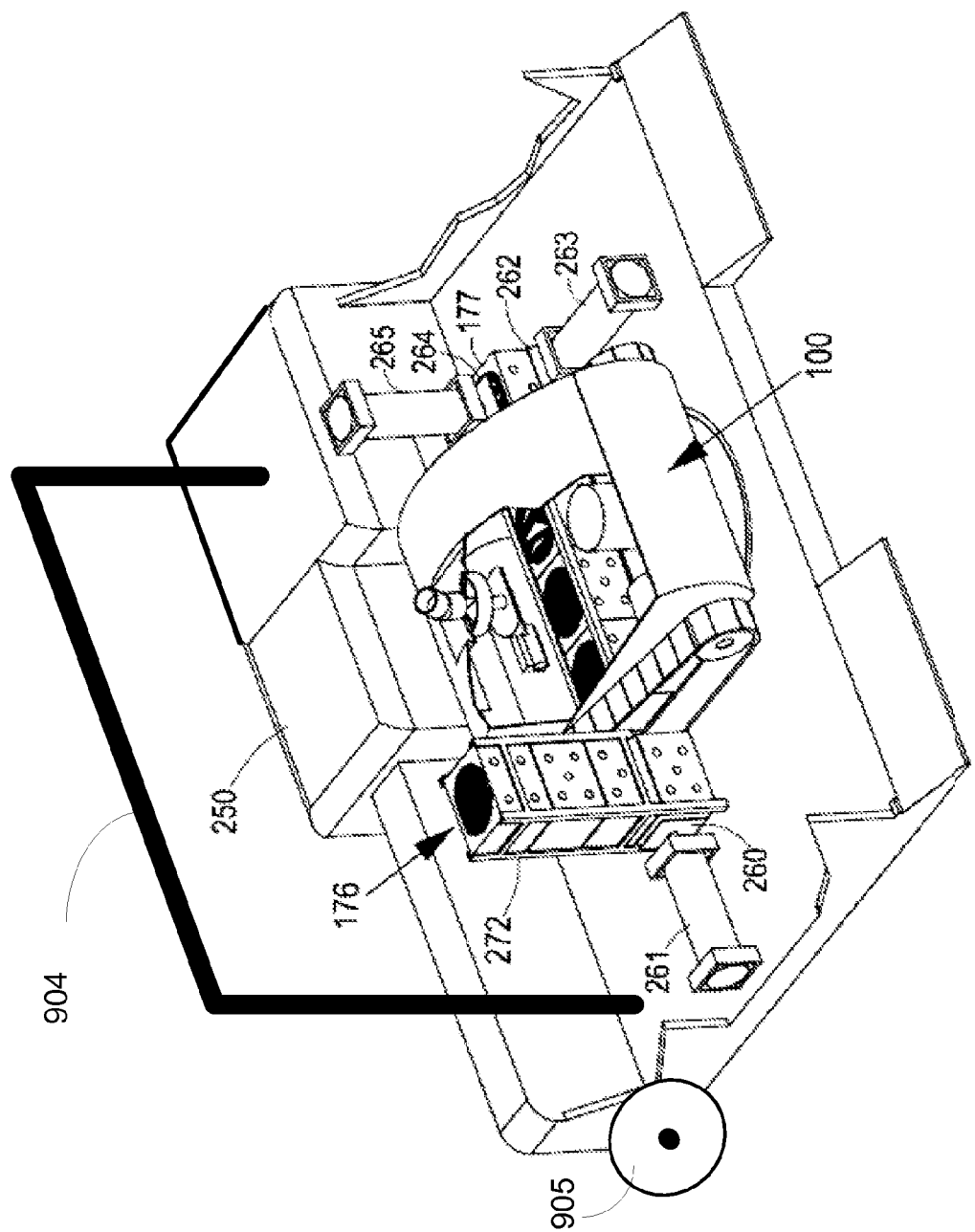
FIGS. 30-37 illustrate docking stations according to various embodiments of the invention.
Figure 31:
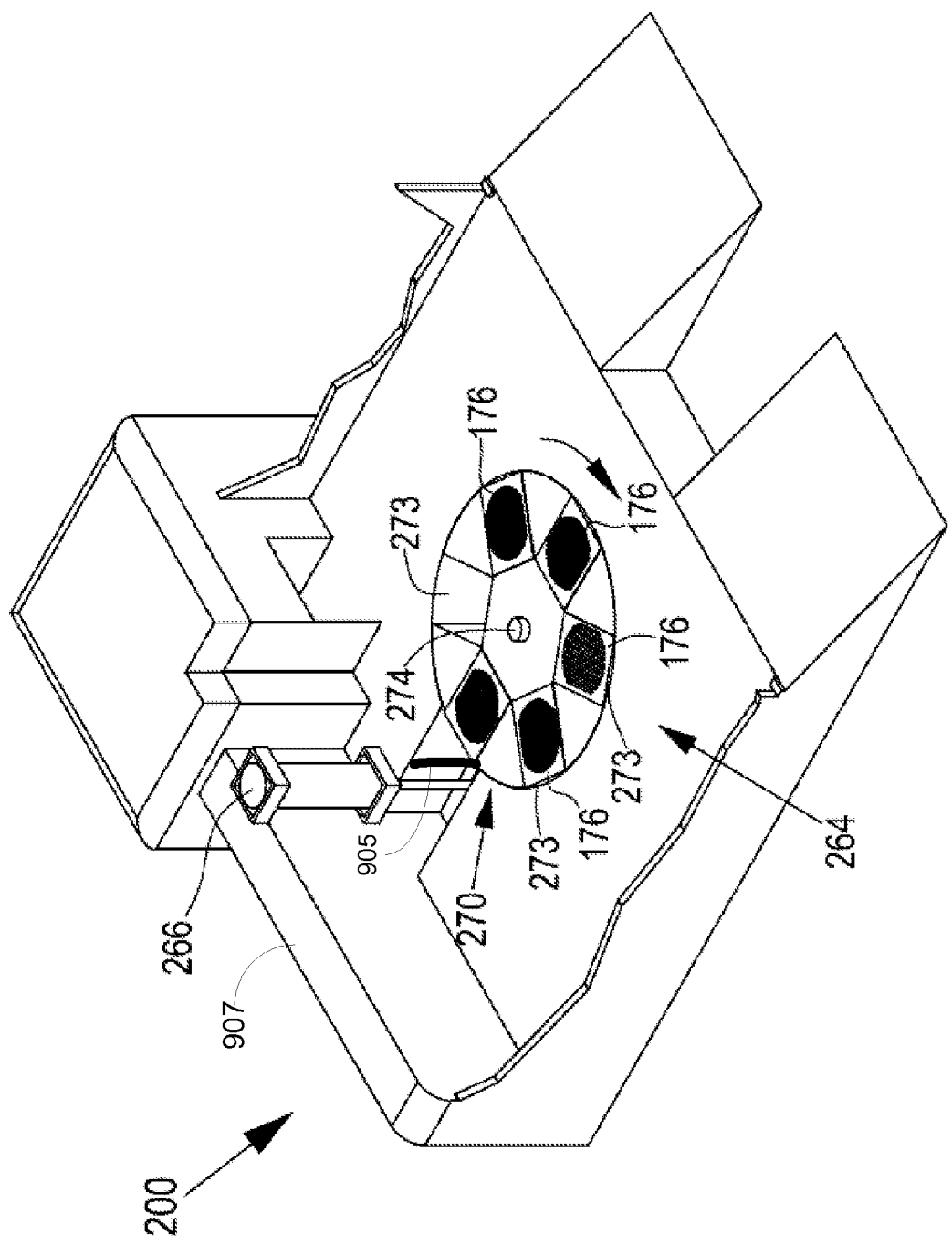

FIGS. 30-31 illustrate external docking stations 200 according to various embodiments of the invention.

An external docking station can be moved from location to location and thus has a user interface (such as handle 904 of FIG. 30) to be contacted by a user that wishes to move the external docking station. There may be one or more for handles, the shape and size of the user interface may differ from the handle of FIG. 30.

The external docking station 200 may, additionally or alternatively, have one or more wheels (such as wheel 905 or 1110 and another wheel—not shown at an opposite side of the external docking station) of surface interfaces that ease the movement of the external docking station.

FIG. 31 illustrates an external docking station that include a hose or other fluid conduit that allows washing an interior of the pool cleaning robot (or at least washing a filter enclosure) after a filter was removed from the pool cleaning robot and before placing another filter. It is further noted that arm 266 may be moved into wall 907 thereby allowing the pool cleaning robot to contact the wall 907. This may be required when applying a pin-charging scheme as illustrated in FIGS. 28-29.

External docking station 200 includes a filter manipulator 264 that includes an arm 266 for elevating a filter from a filter storage module 270 that may have a radially symmetrical shape (annular, cylindrical and the like) that has multiple compartments 273 for storing multiple filters 176. The filter storage module 270 is rotated about its center by a movement module that has an axel denoted 274 for rotating the filter storage module 270 about its axis—thereby selecting a selected filter to be inserted to the pool cleaning robot 100 via an opening formed at the bottom of the housing of the pool cleaning robot. The selected filter is positioned in proximity to arm 266 in order to allow arm 266 to elevate the filter into the pool cleaning robot 100. An opposite process may be used to extract a used filter from the pool cleaning robot 100—the arm 266 contacts the filter and lowers it to an empty compartment of the filter storage module 270.

Figure 32:
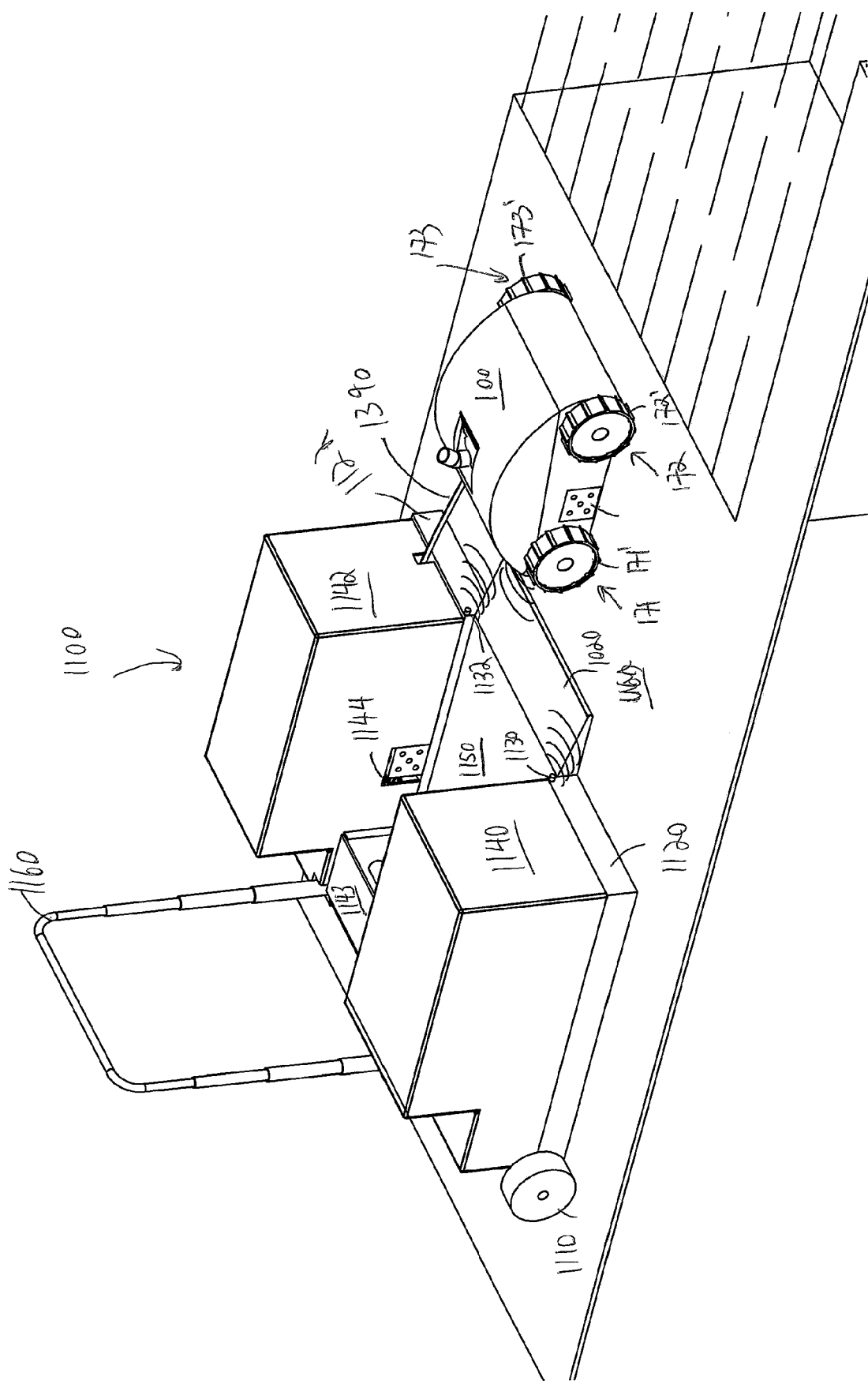

FIG. 32 illustrates a pool cleaning robot 100 that approaches the external docking system 1100 according to an embodiment of the invention.

Figure 34:
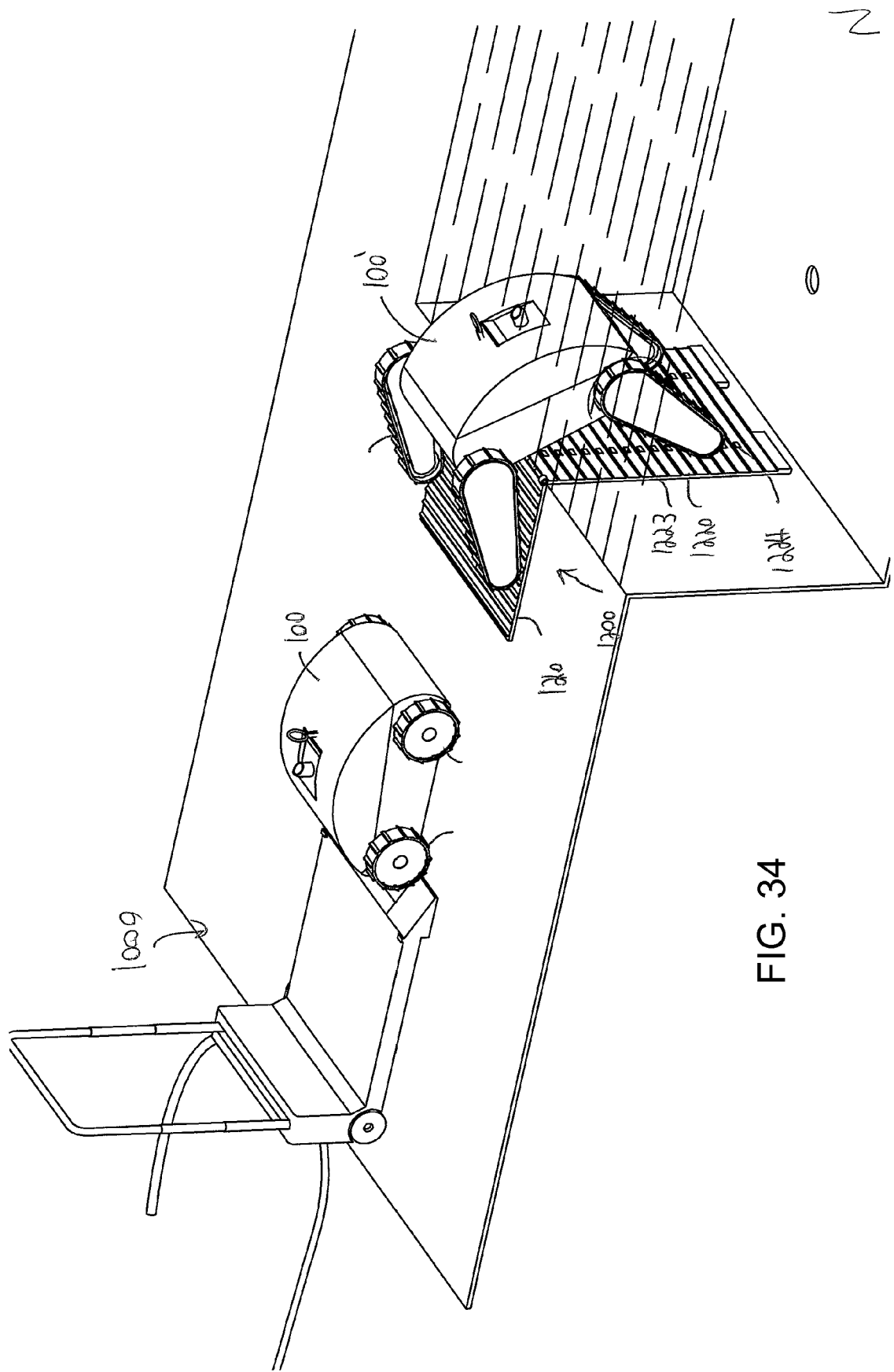

Pool cleaning robot 100 includes wheels 171, 172, 173 and another wheel (not illustrated) and is equipped with suitably adapted threads 171', 172' and 173'—each wheel may include a non-smooth exterior—it may include threads of other protuberances—that may be shaped to fit a non-smooth surface of interfacing device 1200 of FIG. 34.

FIG. 32 illustrates the external docking station 1100 as including a sloped surface 1160 on which the pool cleaning 100 may mount when driving towards surface 1150 and positioning itself at a filter replacement position. Surface 1150 is surrounded by first housing 1140, second housing 1142 and third housing 1143.

First housing 1140 is positioned above first bottom surface 1120 and second housing 1142 is positioned above second bottom surface 1122.

Radiation sources 1130 and 1132 are positioned at the front side of external docking station 1100 and are placed on both sides of surface 1150.

Pool cleaning robot 100 may navigate itself by receiving and analyzing the radiation beacons transmitted from radiation sources 1130 and 1132.

External docking station includes a filter manipulator that is arranged to (i) input a filter into a pool cleaning robot that exited a pool and is located in a filter replacement position and (ii) assist in positioning the filter at a filtering position in which the filter is at least partially disposed within a fluid path formed between a first fluid opening and a second fluid opening of the housing thereby allowing the filter to apply a filtering operation on fluid that passes through the fluid path; and (iii) assist in a removal of one or more used filters from the pool cleaning robot.

First housing 1140 may surround a first portion of the filter manipulator and second housing 1142 may surround a second portion of the filter manipulator. First and second housings 1140 and 1142 include openings for receiving and/or outputting filters. In FIG. 32 second housing 1142 is illustrates as including a filter opening 1144.

Second housing 1142 has an opening through which power cable 1390 extends. The power cable may be coupled to the pool cleaning robot or any other device.

In FIG. 32 the external docking station 1100 is illustrated as including a handle 1160. Any other interfacing element may be included in external docking station 1100.

Figure 33:
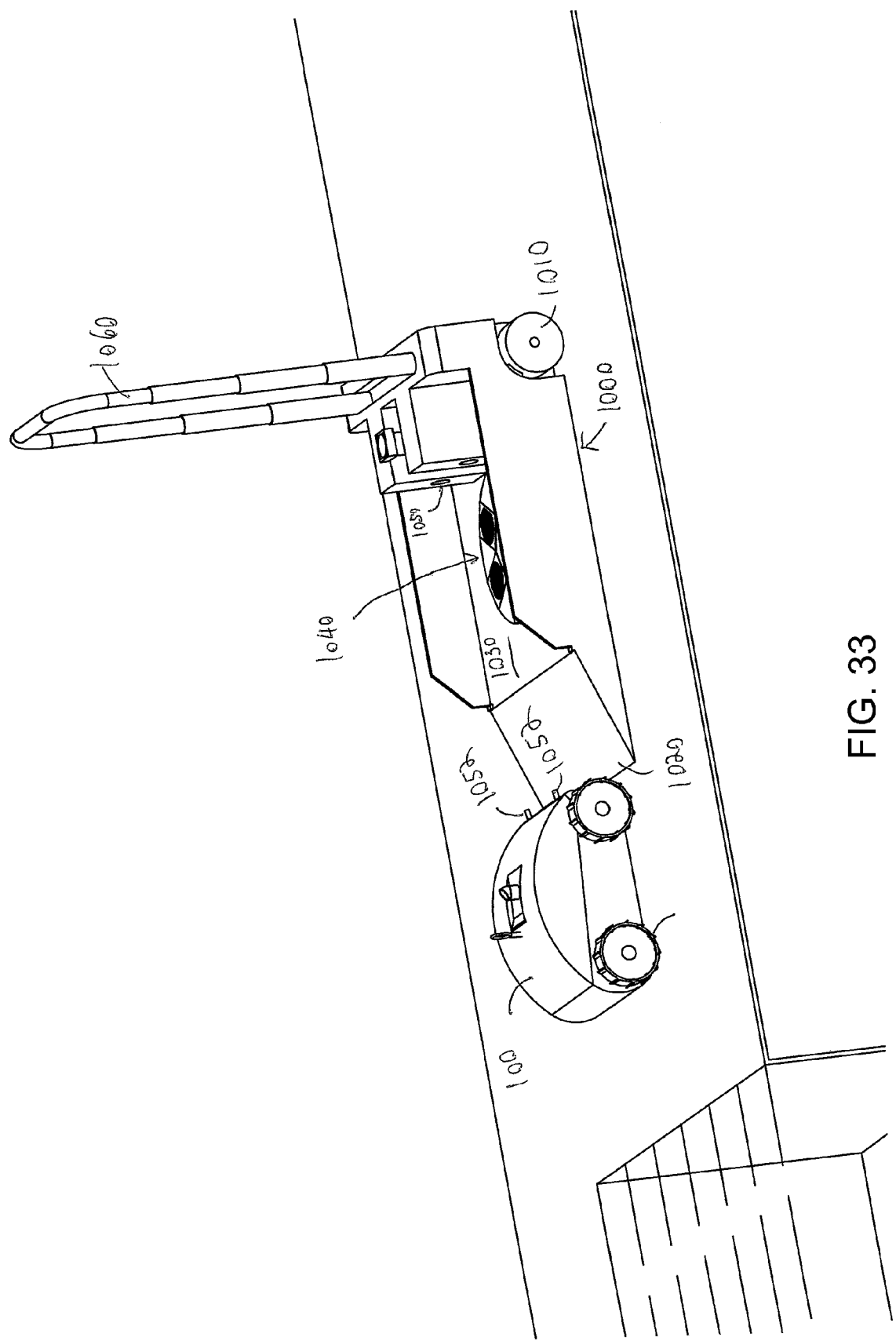

FIG. 33 illustrates a pool cleaning robot 100 and an external docking station 1000 according to an embodiment of the invention.

Pool cleaning robot 100 includes pins 1052 for receiving power from sockets 1050 of external docking station 1000.

External docking station 1000 includes filter manipulator 1040 that may be the same as filter manipulator 270 of FIG. 31.

Filter manipulator 1040 is positioned within an opening in surface 1030. Surface 1030 is preceded by sloped surface 1020.

Filter manipulator 1040 may have a radially symmetrical shape (annular, cylindrical and the like) that has multiple compartments for storing multiple filters. The filter storage module may be is rotated about its center by a movement module that has an axel for rotating the filter storage module about its axis—thereby selecting a selected filter to be inserted to the pool cleaning robot 100 via an opening formed at the bottom of the housing of the pool cleaning robot. The selected filter is positioned in proximity to an arm (not shown) in order to allow arm to elevate the filter into the pool cleaning robot 100. An opposite process may be used to extract a used filter from the pool cleaning robot 100—the arm contacts the filter and lowers it to an empty compartment of the filter storage module 1040.

FIG. 33 also illustrates the external docking system 1000 may have wheels 1010 and handle 1060.

FIG. 34 illustrates an external docking station 1000 and two pool cleaning robots 100 and 100' that approach external docking station 1000. Pool cleaning robot 100' and pool cleaning robot 100 may exit the pool while interfacing with interfacing device 1200.

Interfacing device 1200 includes pool sidewall interface 220 and an external surface interface 210 that may be oriented to each other (for example by ninety degrees). Interfacing device 1200 is shown as including magnets 1224, and fins 1223 that face upwards.

FIG. 34 illustrates a pool cleaning robot 100 that approaches the external docking station 1300 according to an embodiment of the invention.

Pool cleaning robot 100 includes wheels 171, 172, 173 and another wheel (not illustrated) and is equipped with suitably adapted threads 171', 172' and 173'—each wheel may include a non-smooth exterior—it may include threads of other protuberances—that may be shaped to fit a non-smooth surface of interfacing device 200 of FIG. 34. FIG. 34 further depicts power cord 902 and water supply pipe connecting to the back of the docking station.

Figure 35:
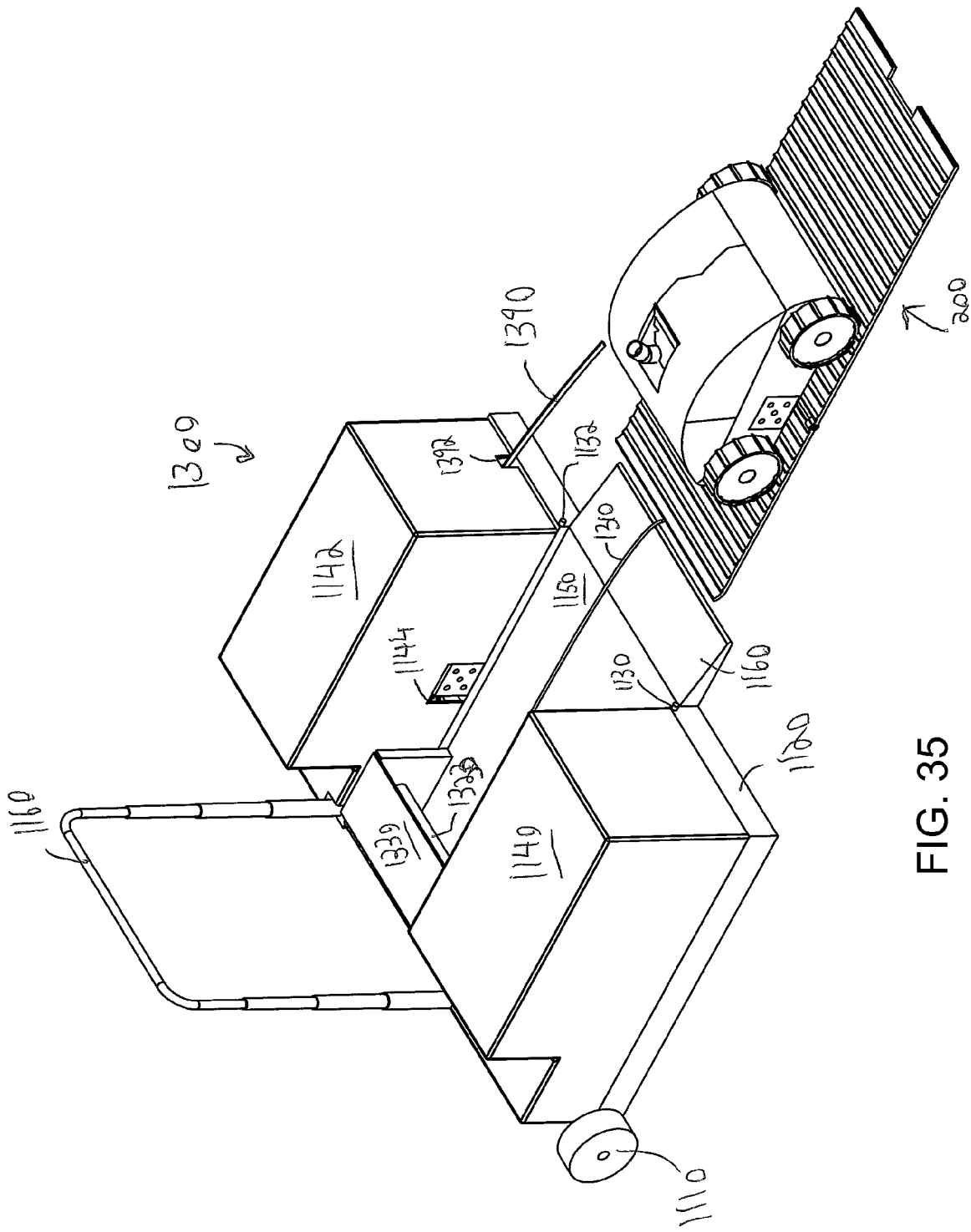

FIG. 35 illustrates the external docking station 1300 according to an embodiment of the invention. External docking station 1300 differs from external docking station 1100 of FIG. 32 by further including winding and unwinding mechanism—that is represented by axle 1333 of rotation.

Any winding and unwinding mechanism known in the art may be provided. The winding and unwinding mechanism may include one or more shafts, one or more motors, one or more transmission mechanisms (such as gears), and the like. Non-limiting examples of winding and unwinding mechanisms are shown in US patent application 20130092779, US patent application 2010/0170032 of Sproatt, U.S. Pat. No. 4,675,922 of Colin, and US patent application 20010034906 of Last, all being incorporated herein by reference. The interfacing device 1200 is connected to a winding and unwinding mechanism that is arranged to rotate a shaft in different directions thereby winding or unwinding the interfacing device 200. The interfacing device 1200 may be elastic, for example, made of flexible PVC and/or made of multiple parts (such as ribs or slats) that may move in relation to each other during the winding and/or unwinding mechanism. The winding and/or unwinding mechanism may use any motor—hydraulic, electrical, solar powered, and the like. The interfacing device 1200 may be unwound when the external docking station system is in a predefined distance from the pool edge (that predefined distance may be the length of the external surface interface 1210 of interfacing device 1200). The external surface interface 1210 is positioned on an external surface that is external to the pool. The external docking system may be driven to another predefined distance (for example—1, 2, 3 meters from the edge of the pool) after the interfacing device 1200 is not in use (and is wrapped around the shaft).

The winding and unwinding mechanism is included within winding and unwinding mechanism housing 1330. The Winding and unwinding mechanism is arranged to wind and unwind interfacing device 1200 that is interfaced by the pool cleaning robot 100 during at least one process out of a pool exit process and a propagation process towards the external docking station.

In FIG. 35 the interfacing mechanism was already extracted from the pool and is headed towards external docking station 1300. Cable 1310 connects between the winding and unwinding mechanism and interfacing device 1200.

Figure 36:
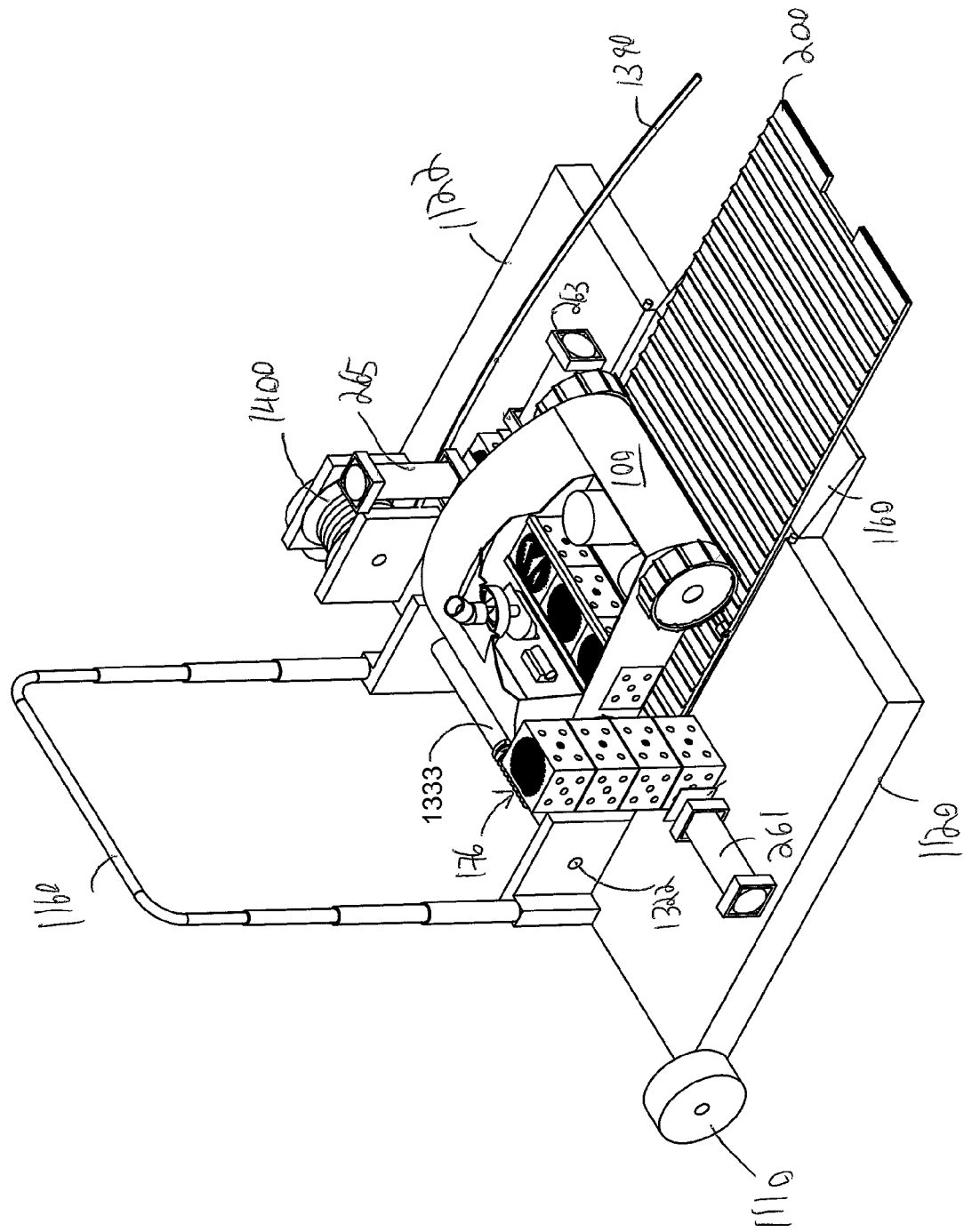
Figure 37:
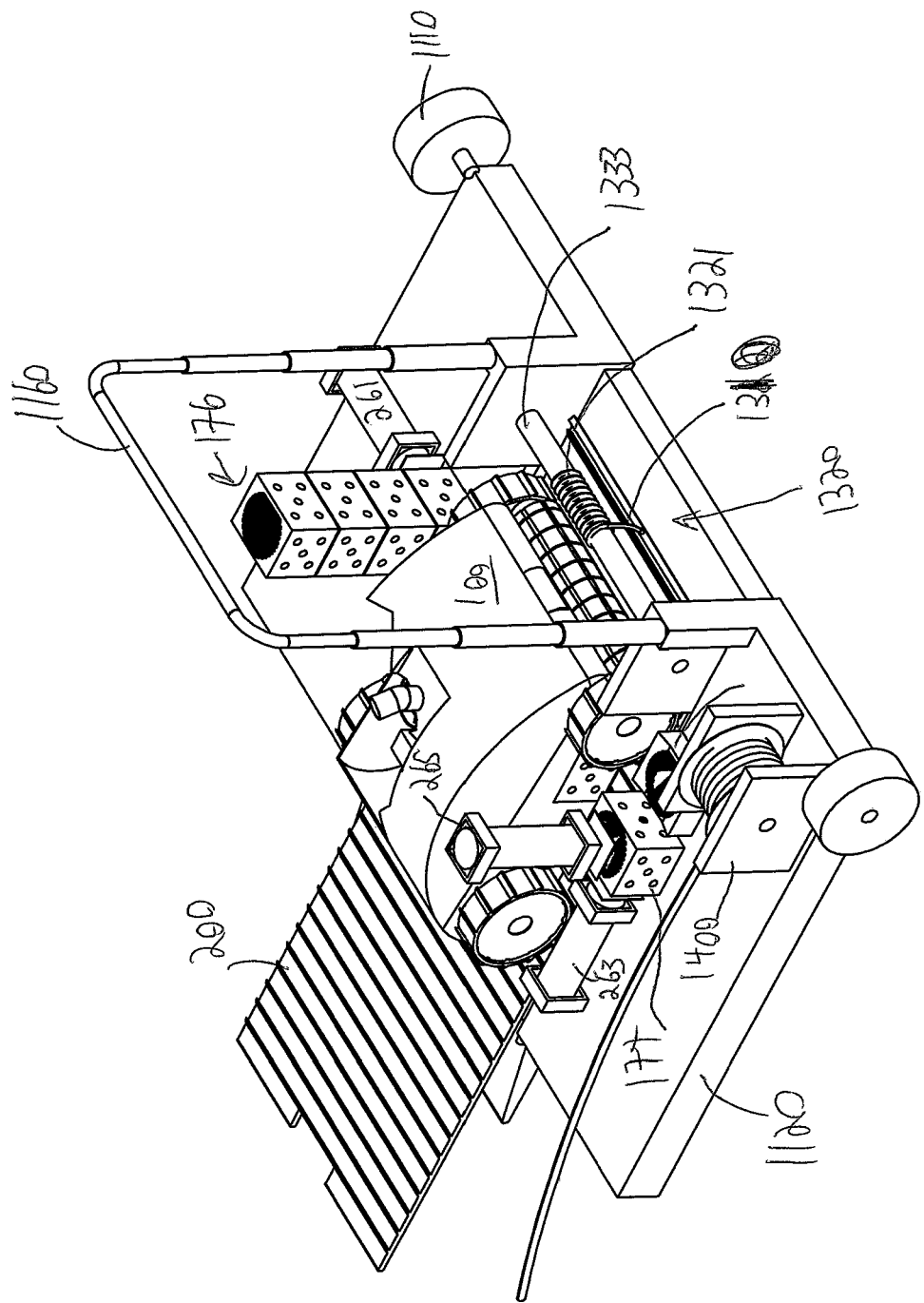

FIG. 36 and FIG. 37 illustrate external docking station 1300 according to an embodiment of the invention without the first housing, the second housing and the winding and unwinding mechanism housing. These housing were omitted for simplicity of explanation.

Winding and unwinding mechanism 1320 is illustrated as including axle 1333, cable 1310 that is partially wound over axel 1333 and a motor (not shown).

FIGS. 36-37 also show filters 176, used filter 177, compressed used filter 178 as well as various parts of the filter manipulator—including arm 261, arm 263, arm 265. FIGS. 36 and 37 also illustrate power cable winding and unwinding module 1400 for winding and unwinding power cable 1390. Arms 261, 263 and 265 may be replaced by any other component capable of manipulating filters.

Any external docking station may be self-propelled secured by wheel stoppers (not shown) to avoid slipping into the pool water, may be moved by a person, may be fixed to a certain position, and the like.

FIGS. 38A, 38B and 38C illustrate interfacing device 1200 according to an embodiment of the invention.

Interfacing device 1200 may include pool sidewall interface 1220 and an external surface interface 1210 that may be oriented to each other (for example by ninety degrees).

At least one (or none) of the external surface interface 210 and the pool sidewall interface 220 may include magnets such as magnets 224 of pool sidewall interface 220.

At least one (or none) of the external surface interface 210 and the pool sidewall interface 220 may include (at its internal side) attachment elements such as adhesive elements (such as a double sided adhesive tape), screws, vacuum nipples or suction cups 222 for connecting the interfacing device 200 to the side wall of the pool and to the external surface. Similar surface interfaces may be included and preinstalled in an original pool construction that may be prefabricated from a variety of matching materials so that an interface may be integrated onto the pool wall by the pool builder.

It is noted that although FIGS. 38A-38C illustrate the interfacing device as including two non-flat sheets that other interfacing elements may be used. For example, at least one of the external surface interface and the pool sidewall interface may be made of a group of elements (such as ribs) that are connected to each other (in a detachable or non-detachable manner).

The pool sidewall interface 220 of different lengths may be provided in order to allow it to fit to pools of different depths or to provide different penetration levels to the fluid in the pool (at least 10 cm and even till the bottom of the pool). Alternatively, the pool sidewall interface 220 may include multiple portions that can be connected to each other in order to provide a pool sidewall interface of different lengths (see, for example FIG. 38B).

At least one (or none) of the external surface interface 210 and the pool sidewall interface 220 may include a non-flat surface for interfacing with the pool cleaning robot during the exit process.

FIGS. 38A-38C illustrate the external surface interface 210 as having fins 211 that extend upwards and away from the pool. FIGS. 38A-38C illustrate the pool sidewall interface 220 as having fins 223 that extend upwards (while being not normal to the pool sidewall interface 220). These fins may be integrated onto a slat strip that extend the entire width of the sidewall interface. The fins and/or the slats can be replaced by any other sized and shaped protuberances. The length of the external surface interface and/or the pool sidewall interface may be adjusted by the addition or retraction of finned slats. Additionally or alternatively one or more of the external surface interface 210 and the pool sidewall interface 220 may include only depressions and/or a combination of depressions and protuberances. These figures also show that an edge of interfacing device—formed between the external surface interface 210 and the pool sidewall interface there may be a roller 230—that may rotate about its axis and may ease the exit process of the cleaning robot. The roller 230 may be fastened to other parts of the interfacing device by rings and/or friction bearings or any other manner. The roller may have a cylindrical shape. There may be more than one roller. The roller may be smooth or may have a non-smooth surface. The roller 230 may assist in the contact with the bottom external surface "underbelly" of the pool cleaner (not shown) in order to reduce friction and enable a smooth and rolled exit/entry of the pool cleaner.

The shape and size of any depressions and protuberances may match the shape and size of depressions and protuberances of the interfacing modules.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

Those skilled in the art to which this invention pertains will readily appreciate that numerous changes, variations and modifications can be made without departing from the scope of the invention mutatis mutandis.

We claim:

1. An external docking station, comprising: a filter manipulator that is arranged to (i) input without human intervention, a filter into a pool cleaning robot that exited a pool and is located in a filter replacement position and to (ii) assist without human intervention, in positioning the filter at a filtering position in which the filter is at least partially disposed within a fluid path formed between a first fluid opening and a second fluid opening of a housing of the pool cleaning robot thereby allowing the filter to apply a filtering operation on fluid that passes through the fluid path.

2. The external docking station according to claim 1 wherein the filter manipulator comprises a filter storage module that comprises a first portion that is arranged to store the filter before the filter is inputted to the pool cleaning robot and a second portion that is arranged to store a used filter after the the used filter was outputted from the pool cleaning robot; wherein when the pool cleaning robot is positioned at the filter replacement position then the pool cleaning robot is positioned between the first portion and the second portion.

3. The external docking station according to claim 1 further comprising a winding and unwinding mechanism that is arranged to wind and unwind an interfacing device that is interfaced by the pool cleaning robot during at least one process out of a pool exit process and a propagation process towards the external docking station.

4. The external docking station according to claim 3 wherein the filter manipulator comprises a filter storage module that comprises a first portion that is arranged to store the filter before the filter is inputted to the pool cleaning robot and a second portion that is arranged to store a used filter after the used filter was outputted from the pool cleaning robot; wherein there is a gap between the first portion and the second portion, wherein when the pool cleaning robot is positioned at the filter replacement position then the pool cleaning robot is positioned in the gap between the first portion and the second portion; wherein the winding and unwinding mechanism is configured to unwind the interface device thereby causing the interface device to propagate through the gap.

5. The external docking station according to claim 4 wherein the first portion is positioned within a first enclosure; wherein the second portion is positioned with a second enclosure.

6. The external docking station according to claim 1 comprising an electric cable winding and unwinding mechanism that is arranged to wind and unwind an electric cable that is configured to supply power to the pool cleaning robot.

7. The external docking station according to claim 6 wherein the filter manipulator comprises a filter storage module that comprises a first portion that is arranged to store the filter before the filter is inputted to the pool cleaning robot and a second portion that is arranged to store a used filter after the used filter was outputted from the pool cleaning robot; wherein the first portion is positioned within a first enclosure; wherein the second portion is positioned with a second enclosure; and wherein the electric cable winding and unwinding mechanism is positioned within the first enclosure or the second enclosure.

8. The external docking station according to claim 5 wherein the first enclosure comprises a first opening for outputting the filter into the pool cleaning robot; wherein the second enclosure comprises a second opening for receiving the used filter from the pool cleaning robot.

9. The external docking station according to claim 8 wherein the first opening and the second opening are positioned at a same relative location on the first and second enclosures respectively.

10. The external docking station according to claim 1 further comprising at least one power supply element for contacting at least one element of the pool cleaning robot and providing power to the at least one element of the pool cleaning robot.

11. The external docking station according to claim 10 wherein the at least one power supply element is positioned in a second housing; wherein the filter manipulator comprises a filter storage module that comprises a first portion that is arranged to store the filter before the filter is inputted to the pool cleaning robot and a second portion that is arranged to store a used filter after the used filter was outputted from the pool cleaning robot.

12. The external docking station according to claim 11 wherein the first portion, the second portion and the second housing are positioned at three sides of the pool cleaning robot when the pool cleaning robot is positioned at the filter replacement position.

13. The external docking station according to claim 1 comprising at least one rotating element for interfacing between the external docking station and a surface on which the external surface propagates.

14. The external docking station according to claim 1 comprising a first contactless charging element that is arranged to (a) be fed by an electrical supply module and (b) generate an electromagnetic field during at least one period during which a second contactless charging element of a pool cleaning robot is within a charging range from the first contactless charging element, and wherein the electromagnetic field charges the second contactless charging element.

15. The external docking station according to claim 1 comprising at least one radiation source for emitting electromagnetic radiation.

16. The external docking station according to claim 1 comprising multiple spaced apart radiation sources for emitting electromagnetic radiation that assist in a navigation of the pool cleaning robot towards the external docking station.

17. The external docking station according to claim 1 comprising a washing module for washing the pool cleaning robot internal cavity.

18. The external docking station according to claim 1 comprising a fluid conduit that faces an opening of the pool cleaning robot and is configured to washing an interior of the pool cleaning robot.

19. The external docking station according to claim 1 wherein the filter manipulator is arranged to position the filter at the filtering position.

20. The external docking station according to claim 1 wherein the filter manipulator is arranged to receive multiple filters and to feed at least two filters in the robot.

21. The external docking station according to claim 1 wherein the filter manipulator comprises a filter storage module that is arranged to store multiple used filters after the used filters were outputted from the pool cleaning robot.

22. The external docking station according to claim 1 wherein the filter manipulator comprises a filter storage module that is arranged to store multiple filters before the multiple filters are inputted to the pool cleaning robot.

23. The external docking station according to claim 1 wherein the filter manipulator comprises a filter storage module that is arranged to store multiple used filters after the used filters were outputted from the pool cleaning robot and is arranged to store multiple filters before the multiple filters are inputted to the pool cleaning robot.

24. The external docking station according to claim 1 wherein the filter manipulator comprises a first portion for storing the filter and for feeding the filter to the pool cleaning robot and a second portion for receiving one or more used filters from the robot.

25. The external docking station according to claim 24 wherein the first portion is configured to push a filter onto the pool cleaning robot thereby causing a used filter to exit the robot and be provided to the second portion.

26. The external docking station according to claim 1 wherein the filter manipulator comprises (a) a filter storage module that is arranged to store multiple filters, and (b) a movement mechanism.

27. The external docking station according to claim 26 wherein the movement mechanism is arranged to move at least one of the filter storage module and the filter in order to input the filter into the pool cleaning robot.

28. The external docking station according to claim 26 wherein the movement mechanism is further arranged to assist in moving the filter within the housing thereby placing another filter of the multiple filters at the filtering position.

29. The external docking station according to claim 26 wherein the filter storage module has a radial symmetry.

30. The external docking station according to claim 26 wherein the movement mechanism comprises (a) a rotation unit that is arranged to rotate the filter storage module thereby positioning the filter in front of a filter opening formed in the pool cleaning robot, and (b) an insertion and ejection module that is arranged to cause the filter to pass through the filter opening.

31. The external docking station according to claim 30 wherein the filter opening is formed at the bottom of the pool cleaning robot and wherein the insertion and ejection module is arranged to lift the filter and insert the filter into the pool cleaning robot through the filter opening.

32. The external docking station according to claim 26 wherein the movement mechanism is arranged to input the filter in the pool cleaning robot by moving the filter without moving a filter storage module of the filter manipulator.

33. The external docking station according to claim 26 wherein the filter manipulator is arranged to assist in an outputting of the filter from the robot.

34. The external docking station according to claim 1 further comprising a processing module for processing used filters that were outputted from the pool cleaning robot.

35. The external docking station according to claim 34 wherein the processing module is arranged to compress the used filters.

36. The external docking station according to claim 34 wherein the processing module is arranged to shred the used filters.

37. The external docking station according to claim 34 wherein the processing module is arranged to sanitize the used filters.

38. The external docking station according to claim 1 further comprising a sanitizer for sanitizing used filters.

39. A docking station, comprising: a filter or a debris collecting container manipulator that is arranged to (i) input without human intervention, a filter or a debris collecting container into a cleaning robot that exited a work area and is located in a filter or a debris collecting container replacement position and to (ii) assist without human intervention, in positioning the filter or a debris collecting container at a filtering or debris collecting position in which the filter or debris collecting container is at least partially disposed within a fluid or a debris collecting path formed between a first fluid or debris ingress opening and a second egress opening in the housing thereby allowing the filter or debris collecting container to apply a filtering or debris ingress operation on fluid or debris that passes through the fluid or debris collecting path.

* * * * *